(12) United States Patent
Marmorstein et al.

(10) Patent No.: US 8,476,458 B2
(45) Date of Patent: Jul. 2, 2013

(54) METHODS AND COMPOSITIONS FOR MODULATING P300/CBP ACTIVITY

(75) Inventors: Ronen Marmorstein, Swarthmore, PA (US); Xin Liu, Menlo Park, CA (US); Philip A. Cole, Baltimore, MD (US); Ling Wang, Seattle, WA (US); Erin M. Bowers, Baltimore, MD (US); David J. Meyers, Towson, MD (US); Chandrani Mukherjee, Baltimore, MD (US)

(73) Assignees: The Wistar Institute, Philadelphia, PA (US); The John Hopkins University, Baltimore, MD (US)

( * ) Notice: Subject to any disclaimer, the term of this patent is extended or adjusted under 35 U.S.C. 154(b) by 246 days.

(21) Appl. No.: 12/665,751

(22) PCT Filed: Jun. 19, 2008

(86) PCT No.: PCT/US2008/067477
§ 371 (c)(1),
(2), (4) Date: May 5, 2010

(87) PCT Pub. No.: WO2008/157680
PCT Pub. Date: Dec. 24, 2008

(65) Prior Publication Data
US 2010/0216853 A1    Aug. 26, 2010

Related U.S. Application Data

(60) Provisional application No. 60/945,404, filed on Jun. 21, 2007.

(51) Int. Cl.
| C07D 231/00 | (2006.01) |
| C07D 231/06 | (2006.01) |
| C07D 307/00 | (2006.01) |
| C07D 317/00 | (2006.01) |
| C07D 323/02 | (2006.01) |

(52) U.S. Cl.
USPC ............... 548/365.7; 548/356.1; 548/366.1; 548/379.1; 549/429

(58) Field of Classification Search
None
See application file for complete search history.

(56) References Cited

U.S. PATENT DOCUMENTS
2005/0282840 A1* 12/2005 Ross et al. .............. 514/269
2006/0084085 A1*  4/2006 Sinclair et al. ........... 435/6

OTHER PUBLICATIONS

Watanabe et al. "Structure-activity relationship of 3-methyl-1-phenyl-2-pyrazolin-5-one (edaravone)", Redox Report, 2003, vol. 8, No. 3, pp. 151-155.*

Moreau et al. "Discovery of new Gram-negative antivirulence drugs: Structure and properties of novel E. coli WaaC inhibitors", Bioorg. Med.Chem.Lett., available online Jun. 5, 2008, vol. 18, issue 14, pp. 4022-4026.*
Kalluraya et al. "Studies on the Synthesis and Biological Activity of some 4-(5-Aryl-2-furfurylidene)-1,3-disubstituted-2-pyrazolin-5-ones", J.Ind.Chem.Soc., 1995, vol. 72, pp. 99-101.*
Cebrat et al. "Synthesis and Analysis of Potential Prodrugs of Coenzyme A Analogues for the Inhibition of the Histone Acetyltransferase p300" Bioorganic & Medicinal Chemistry 2003 vol. 11: 3307-3313
Legge et al. "ZZ Domain of CBP: an Unusual Zinc Finger Fold in a Protein Interaction Module" Journal of Molecular Biology 2004 vol. 343: 1081-1093.
Lau et al. "HATs Off: Selective Synthetic Inhibitors of the Histone Acetyltransferase p300 and PCAF" Molecular Cell 2000 vol. 5: 589-595.
Legge et al. "ZZ Domain of CBP: an Unusual Zinc Finger Fold in a Protein Interaction Module" Journal of Molecular Biology 2004 vol. 343: 1081-1093.
Martinez-Balbas et al. "The Acetyltransferase Activity of CBP Stimulates Transcription" The EMBO Journal 1998 vol. 17(10): 2886-2893.
Mujtaba et al. "Structural Mechanism of the Bromodomain of the Coactivator CBP in p53 Transcriptional Activation" Molecular Cell 2004 vol. 13: 251-263.
Poux et al. "Structure of the GCN5 Histone Acetyltransferase Bound to a Bisubstrate Inhibitor" Proceedings of the National Academy of Science USA 2002 vol. 99(22): 14065-14070.
Radharkrishnan et al. "Solution Structure of the KIX Domain of CBP Bound to the Transactivation Domain of CREB: A Model for Activator:Coactivator Interactions" Cell 1997 vol. 91: 741-752.
Thompson et al. "Transcriptional Coactivator Protein p300" The Journal of Biological Chemistry 2001 vol. 276(36): 33721-33729.
Vetting et al. "Structure and Functions of the GNAT Superfamily of Acetyltransferase" Archives of Biochemistry and Biophysics 2005 vol. 433: 212-226.
Yuan, L.W. and Giordano, A. "Acetyltransferase Machinery Conserved in p300/CBP-Family Proteins" Oncogene 2002 vol. 21: 2253-2260.
Zhang et al. "Genome-Wide Analysis of cAMP-Response Element Binding Protein Occupancy, Phosphorylation, and Target Gene Activation in Human Tissues" Proceedings of the National Academy of Science 2005 vol. 102(12): 4459-4464.

* cited by examiner

*Primary Examiner* — James D Anderson
*Assistant Examiner* — Stephanie Springer
(74) *Attorney, Agent, or Firm* — Licata & Tyrrell P.C.

(57) ABSTRACT

The present invention relates to a method for identifying compounds that modulate the activity of p300/CBP. Compounds of the invention are identified by designing or screening for a compound which binds to at least one amino acid residue of the newly identified lysine-CoA inhibitor binding site, L1 loop, electronegative pocket, or electronegative groove of the HAT domain of p300/CBP and testing the compound for its ability to modulate the activity of p300/CBP. Compositions and methods for preventing or treating diseases or disorders associated with p300/CBP are also provided as is a method for producing a semi-synthetic HAT domain.

2 Claims, 8 Drawing Sheets

H4-CoA-20-L

H4-CoA-20-X

H4-CoA-20-Z

METHODS AND COMPOSITIONS FOR MODULATING P300/CBP ACTIVITY

This application is the U.S. National Stage of PCT/US2008/067477 filed Jun. 19, 2008 and claims benefit of priority to U.S. Provisional Application Ser. No. 60/945,404, filed Jun. 21, 2007, the content of which is incorporated herein by reference in its entirety.

This invention was made with government support under grant Nos. GM060293 and GM062437 awarded by the National Institutes of Health. The government has certain rights in the invention.

BACKGROUND OF THE INVENTION

The CBP and p300 paralogs were identified by their roles in regulating cyclic AMP-related gene activation and binding to adenoviral protein E1A, respectively (Chrivia, et al. (1993) *Nature* 365:855-859; Eckner, et al. (1994) *Genes Dev.* 8:869-884). One or more copies of the p300/CBP transcriptional coactivator is encoded in organisms from worm to man, and they have been intensively studied because of their diverse and important roles in complex biological processes (Goodman & Smolik (2000) *Genes Dev.* 14:1553-1577). The p300/CBP protein is ~250 kDa and contains a number of well-defined domains, many of which are crucial for its recruitment by a wide range of transcription factors (Legge, et al. (2004) *J. Mol. Biol.* 343:1081-1093; Mujtaba, et al. (2004) *Mol. Cell.* 13:251-263; Radhakrishnan, et al. (1997) *Cell* 91:741-752). p300/CBP has been shown to possess intrinsic histone acetyltransferase (HAT) activity which has led to a wide array of insights into its biological activities (Bannister & Kouzarides (1996) *Nature* 384:641-643; Ogryzko, et al. (1996) *Cell* 87:953-959). For example, p300/CBP HAT activity is important for its ability to act as a coactivator for a variety of transcription factors, e.g., p53, NFκB, STAT3, GATA-1, MyoD, TCF, androgen receptor (AR), and HIV Tat; thereby indicating that its HAT activity is important for a variety of pathways including cancer (Iyer, et al. (2004b) *Oncogene* 23:4225-4231), HIV (Kaehlcke, et al. (2003) *Mol. Cell.* 12:167-176) and HTLV-1 (Georges, et al. (2003) *Mol. Cell. Biol.* 23:3392-3404) pathogenesis; as well as, cardiac remodeling (Gusterson, et al. (2003) *J. Biol. Chem.* 278:6838-6847), glucose regulation (van der Heide & Smidt (2005) *Trends Biochem. Sci.* 30:81-86), oxygen sensing (Roe, et al. (2006) *Mol. Cell.* 22:395-405), and steroid hormone signaling (Korzus, et al. (1998) *Science* 279:703-707). In addition to catalyzing the acetylation of multiple lysines on all four core histones, p300/CBP has been shown to acetylate a wide array of transcription factors and other proteins as part of its functions. Some of these p300/CBP-acetylated substrates include p53, p73, NFκB, STAT3, GATA-1, MyoD, TCF, E2F1, HMG14, HMGI(Y), androgen receptor (AR), Tat, and c-Myb (Chen, et al. (2001) *Science* 293:1653-1657; Costanzo, et al. (2002) *Mol. Cell.* 9:175-186; Thompson, et al. (2001) *J. Biol. Chem.* 276:33721-33729; Yuan, et al. (2005) *Science* 307:269-273). Although there are no precise consensus sequences for p300/CBP-mediated acetylation, there is a clear preference for nearby positively charged residues influencing targeted lysine acetylation (Thompson, et al. (2001) supra).

As noted above, p300/CBP plays a key role in regulating the transcription of a large subset of eukaryotic genes. Consistent with this important role is the fact that mutations, altered expression, and gene rearrangements of p300/CBP have been observed in a variety of diseases including cancer (Iyer, et al. (2004b) supra). For example, patients with Rubinstein-Taybi Syndrome, which involves a heterozygous mutation in one CBP allele (Murata, et al. (2001) *Hum. Mol. Genet.* 10:1071-1076), have an increased incidence of tumors. Additionally, point mutations thought to interfere with the catalytic activity of p300/CBP have been observed in pancreatic cancer (Gayther, et al. (2000) *Nat. Genet.* 24:300-303), colon cancer (Muraoka, et al. (1996) *Oncogene* 12:1565-1569), and lung cancer (Kishimoto, et al. (2005) *Clin. Cancer Res.* 11:512-519). Gene fusion events involving the CBP HAT domain have been detected in a number of acute leukemias (Borrow, et al. (1996) *Nat. Genet.* 14:33-41). Finally, overexpression of p300/CBP has been detected in a variety of cancers including colon (Pena, et al. (2006) *Int. J. Cancer* 119:2098-2104), gastric (Kim, et al. (2007) *Am. J. Physiol. Cell Physiol.* 292:C857-866), and thyroid (Fluge, et al. (2006) *Thyroid* 16:161-175) carcinoma.

The coactivator activity of p300/CBP is controlled at multiple levels and its regulation has been studied (Goodman & Smolik (2000) supra). For example, p300/CBP is known to be phosphorylated, methylated, ubiquitinated, sumoylated, and acetylated and these modifications exert a myriad of effects on p300/CBP coactivator activity by modulating its protein levels, its interactions with other proteins, and its HAT activity (Goodman & Smolik (2000) supra; Thompson, et al. (2004) *Nat. Struct. Mol. Biol.* 11:308-315). Regarding acetylation, there are a dense cluster of lysines in a flexible loop region of the p300/CBP HAT domain that are sites of autoacetylation (Thompson, et al. (2004) supra). Intermolecular autoacetylation of these lysines appears to upregulate p300/CBP HAT activity (Thompson, et al. (2004) supra) and also modulate protein-protein interactions with APC (Turnell, et al. (2005) *Nature* 438:690-695), PIC (Black, et al. (2006) *Mol. Cell.* 23:809-818), and ATF-2 among possibly others. Partial deletion of this p300/CBP autoacetylated loop can upregulate HAT activity and modulate transcriptional activation (Thompson, et al. (2004) supra).

Studies investigating the structure, mechanism, and inhibition of different HATs have been conducted. The most well-understood HATs are the paralogs PCAF and GCN5, and these enzymes appear to be classical members of the GNAT superfamily (Neuwald & Landsman (1997) *Trends Biochem. Sci.* 22:154-155) based on structure and catalytic mechanism (Vetting, et al. (2005) *Arch. Biochem. Biophys.* 433:212-226). The GNAT superfamily is composed of weakly conserved acetyltransferases with ~200 residue catalytic domains that show a similar core protein fold and include enzymes involved in antibiotic resistance, melatonin biosynthesis, and polyamine metabolism (Vetting, et al. (2005) supra). The catalytic mechanism of PCAF/GCN5 and most other GNATs usually involves a ternary complex mechanism with ordered binding of the acetyl-CoA substrate prior to the amine substrate (Vetting, et al. (2005) supra). Upon ternary complex formation, there is direct transfer of the acetyl group from acetyl-CoA to the substrate amino group. The α-β fold for acetyl-CoA binding is quite conserved and many of these enzymes appear to have a catalytic base assisting in amine substrate deprotonation (Vetting, et al. (2005) supra). Bisubstrate analog inhibitors in which the amine substrate are linked to coenzyme A via an acetyl bridge have proved to be powerful inhibitors for these enzymes and have been extensively used in biochemical and structural studies (Vetting, et al. (2005) supra).

Sequence alignments and enzymology experiments on p300/CBP have led to somewhat confusing and contradictory results regarding the mechanism of p300/CBP and its structural relationship to PCAF/GCN5. For example, sequence alignments of p300/CBP and PCAF/GCN5 (Martinez-Balbas, et al. (1998) *EMBO J.* 17:2886-2893; Yuan & Giordano (2002) *Oncogene* 21:2253-2260) have shown limited homology that appears to be inconsistent with the PCAF/GCN5 structure (Poux, et al. (2002) *Proc. Natl. Acad. Sci. USA* 99:14065-14070). Additionally, a two substrate kinetic analysis showed a parallel line pattern suggestive of a ping-pong kinetic mechanism with a covalent enzyme intermediate (Thompson, et al. (2001) supra), potentially similar to the mechanism employed by Esal (Berndsen, et al. (2007) *Biochemistry* 46:623-629) and different from PCAF/Gcn5 (Tanner, et al. (1999) *J. Biol. Chem.* 274:18157-18160; Trievel, et al. (1999) *Proc. Natl. Acad. Sci. USA* 96:8931-8936; Vetting, et al. (2005) supra). However, experiments with acetyl-CoA-based affinity labeling agents failed to identify a key active site nucleophilic residue that would play a role in forming a covalent intermediate. Interestingly, the nominal bisubstrate analog Lys-CoA in which a derivatized lysine is bridged to coenzyme A via an acetyl linker is a powerful and selective inhibitor of p300/CBP (Lau, et al. (2000) *Mol. Cell.* 5:589-595). Paradoxically, longer peptide-CoA conjugates, based on better peptide substrates of p300 HAT, are weaker p300 HAT inhibitors (Lau, et al. (2000) supra). This pattern is reversed for PCAF/GCN5 where longer rather than shorter peptide-CoA conjugates are better HAT PCA Compound F/GCN5 inhibitors (Lau, et al. (2000) supra), consistent with their substrate behaviors and ternary complex mechanisms. Interestingly, deletion of the 3'-phosphate from Lys-CoA results in a 30-fold reduction in p300 HAT inhibitory potency (Cebrat, et al. (2003) *Bioorg. Med. Chem.* 11:3307-3313). In contrast, for a GNAT superfamily member serotonin N-acetyltransferase bisubstrate analog the 3'-phosphate is essentially completely dispensable (Khalil, et al. (1999) *Proc. Natl. Acad. Sci. USA* 96:12418-12423). Taken together, these studies provide little information of the nature of p300/CBP HAT mechanism and structure.

SUMMARY OF THE INVENTION

The present invention is a method for identifying a compound which modulates the activity of p300/CBP. The method of this invention involves, (a) designing or screening for a compound which binds to at least one amino acid residue of the lysine-CoA inhibitor binding site, L1 loop, electronegative pocket, or electronegative groove of the HAT domain of p300/CBP; and (b) testing the compound designed or screened for in (a) for its ability to modulate the activity of p300/CBP, thereby identifying a compound that modulates the activity of p300/CBP. In one embodiment, the compound binds to the substrate binding site and inhibits the activity of p300/CBP. In other embodiments, step (a) is carried out in silico or in vitro. Compounds identified by the present invention and pharmaceutical compositions containing the same are also provided.

The present invention also provides a method for making an inhibitor of p300/CBP. This method involves screening for a compound which interacts with amino acid residues Arg1410, Thr1411, Trp1466, and Tyr1467 of SEQ ID NO:1 or amino acid residues Arg1446, Thr1447, Trp1502 and Tyr1503 of SEQ ID NO:2 thereby making an inhibitor of p300/CBP.

Methods for inhibiting the activity of p300/CBP and preventing or treating cancer, diabetes, or obesity using one or more p300/CBP inhibitors of the invention are also provided.

The present invention is also a method for producing a semi-synthetic HAT domain. The method involves subjecting a HAT domain and N-Cys peptide of p300/CBP to expressed protein ligation to produce a semi-synthetic HAT domain; and subjecting the semi-synthetic HAT domain to proteolysis in the presence of an inhibitor thereby producing a heterodimeric HAT complex.

BRIEF DESCRIPTION OF THE DRAWINGS

FIG. 1 shows the structure of p300 and preparation and structure of p300 HAT domain.

FIG. 6 shows the anticipated catalytic mechanism of p300 HAT.

DETAILED DESCRIPTION OF THE INVENTION

Figure 1A:
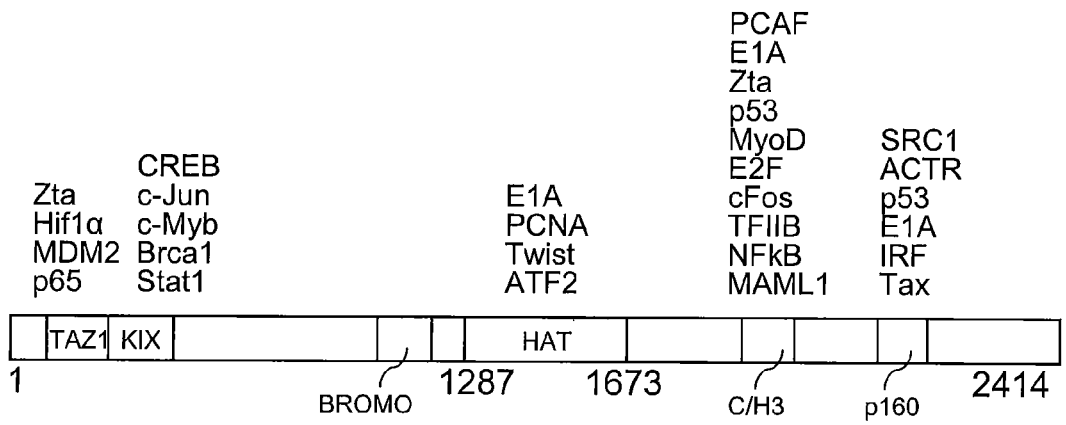
FIG. 1A is a schematic representation of p300 domain structure with selected interacting proteins.

The transcriptional coactivator p300/CBP is a histone acetyltransferase (HAT) that regulates gene expression by acetylating histones and other transcription factors and the dysregulation of p300/CBP HAT activity contributes to various diseases including cancer. The p300/CBP proteins contain a number of well-defined domains (FIG. 1A), many of which are crucial for recruitment by a wide range of transcription factors. The high-resolution crystal structure of the human p300 HAT domain in complex with a specific bisubstrate analog inhibitor, Lys-CoA, has now been determined. The structure reveals similarity with other HAT domains in the CoA-binding region, despite the lack of sequence conservation within this region, and a novel, and presumably flexible, cofactor-binding loop within the CoA-binding core region that makes additional interactions with cofactor. HAT regions flanking the core CoA binding regions show significant structural divergence with other HATs and appears to help form a unique substrate recognition region. Structure-guided mutagenesis indicates that p300/CBP uses a different catalytic mechanism than other HATs. Mapping of p300 tumor-derived mutations onto the HAT domain structure also highlights the key role of HAT domain integrity and cofactor binding in particular in maintaining p300 tumor suppressor activity.

Because of the involvement of p300/CBP in a growing number of cellular processes, p300/CBP is a therapeutic drug target for the development of small molecule effectors. The term "effector" refers to any agonist, antagonist, ligand or other agent that affects the activity of p300/CBP used in the assays of the present invention. Effectors can be, but are not limited to, peptides, carbohydrates, nucleic acids, lipids, fatty acids, hormones, organic compounds, and inorganic compounds. The information obtained from the inhibitor-bound p300 complex crystal structures of the present invention reveal detailed information which is useful in the design, isolation, screening and determination of potential compounds which modulate the activity of p300 proteins. Compounds that bind the L1 loop, electronegative pocket, or electronegative groove, and either sterically block substrate binding, lysine-CoA inhibitor binding, or the acetylation reaction may act as effective p300/CBP-specific inhibitors. Accordingly, the present invention provides methods for identifying a compound which modulates the activity of p300/CBP. Broadly, the methods involve designing or screening for a compound which binds to at least one amino acid residue of the L1 loop, electronegative pocket, or electronegative groove of the HAT domain of p300; and testing the compound designed or screened for its ability to modulate the activity of p300/CBP. In certain embodiments, the method of the present invention is carried out using various in silico, in vitro and/or in vivo assays based on detecting interactions between the HAT domain of p300/CBP and a test compound.

In the context of the present invention, p300/CBP refers to a family member of the p300/CBP family of coactivators which have histone acetyltransferase activity. p300 is described, e.g., by Eckner, et al. ((1994) *Genes Dev.* 8:869-884 and is provided in GENBANK Accession Nos. NP_001420 (human) and NP_808489 (mouse). The amino acid sequence of human p300 is set forth herein as SEQ ID NO:1. p300 is related by sequence to CBP (CREB-binding protein [CREB, cyclic-AMP responsive element binding protein]), and like CBP can stimulate transcription through activation of CREB. p300 has also been identified as a co-activator of HIF1A (hypoxia-inducible factor 1 alpha), and thus plays a role in the stimulation of hypoxia-induced genes such as VEGF. CBP is also known in the art and described, e.g., by Bannister & Kouzarides ((1996) *Nature* 384:641-643) and provided in GENBANK Accession Nos. NP_004371 (human), NP_596872 (rat), and NP_001020603 (mouse). The amino acid sequence of human CBP is set forth herein as SEQ ID NO:2. For the purposes of the present invention, reference to p300 or CBP refers to human allelic and synthetic variants of p300 or CBP, and to other mammalian variants and allelic and synthetic variants thereof, as well as fragments of said human and mammalian forms of p300 or CBP. Synthetic variants include those which have at least 80%, preferably at least 90%, homology to p300 or CBP. More preferably such variants correspond to the sequence of p300 or CBP but have one or more, e.g., from 1 to 10, such as from 1 to 5, substitutions, deletions or insertions of amino acids. Fragments of p300 or CBP and variants thereof are preferably at least 20, more preferably at least 50 and most preferably at least 200 amino acids in size.

Compounds designed or screened for in accordance with the present invention can interact with at least one of the amino acid residues of the Lys-CoA inhibitor binding site, L1 loop, electronegative pocket, electronegative groove or substrate binding site of the HAT domain of p300/CBP via various heterogeneous interactions including, but not limited to, van der Waals contacts, hydrogen bonding, ionic interactions, polar contacts, or combinations thereof.

As depicted in FIG. 1A, the HAT domain is composed of amino acid residues 1195-1673 of p300 (SEQ ID NO:1), which correspond to amino acid residues 1231-1710 of CBP (SEQ ID NO:2). As identified herein, the L1 loop of the HAT domain, flanked by the β5-strand and α4-helix, is involved in the binding of both the acetyl-CoA and lysine moieties of the Lys-CoA inhibitor. Accordingly, in one embodiment of the present invention, a compound of the invention binds to or interacts with at least one amino acid residue of the L1 loop. In the context of the present invention, the L1 loop is composed of amino acid residues 1436-1459 of p300 (SEQ ID NO:1) or the corresponding residues of CBP, i.e., amino acid residues 1472-1495. See FIG. 8.

Figure 3:
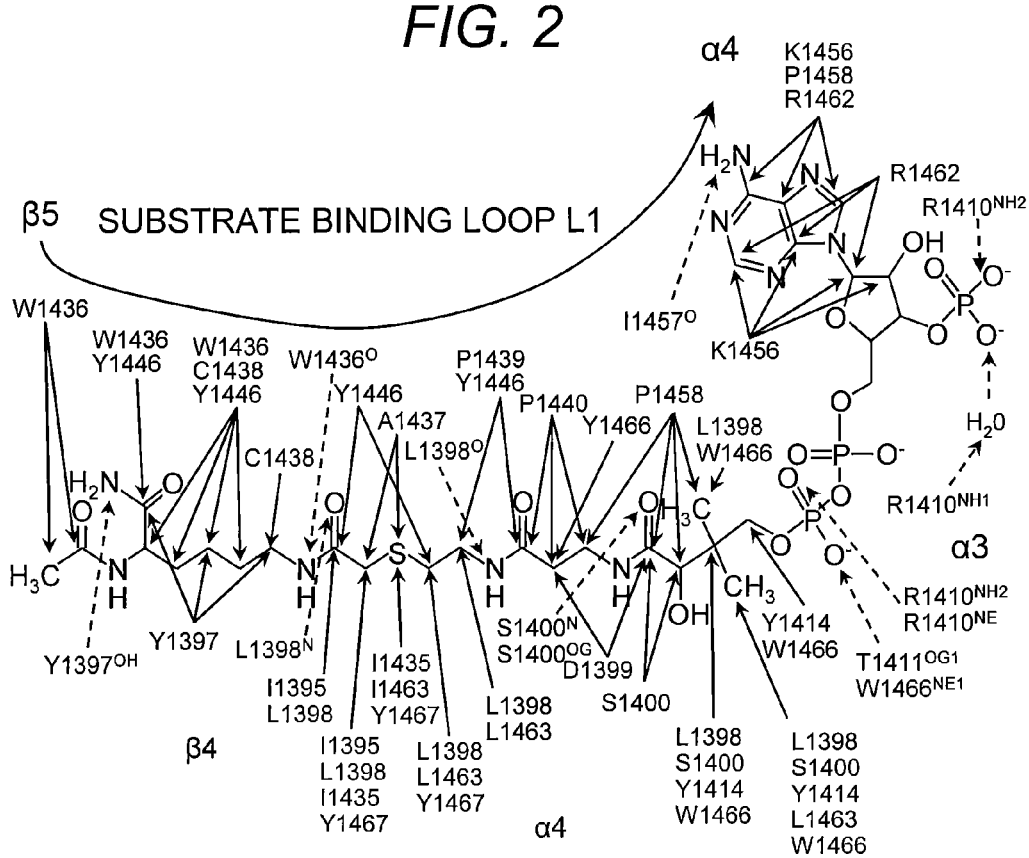
FIG. 3 is a schematic view of p300 HAT domain interactions with the Lys-CoA inhibitor. Hydrophobic interactions and hydrogen bonds are indicated with solid and dotted arrows, respectively.

Structure analyses disclosed herein further indicate that the edges of the α3-helix/β4-strand and α4-helix/β5-strand flank the other sides of the Lys-CoA inhibitor to form the Lys-CoA inhibitor binding site. In particular, FIG. 3 depicts amino acid residues of the p300 HAT domain which interact with the Lys-CoA inhibitor. As depicted, the CoA moiety of the Lys-CoA inhibitor interacts with at least Arg1410, Thr1411, Trp1466, Arg1462 and Ile1457 of p300, whereas the lysine moiety of the Lys-CoA inhibitor interacts with at least Trp1436, Tyr1397, Tyr1446, and Cys1438 of p300. Accordingly, particular embodiments of the present invention embrace a compound which binds to or interacts with at least one amino acid residue of Lys-CoA inhibitor binding site. In the context of the present invention, the Lys-CoA inhibitor binding site is composed of amino acid residues 1395-1467 of p300 (SEQ ID NO:1) or amino acid residues 1431-1503 of CBP (SEQ ID NO:2). In particular embodiments, the Lys-CoA inhibitor binding site includes one or more of amino acid residue 1395, 1397, 1398, 1399, 1400, 1410, 1411, 1414, 1435, 1436, 1437, 1438, 1439, 1440, 1446, 1456, 1457, 1458, 1462, 1463, 1466 and 1467 of p300 (SEQ ID NO:1), or one or more of amino acid residue 1431, 1433, 1434, 1435, 1436, 1446, 1447, 1450, 1471, 1472, 1473, 1474, 1475, 1476, 1482, 1492, 1493, 1494, 1498, 1499, 1502 and 1503 of CBP (SEQ ID NO:2).

In addition to the pocket that accommodates the lysine moiety of Lys-CoA, a second pronounced and highly electronegative pocket was identified. This second pocket, referred to herein as the "electronegative pocket", is composed of at least amino acid residues Thr1357, Glu1505, Asp1625, and Asp1628 of p300 (SEQ ID NO:1), i.e., amino acid residues Thr1393, Glu1541, Asp1662, and Asp1665 of CBP (SEQ ID NO:2). In addition, a narrow, shallow and electronegative groove connecting the two above-referenced pockets was identified. This groove, referred to herein as the "electronegative groove," is composed of at least amino acid residues Ser1396 and Tyr1397 of p300 (SEQ ID NO:1), or amino acid residues Ser1432 and Tyr1433 of CBP (SEQ ID NO:2). Based upon the structural and mutational analysis disclosed herein, the electronegative pocket and electronegative groove in conjunction with the pocket that accommodates the lysine moiety of Lys-CoA form the substrate binding site. Accordingly, in some embodiments, the present invention embraces a compound which binds to or interacts with at least one amino acid residue of the electronegative pocket or electronegative groove. In other embodiments, the present invention embraces a compound which binds to or interacts with at least one amino acid residue of the substrate binding site.

In general, it is desirable that a compound of the invention interacts with 2, 3, 4, 5, 6 or up to 25 amino acid residues of the L1 loop, electronegative pocket, electronegative groove, Lys-CoA inhibitor binding site or substrate binding site of the HAT domain of p300/CBP to enhance the specificity of the compound for p300/CBP.

In accordance with the present invention, molecular design techniques or in silico techniques can be employed to design, identify and synthesize chemical entities and compounds, including inhibitory and stimulatory compounds, capable of binding to the HAT domain. In accordance with designing compounds which modulate the activity of the HAT domain, any suitable method for determining the crystal structure of the HAT domain can be employed. However, because the production of recombinant p300/CBP HAT domain protein in quantities necessary for crystallization is difficult using conventional methods, particular embodiments of the present invention embrace a method for producing an heterodimeric HAT complex suitable for crystallization. As exemplified herein, a heterodimeric HAT complex can be produced by expressed protein ligation of the HAT domain with the N-Cys peptide of p300/CBP, wherein limited proteolysis in the presence of an inhibitor yields an active and minimally acetylated semi-synthetic HAT domain useful for subsequent crystallization. Expressed protein ligation is well-known in the art (see, e.g., Thompson, et al. (2004) supra) and depicted in FIG. 1B. In general, expressed protein ligation involves fusing the HAT domain (e.g., amino acid residues 1287-1652 of p300 or residues 1323-1689 of CBP which lack the N-Cys peptide) to a VMA intein-chitin binding domain, purifying the fusion protein with chitin resin, and converting the fusion protein to a C-terminal thioester, e.g., by treatment with MESNA. The purified fusion protein is then chemically ligated to the N-Cys peptide of the HAT domain (residues 1653-1666 of p300 or 1690-1703 of CEP) to produce an active and minimally acetylated semi-synthetic HAT domain. In particular embodiments, amino acid residues 1523-1554 of the p300 HAT domain or residues 1559-1590 of the CBP HAT domain are deleted and replaced with a potent lysine autoacetylation site as described herein to generate a loop-deleted semi-synthetic p300 HAT. Proteolysis (e.g., sequential lysis with trypsin and carboxypeptidase A and B) of the resulting semi-synthetic HAT domain in the presence of an inhibitor, e.g., Lys-CoA or other inhibitor (e.g., identified in a screening assay) then provides a heterodimeric HAT complex suitable for crystallization in accordance with conventional techniques.

The structure of the HAT domain can be used in conjunction with computer modeling using a docking program such as GRAM, DOCK, HOOK or AUTODOCK (Dunbrack, et al. (1997) *Folding & Design* 2:27-42) to identify potential modulators of p300/CBP. This procedure can include computer fitting of compounds to the L1 loop, electronegative pocket, electronegative groove, Lys-CoA inhibitor binding site or substrate binding site of the HAT domain to ascertain how well the shape and the chemical structure of the compound will complement these sites or to compare the compound with the binding of Lys-CoA. Computer programs can also be employed to estimate the attraction, repulsion and stearic hindrance of the HAT domain of p300/CBP and effector compound. Generally, the tighter the fit, the lower the stearic hindrances, the greater the attractive forces, and the greater the specificity which are important features for a specific effector compound which is more likely to interact with p300/CBP rather than other classes of proteins.

Alternatively, a chemical-probe approach can be employed in the design of p300/CBP modulators or effectors. For example, Goodford ((1985) *J. Med. Chem.* 28:849) describes several commercial software packages, such as GRID (Molecular Discovery Ltd., Oxford, UK), which probe the L1 loop, electronegative pocket, electronegative groove, Lys-CoA inhibitor binding site or substrate binding site of the HAT domain with different chemical probes, e.g., water, a methyl group, an amine nitrogen, a carboxyl oxygen, and a hydroxyl. Favored sites for interaction between these regions or sites of the HAT domain and each probe are thus determined, and from the resulting three-dimensional pattern of such regions or sites a putative complementary molecule can be generated.

The compounds of the present invention can also be designed by visually inspecting the three-dimensional structure of the HAT domain of p300 to determine more effective inhibitors or activators. This type of modeling is generally referred to as "manual" drug design. Manual drug design can employ visual inspection and analysis using a graphics visualization program such as "O" (Jones, et al. (1991) *Acta Crystallographica Section A* A47:110-119).

Initially effector compounds can be selected for their structural similarity to the X, Y and Z constituents of, e.g., Lys-CoA by manual drug design. The structural analog thus designed can then be modified by computer modeling programs to better define the most likely effective candidates. Reduction of the number of potential candidates is useful as it may not be possible to synthesize and screen a countless number of compound variations that may have some similarity to known inhibitory molecules. Such analysis has been shown effective in the development of HIV protease inhibitors (Lam, et al. (1994) *Science* 263:380-384; Wlodawer, et al. (1993) *Ann. Rev. Biochem.* 62:543-585; Appelt (1993) *Perspectives in Drug Discovery and Design* 1:23-48; Erickson (1993) *Perspectives in Drug Discovery and Design* 1:109-128). Alternatively, random screening of a small molecule library could lead to modulators whose activity may then be analyzed by computer modeling as described above to better determine their effectiveness as inhibitors or activators.

Programs suitable for searching three-dimensional databases include MACCS-3D and ISIS/3D (Molecular Design Ltd, San Leandro, Calif.), ChemDBS-3D (Chemical Design Ltd., Oxford, UK), and Sybyl/3 DB Unity (Tripos Associates, St Louis, Mo.). Programs suitable for compound selection and design include, e.g., DISCO (Abbott Laboratories, Abbott Park, Ill.), Catalyst (Bio-CAD Corp., Mountain View, Calif.), and ChemDBS-3D (Chemical Design Ltd., Oxford, UK).

The compounds designed using the information of the present invention can bind to all or a portion of the HAT domain of p300/CBP and may be more potent, more specific, less toxic and more effective than known inhibitors of p300/CBP. The designed compounds can also be less potent but have a longer half-life in vivo and/or in vitro and therefore be more effective at modulating p300/CBP activity in vivo and/or in vitro for prolonged periods of time. Such designed modulators are useful to inhibit or activate p300/CBP activity to, e.g., alter cyclic AMP-related gene activation; histone acetyltransferase activity; or coactivation of p53, NFκB, STAT3, GATA-1, MyoD, TCF, androgen receptor, and HIV Tat.

The present invention also provides the use of molecular design techniques to computationally screen small molecule databases for chemical entities or compounds that can bind to p300/CBP in a manner analogous to the Lys-CoA inhibitor as defined by the structure of the present invention. Such computational screening can identify various groups which interact with one or more amino acid residues of the Lys-CoA inhibitor binding site of the HAT domain of p300 and can be employed to synthesize modulators of the present invention.

In vitro (i.e., in solution) screening assays are also embraced by the present invention. Such assays include combining p300/CBP, the p300/CBP HAT domain (e.g., as disclosed herein), or portions of the p300/CBP HAT domain (e.g., sites, or fragments disclosed herein) with acetyl-CoA and a substrate (e.g., H4-15 peptide) in solution and determining whether a test compound can sterically block the subsequent acetylation reaction.

Compounds which can be screened in accordance with the method of the present invention are generally derived from libraries of agents or compounds. Such libraries can contain either collections of pure agents or collections of agent mixtures. Examples of pure agents include, but are not limited to, proteins, polypeptides, peptides, nucleic acids, oligonucleotides, carbohydrates, lipids, synthetic or semi-synthetic chemicals, and purified natural products. Examples of agent mixtures include, but are not limited to, extracts of prokaryotic or eukaryotic cells and tissues, as well as fermentation broths and cell or tissue culture supernates. Databases of chemical structures are also available from a number of sources including Cambridge Crystallographic Data Centre (Cambridge, UK) and Chemical Abstracts Service (Columbus, Ohio). De novo design programs include Ludi (Biosym Technologies Inc., San Diego, Calif.), Sybyl (Tripos Associates) and Aladdin (Daylight Chemical Information Systems, Irvine, Calif.).

Library screening can be performed using any conventional method and can be performed in any format that allows rapid preparation and processing of multiple reactions. For in vitro screening assays, stock solutions of the test compounds as well as assay components can be prepared manually and all subsequent pipeting, diluting, mixing, washing, incubating, sample readout and data collecting carried out using commercially available robotic pipeting equipment, automated work stations, and analytical instruments for detecting the signal generated by the assay. Examples of such detectors include, but are not limited to, luminometers, spectrophotometers, and fluorimeters, and devices that measure the decay of radioisotopes.

After designing or screening for a compound which binds to at least one amino acid residue of the L1 loop, electronegative pocket, electronegative groove, Lys-CoA inhibitor binding site or substrate binding site of the HAT domain or p300/CBP, the compound is subsequently tested for its ability to modulate the activity of p300/CBP. Such testing can be based upon whether the compound modulates the HAT activity of p300/CPB (e.g., in a HAT assay), coactivation activity, or based on binding activity. To measure binding constants (e.g., $K_d$), any suitable method known to those in the art can be employed including, e.g., BIACORE analysis, isothermal titration calorimetry, ELISA with a known drug on the plate to show competitive binding, or by a HAT activity assay. Alternatively, the compound can be co-crystallized with p300/CBP to determine the binding characteristics through X-ray crystallography techniques. See, for example, U.S. Pat. No. 7,149,280 which discloses a method for identifying a ligand of a target macromolecule by obtaining an X-ray crystal diffraction pattern of a compound bound to the macromolecule crystal.

In accordance with the methods of the present invention, compounds were screened to identify modulators of p300/CBP HAT activity. Virtual library screening identified compound 7 as a potent inhibitor of p300/CBP HAT. Based upon the structure of compound 7, several other known compounds with benzoate moieties linked to aryl groups were analyzed for inhibitory activity. These compounds and their percent inhibition of p300/CBP activity in a coupled spectrophotometric assay as well as a direct radioactive assay are listed in Table 1.

TABLE 1

| | | % Inhibition | |
|---|---|---|---|
| Compound | Structure | Coupled | Direct |
| 7 | [structure] | 85.9% | |

TABLE 1-continued

| Compound | Structure | % Inhibition | |
|---|---|---|---|
| | | Coupled | Direct |
| 17.2 | 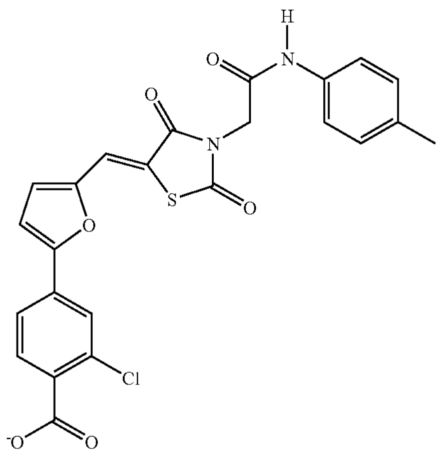 | | |
| 17.3 | 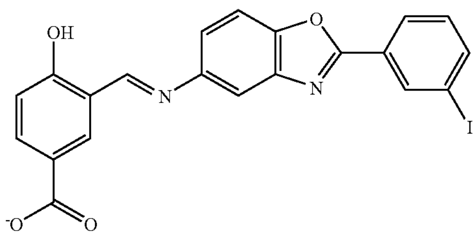 | | |
| 6328730 | 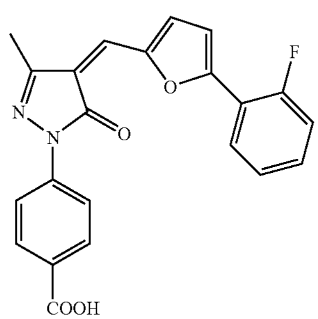 [SMILES: CC1=NN(c2ccc(C(=O)O)cc2)C(=O)/C1=C\c1ccc(-c2ccccc2F)o1] | 90.5% | 67.9% |
| 40174 | 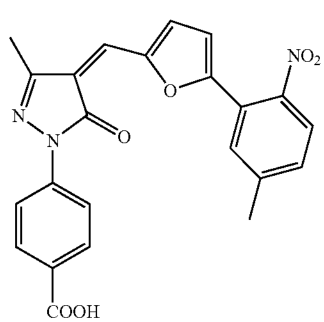 [SMILES: CC1=NN(c2ccc(C(=O)O)cc2)C(=O)/C1=C\c1ccc(-c2cc(C)ccc2[N+](=O)[O-])o1] | ND | 79.5% |

TABLE 1-continued

| Compound | Structure | % Inhibition Coupled | % Inhibition Direct |
|---|---|---|---|
| 6c | (structure) | 38.1% | 8.3% |

Pyrazolones 7, 6328730 and 40174 were obtained commercially from Chembridge, and Interbioscreen, respectively.

Novel analogs of compound 7 were also designed, synthesized, and screened for p300/CBP inhibitory activity.

These compounds and their percent inhibition of p300/CBP activity in a coupled spectrophotometric assay as well as a direct radioactive assay are listed in Table 2.

TABLE 2

| Compound | Structure | % Inhibition Coupled | % Inhibition Direct |
|---|---|---|---|
| 6a | (structure) | 33.7% | 71.5% |
| 6b | (structure) | 35.6% | 33.8% |
| 6d | (structure) | 0% | ND |
| 6e | (structure) | 63.4% | 96.4% |
| 6f | (structure) | 57.4% | 97.2% |
| 6g | (structure) | 4.5% | ND |

TABLE 2-continued

| Compound | Structure | % Inhibition Coupled | Direct |
|---|---|---|---|
| 6h | 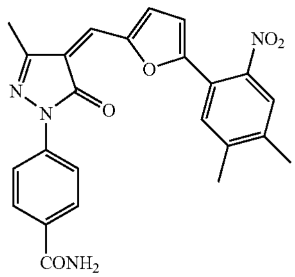 | 40.6% | 94.7% |
| 6i | 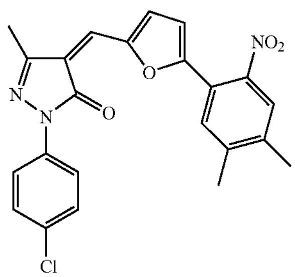 | 13.9% | ND |
| CM-26 | 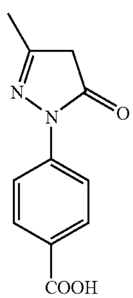 [SMILES: CC1=NN(c2ccc(C(=O)O)cc2)C(=O)C1] | 16.3% | ND |
| 9 | 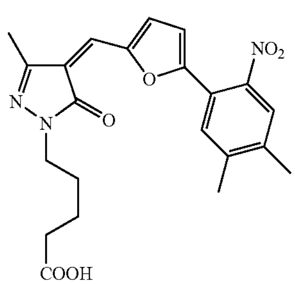 | 92.6% | 55.8% |

Figure 11:
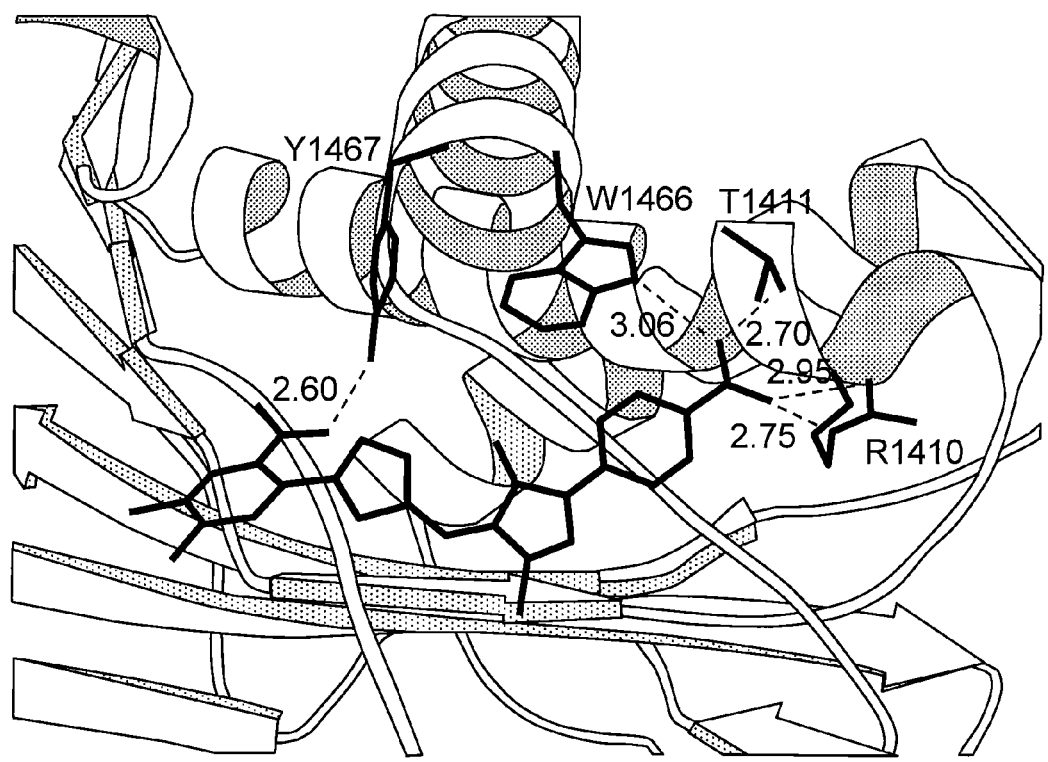
FIG. 11 shows a docking model of compound 7 bound to p300 HAT. Inhibitor 7 is shown as a stick drawing and enzyme residues interacting with inhibitor 7 are indicated.

In accordance with particular embodiments of this invention, the compounds set forth in Table 1 and/or Table are employed as inhibitors of p300/CBP activity. Moreover, analogs, derivatives and salts of the compounds set forth in Tables 1 and 2 are also embraced by this invention. In this regard, the present invention further provides a method for making an inhibitor of p300/CBP. This method involves screening for a compound which interacts with amino acid residues Arg1410, Thr1411, Trp1466, and Tyr1467 of SEQ ID NO:1 or amino acid residues Arg1446, Thr1447, Trp1502 and Tyr1503 of SEQ ID NO:2. As depicted in FIG. 11, the compounds listed in Tables 1 and 2 appear to overlap with acetyl-CoA binding and can thus be used as competitive inhibitors of acetyl-CoA binding. Accordingly, some embodiments embrace compounds of Formula I

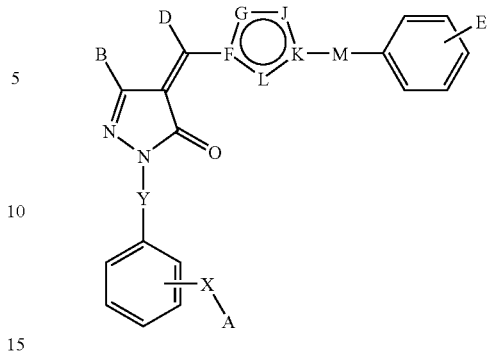

Formula I wherein

A is COOH, CONH$_2$, SO$_3$H, COCH$_2$NH$_2$, COOR, wherein R is CH$_3$, C$_2$H$_5$ or alkyl;

B is CH$_3$, CF$_3$, or halogen;

D is H or CH$_3$;

E is any functional group or halogen;

F, G, J, K, L and M are independently any combination of C, O, S, or N;

X is (CH$_2$)$_n$, wherein n=0 to 6 and said chain can contain heteroatoms (e.g., O, S, or N), or X is CH$_2$—CH=CH—(CH$_2$)$_m$, wherein m is 0 to 2 and the double bond is cis or trans; and Y is C=O or (CH$_2$)$_q$ wherein q=1 to 3.

In certain embodiments of the present invention, an inhibitor of p300/CBP is set forth in Formula II

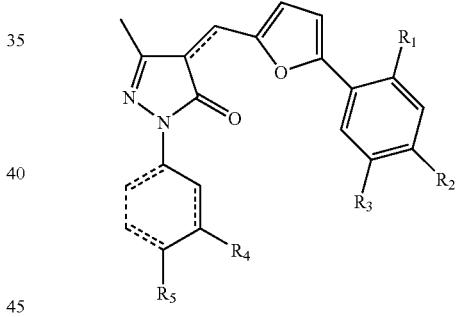

Formula II wherein the dotted lines represent optional bonds,

R$_1$ is H, NO$_2$, or substituted or unsubstituted C$_{1-4}$ alkyl;

R$_2$ and R$_3$ are independently H, CH$_3$, or NO$_2$;

R$_4$ and R$_5$ are independently H, CH$_3$, NO$_2$, SO$_3$H, halogen or substituted or unsubstituted C$_{1-4}$ alkyl;

with the provisio that Formula I does not include a compound wherein R$_1$ is NO$_2$, R$_2$ and R$_3$ are CH$_3$, R$_4$ is H, and R$_5$ COOH; a compound wherein R$_1$ is NO$_2$, R$_2$ is H, R$_3$ are CH$_3$, R$_4$ is H, and R$_5$ COOH; or a compound wherein R$_1$ is COOEt, R$_2$ and R$_3$ are H, R$_4$ is H, and R$_5$ COOH.

As used herein, alkyl groups may be straight or branched chain groups of desirably 1 to 4 carbon atoms. Methyl, ethyl, and propyl including isopropyl are particular suitable alkyl groups in the compounds of the present invention. The alkyl groups of the compounds of the present invention can be substituted by one or more different groups including H, OH, CH$_3$, halogen, and amino groups. The number of substitutions on the alkyl group is restricted only by the number of substitutable positions and by steric constraints.

Halogen atoms in the compounds of the present invention are desirably fluorine, chlorine, bromine or iodine.

To further evaluate the efficacy of a compound identified using the method of the invention, one of skill will appreciate that a model system of any particular disease or disorder involving p300/CBP can be utilized to evaluate the adsorption, distribution, metabolism and excretion of a compound as well as its potential toxicity in acute, sub-chronic and chronic studies.

By way of illustration, Example 12 describes a cell-based assay and animal model systems which can be used to assess the inhibition of tumor cell growth by one or more compounds of the invention. Another useful method for assessing anticancer activities of compounds of the invention involves the multiple-human cancer cell line screening assays run by the National Cancer Institute (see, e.g., Boyd (1989) in *Cancer: Principles and Practice of Oncology Updates*, DeVita et al., eds, pp. 1-12). This screening panel, which involves approximately 60 different human cancer cell lines, is a useful indicator of in vivo antitumor activity for a broad variety of tumor types (Grever, et al. (1992) *Seminars Oncol.* 19:622; Monks, et al. (1991) *Natl. Cancer Inst.* 83:757-766), such as leukemia, non-small cell lung, colon, melanoma, ovarian, renal, prostate, and breast cancers. Antitumor activities can be expressed in terms of $ED_{50}$ (or $GI_{50}$), where $ED_{50}$ is the molar concentration of compound effective to reduce cell growth by 50%. Compounds with lower $ED_{50}$ values tend to have greater anticancer activities than compounds with higher $ED_{50}$ values.

Upon the confirmation of a compound's potential activity in one or more in vitro assays, further evaluation is typically conducted in vivo in laboratory animals, for example, measuring reduction of lung nodule metastases in mice with B16 melanoma (e.g., Schuchter, et al. (1991) *Cancer Res.* 51:682-687). The efficacy of a compound of the invention either alone or as a drug combination chemotherapy can also be evaluated, for example, using the human B-CLL xenograft model in mice (e.g., Mohammad, et al. (1996) *Leukemia* 10:130-137). Such assays typically involve injecting primary tumor cells or a tumor cell line into immune compromised mice (e.g., a SCID mouse or other suitable animal) and allowing the tumor to grow. Mice carrying the tumors are then treated with a compound of the invention and tumor size is measured to follow the effect of the treatment. Alternatively, a compound of the invention is administered prior to injection of tumor cells to evaluate tumor prevention. Ultimately, the safety and efficacy of compounds of the invention are evaluated in human clinical trials.

Compounds which bind to at least one amino acid residue of the L1 loop, electronegative pocket, electronegative groove, Lys-CoA inhibitor binding site or substrate binding site of the HAT domain or p300/CBP can be used in a method for modulating (i.e., blocking or inhibiting, or enhancing or activating) a p300/CBP. Such a method involves contacting a p300/CBP either in vitro or in vivo with an effective amount of a compound that interacts with at least one amino acid residue of the L1 loop, electronegative pocket, electronegative groove, Lys-CoA inhibitor binding site or substrate binding site of the HAT domain or p300/CBP so that the activity of p300/CBP is modulated. An effective amount of an effector or modulatory compound is an amount which reduces or increases the activity of the p300/CBP by 10%, 20%, 30%, 40%, 50%, 60%, 70%, 80%, 90% or 100%. Such activity can be monitored using the methods disclosed herein, by enzymatic assays detecting activity of the p300/CBP, or by monitoring the expression or activity of proteins which are known to be regulated by p300/CBP protein (e.g., p53, NFκB, STAT3, GATA-1, MyoD, TCF, androgen receptor, and HIV Tat).

Given the therapeutic potential of p300/CBP inhibitors in cancer (Iyer, et al. (2004) *Proc. Natl. Acad. Sci. USA* 101:7386-7391; Stimson, et al. (2005) *Mol. Cancer. Ther.* 4:1521-1532; Zheng, et al. (2004) *Methods Enzymol.* 376:188-199), cardiac disease (Davidson, et al. (2005) *Chembiochem.* 6:162-170), diabetes mellitus (Zhou, et al. (2004) *Nat. Med.* 10:633-637), and HIV (Varier & Kundu (2006) *Curr. Pharm. Des.* 12:1975-1993), the structure disclosed herein is useful for designing and screening for more specific compounds based on, e.g., the Lys-CoA scaffold. Of equal importance would be compounds that complement disease-associated mutants (Iyer, et al. (2004) supra) that are associated with p300/CBP HAT inactivation (Qiao, et al. (2006) *Science* 311:1293-1297).

In this regard, one of skill in the art can appreciate that modulating the activity of p300/CBP can be useful in selectively analyzing p300/CBP signaling events in model systems as well as in preventing or treating diseases and disorders involving p300/CBP. The selection of the compound for use in preventing or treating a particular disease or disorder will be dependent upon the particular disease or disorder. For example, a compound which inhibits the activity of p300/CBP will be useful in the prevention or treatment of cancer, cardiac disease, diabetes mellitus, obesity and HIV.

Prevention or treatment typically involves administering to a subject in need of treatment a pharmaceutical composition containing an effective dose of a compound identified in the screening method of the invention. In most cases this will be a human being, but treatment of agricultural animals, e.g., livestock and poultry, and companion animals, e.g., dogs, cats and horses, is expressly covered herein. The selection of the dosage or effective amount of a compound is that which has the desired outcome of preventing, reducing or reversing at least one sign or symptom of the disease or disorder being treated. For example, a subject with cancer (including, e.g., carcinomas, melanomas, sarcomas, lymphomas and leukaemias) can experience unexplained weight loss, fatigue, fever, pain, skin changes, sores that do not heal, thickening or lump in breast or other parts of the body, or a nagging cough or hoarseness, wherein treatment with a compound of the invention can prevent, reduce, or reverse one or more of these symptoms.

Pharmaceutical compositions can be in the form of pharmaceutically acceptable salts and complexes and can be provided in a pharmaceutically acceptable carrier and at an appropriate dose. Such pharmaceutical compositions can be prepared by methods and contain carriers which are well-known in the art. A generally recognized compendium of such methods and ingredients is Remington: The Science and Practice of Pharmacy, Alfonso R. Gennaro, editor, 20th ed. Lippincott Williams & Wilkins: Philadelphia, Pa., 2000. A pharmaceutically-acceptable carrier, composition or vehicle, such as a liquid or solid filler, diluent, excipient, or solvent encapsulating material, is involved in carrying or transporting the subject compound from one organ, or portion of the body, to another organ, or portion of the body. Each carrier must be acceptable in the sense of being compatible with the other ingredients of the formulation and not injurious to the subject being treated.

Examples of materials which can serve as pharmaceutically acceptable carriers include sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; pH buffered solutions; polyesters, polycarbonates and/or polyanhydrides; and other non-toxic compatible substances employed in pharmaceutical formulations. Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

The compositions of the present invention can be administered parenterally (for example, by intravenous, intraperitoneal, subcutaneous or intramuscular injection), topically (including buccal and sublingual), orally, intranasally, intravaginally, or rectally according to standard medical practices.

The selected dosage level will depend upon a variety of factors including the activity of the particular compound of the present invention employed, the route of administration, the time of administration, the rate of excretion or metabolism of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of a compound at levels lower than that required in order to achieve the desired therapeutic effect and gradually increase the dosage until the desired effect is achieved. This is considered to be within the skill of the artisan and one can review the existing literature on a specific compound or similar compounds to determine optimal dosing.

The invention is described in greater detail by the following non-limiting examples.

Example 1

Materials and Methods

Peptide Synthesis. Peptides CMLVELHTQSQDRF (SEQ ID NO:24) for expressed protein ligation and H4-15 (GRGKGGKGLGKGGAK; SEQ ID NO:25) for acetyltransferase assays were prepared using the solid phase peptide synthesis Fmoc strategy. The N-terminal amino group was acetylated for the H4-15 substrate peptide. Peptides were purified (>95% homogeneity) by reversed phase (C-18) high performance liquid chromatography as described previously using a gradient of water-acetontitrile (0.05% trifluoroacetic acid) (Thompson, et al. (2001) supra). Electrospray mass spectrometry of peptides confirmed the correct masses.

Constructs and Semisynthetic p300 HAT. Semisynthetic proteins were prepared and purified following known procedures (Thompson, et al. (2004) supra). Briefly, the truncated p300 HAT domain (amino acid residues 1287-1652) or (amino acid residues 1287-1652 with an internal deletion of amino acid residues 1523-1554) containing an M1652G mutation was inserted into the pTYB2 expression plasmid (New England Biolabs, Ipswich, Mass.). Different point mutations were introduced into the plasmid by site-directed mutagenesis. For protein preparation, the truncated p300 HAT fused to VMA intein-chitin binding domain was expressed in E. coli BL21 (DE3)-RIL cells at 16° C. for 16 hours induced by IPTG (0.5 mM). The cells were harvested and lysed by French press in intein lysis buffer (25 mM HEPES (pH 7.9), 500 mM NaCl, 10% glycerol, 1 mM MgSO$_4$, and 2 mM PMSF). After centrifugation, the supernatant was applied to a chitin column that was extensively washed to remove unbound proteins. The immobilized fusion protein was treated with 200 mM MESNA to generate the thioester and ligated to a synthetic peptide corresponding to amino acid residues 1653-1666 (CMLVELHTQSQDRF; SEQ ID NO:24) over 16 hours at room temperature. The semi-synthetic p300 HAT was then applied to a MONO-S HR5/5 cation exchange column (Amersham Biosciences) for further purification. Following concentration, 10% glycerol was added before flash freezing in liquid N$_2$ and samples were stored at −80° C. Semi-synthetic proteins showed the correct mass as determined by MALDI mass spectrometry.

Crystallization and Structure Determination. To facilitate protein crystallization, the purified p300 HAT was subjected to a 2-step protease treatment. Briefly, concentrated p300 HAT was diluted to 1 mg/ml in a buffer containing phosphate-buffered saline, pH 7.4 and 5 mM dithiothreitol. Fifty μM Lys-CoA was added to the diluted p300 HAT and incubated for 30 minutes. Ten μg/ml trypsin was then added to the protein inhibitor complex at room temperature for 16 hours, and followed by protease treatment with 10 μg/ml carboxypeptidase A and B for another 16 hours. Following protease treatments, two bands corresponding to two protease-resistant p300 N- and C-subdomains were observed on SDS-PAGE gel and were further purified by anion exchange and gel filtration chromatography with MONOQ and SUPERDEX 200a, respectively. The molecular weights of the N- and C-subdomains were assessed to be ~28 kDa and ~11 kDa, respectively, by MALDI-TOF and accurate N-terminal sequences of these two subdomains were obtained by Edman degradation.

The copurified N- and C-subdomains of the p300 HAT domain were concentrated to 12 mg/ml in a buffer containing mM HEPES, pH 7.4, 150 mM sodium chloride and 5 mM dithiothreitol by ultrafiltration for crystallization using hanging-drop vapor-diffusion at room temperature. Initial crystals were obtained by mixing 0.7 μl protein with 0.7 μl reservoir containing 0.1 M HEPES. pH 7.5, 20% w/v polyethylene glycol 4,000 and 10% v/v 2-propanol (Hampton Research, Aliso Viejo, Calif.). Crystals typically appeared in two days but were not easily reproduced and did not grow large enough for diffraction studies. Streak seeding with these initial crystals was necessary to obtain crystals with typical size of 50 μm×50 μm×30 μm. Selenium-derived protein was crystallized under the same conditions as the native protein. Both native and selenium-derived crystals were cryo-protected by transferring them stepwise into a reservoir solution supplemented with 5%, 10% and 15% v/v glycerol respectively, with 500 mM sodium chloride also added into the final cryo-protection solution prior to flash freezing the crystals into liquid propane cooled by liquid nitrogen for data collection. To prepare bromide-derived crystals, native crystals were cryo-protected and frozen as described above, except that sodium chloride was replaced by sodium bromide in the final cryoprotection step and crystals were only soaked for 30-60 seconds prior to freezing them (Dauter, et al. (2000) *Acta Crystallogr. D Biol. Crystallogr.* 56:232-237).

Crystallographic data from both native and derivatized crystals were collected at beamline X6A at the National Synchrotron Light Source (NSLS, Brookhaven National Laboratories). Multiple-wavelength anomalous (MAD) diffraction (Hendrickson & Ogata (1997) *Methods Enzymol.* 276:494-

523) datasets were collected for selenium and bromide-derived crystals and the data was processed and scaled with the HKL2000 suite of programs (Otwinowski & Minor (1997) *Methods Enzymol.* 276:307-326). Due to crystal decay of the bromide-derivatized crystals, only a dataset at the peak wavelength for bromine was useful for phase calculation in single-wavelength anomalous diffraction (SAD). Initial phases was calculated independently for Se-MAD and Br-SAD using the programs SOLVE (Terwilliger & Berendzen (1999) *Acta Crystallogr. D Biol. Crystallogr.* 55:849-861) and SHELX followed by using the AUTOBUILD function in RESOLVE (Terwilliger (2000) *Acta Crystallogr. D Biol. Crystallogr.* 56:965-972; Terwilliger (2003) *Acta Crystallogr. D Biol. Crystallogr.* 59:38-44) and ARP/wARP (Perrakis, et al. (1999) *Nat. Struct. Biol.* 6:458-463) respectively, which resulted in nearly identical models representing 90% of the input protein sequence. A partial model refinement in CNS (Brunger, et al. (1998) *Acta Crystallogr. D Biol. Crystallogr.* 54:905-921) with simulated annealing permitted manual building with the program 0 (Jones, et al. (1991) *Acta Crystallogr.* A 47 (Pt 2):110-119) of additional protein residues that were not present in the initial model. Inspection of Fo-Fc difference Fourier maps at this stage facilitated the unambiguous placement of the Lys-CoA inhibitor employing the HI-CUp server (Kleywegt (2007) *Acta Crystallogr. D Biol. Crystallogr.* 63:94-100). The complete model was further refined using translation, liberation and screw-rotation (TLS) and restrained refinement in REFMAC (inn, et al. (2001) *Acta Crystallogr. D Biol. Crystallogr.* 57:122-13) implemented in CCP4i to a final resolution of 1.7 Å. The final model was checked by PROCHECK (Laskowski, et al. (1993) *J. Appl. Cryst.* 26:283-291) revealing good stereochemical parameters with no residues outside of the allowed regions of the Ramachandran plot.

HAT Assays. HAT activity was determined by either a rapid and nonradioactive HAT assay that measures the production of CoASH by its facile reaction with DTNB, or by a radioactive assay (Lau, et al. (2000) supra; Thompson, et al. (2000) supra). For the DTNB assay, fixed concentrations of acetyl-CoA (2 mM) and the H4-15 peptide (400 μM) were used to measure the $k_{cat}$ and $K_m$ parameters for peptides and acetyl-CoA, respectively. For the radioactive assay, the concentration of [$^{14}$C]acetyl-CoA was fixed at 20 μM when measuring the steady-state kinetic parameters for peptide substrates.

Example 2

Preparation and Crystallization of Semi-Synthetic p300 HAT Domain

Figure 1B:
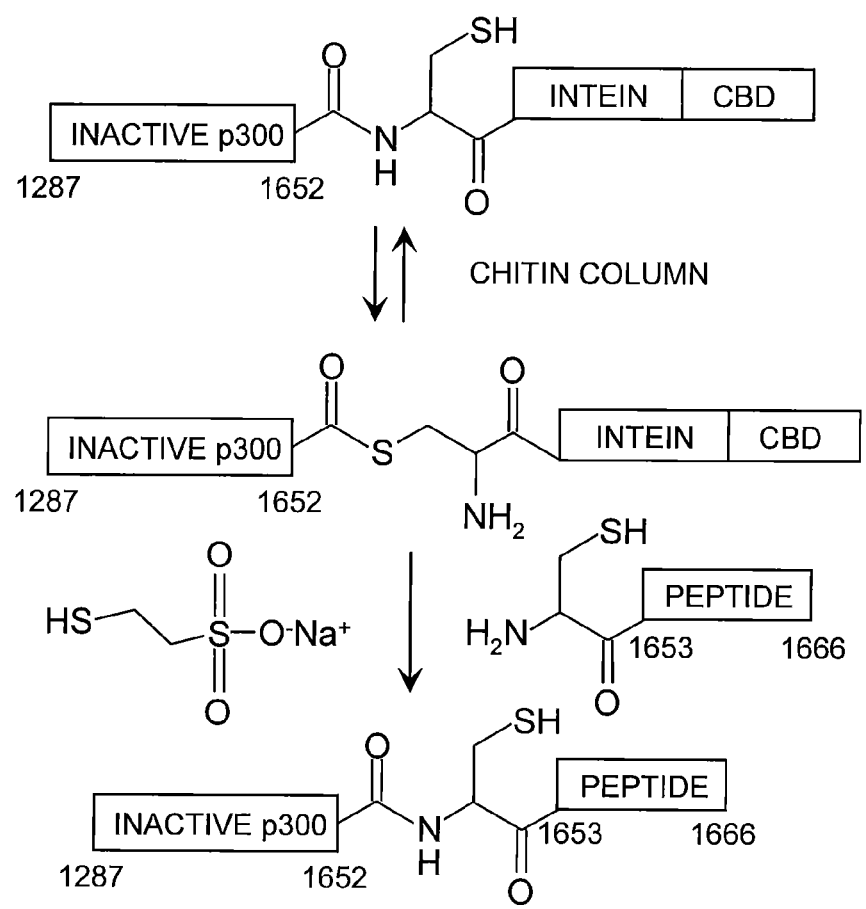
FIG. 1B is a scheme of expressed protein ligation strategy for semi-synthetic p300 HAT domain preparation.

Production of recombinant p300/CBP HAT domain protein in quantities necessary for crystallization is difficult using conventional methods because of toxicity due to aberrant acetylation of host proteins as well as heterogeneous p300 HAT autoacetylation. To overcome these challenges, a semi-synthetic human p300 HAT domain was generated using expressed protein ligation (Thompson, et al. (2004) supra) (FIG. 1B). In this procedure, p300 amino acid residues 1287-1652 were generated, fused to a VMA intein-chitin binding domain, which can be purified on chitin resin, and then converted to a C-terminal thioester by treatment with MESNA. This p300 fragment was soluble but catalytically inactive, and its activity could be recovered by native chemical ligation to N-Cys peptide (residues 1653-1666), which produces active and minimally acetylated semi-synthetic p300 HAT. To further aid in crystallization efforts, 32 residues (1523-1554) of a proteolytically sensitive region were genetically deleted and replaced with a potent lysine autoacetylation site at 1637 with an arginine residue (Thompson, et al. (2004) supra). Although well-behaved by gel filtration, this loop-deleted semi-synthetic p300 HAT failed to crystallize with various ligands tested.

It was contemplated that a residual internal flexible loop was inhibiting crystallization. Therefore, the semi-synthetic p300 HAT was treated with various ratios of trypsin. Two relatively well-defined p300 HAT fragments (about 28 kDa and 11 kDa) were generated when limited proteolysis was performed in the presence of Lys-CoA, whereas protease treatment gave a more complex mixture in the absence of p300 HAT inhibitor. By mass spectrometry and N-terminal sequencing, it was shown that the 28 kDa band corresponded to an N-terminal subdomain (N-subdomain) and that the 11 kDa band corresponded to a C-terminal subdomain (C-subdomain) and that approximately 12 amino acids were removed in addition to the 32 amino acids already genetically deleted (total removal ca. amino acids 1523-1567). The heterodimeric p300 HAT complex was prepared in the presence of Lys-CoA by carrying out an additional proteolysis of the complex with carboxypeptidase A and B and using ion exchange and gel filtration chromatography, which preserved the integrity of the complex, suggesting a stable association and structure.

Purified heterodimeric semi-synthetic p300 HAT-Lys-CoA was crystallized using hanging drop vapor diffusion and streak seeding to obtain crystals of sufficient size (50 μm×50 μm×30 μm) for X-ray data collection. Crystals of the p300 HAT-inhibitor complex formed in spacegroup $P4_3$ with one complex per asymmetric unit cell and the structure was determined by a combination of MAD and SAD using selenomethione and bromine derivatized protein (Table 3).

TABLE 3

| | Data set | | | | |
|---|---|---|---|---|---|
| | | Se-MAD | | Br-SAD | |
| Space group | Peak $P4_3$ | Edge | Remote | Peak $P4_3$ | Native $P4_3$ |
| Unit cell dimensions (Å) | | | | | |
| a | | 61.3 | | 61.4 | 61.5 |
| b | | 61.3 | | 61.4 | 61.5 |
| c | | 101.3 | | 101.0 | 101.2 |
| Wavelength (Å) | 0.9786 | 0.9789 | 0.9287 | 0.9193 | 0.9253 |
| Resolution (Å) | 50-2.0 | 50-2.0 | 50-2.0 | 50-1.8 | 50-1.7 |
| Unique reflections | 25310 | 25331 | 25271 | 34709 | 41358 |

TABLE 3-continued

| | Data set | | | | |
|---|---|---|---|---|---|
| Space group | Peak P4$_3$ | Se-MAD Edge | Remote | Br-SAD Peak P4$_3$ | Native P4$_3$ |
| Completeness (%)[a] | 99.9 (100.0) | 99.9 (100.0) | 99.9 (100.0) | 100.0 (100.0) | 99.9 (100.0) |
| Multiplicity | 6.3 | 6.3 | 6.3 | 6.4 | 5.6 |
| I/σ | 18.4 (2.4) | 18.8 (2.4) | 21.3 (2.2) | 29.2 (3.5) | 33.5 (2.6) |
| R$_{merge}$ (%)[b] | 8.6 (71.9) | 8.4 (76.8) | 8.3 (81.2) | 5.6 (50.9) | 4.4 (65.8) |
| Number of sites | | 6 | | 28 | |
| FOM/CC | | 0.51 | | 0.33 | |
| Resolution range | | | 50-1.7 | | |
| R$_{cryst}$ (%)[c] | | | 22.1 | | |
| R$_{free}$ (%)[d] | | | 18.2 | | |
| Number of atoms | | | | | |
| Protein | | | 2596 | | |
| Lys-CoA | | | 64 | | |
| Water | | | 299 | | |
| Average B-factors (Å$^2$) | | | | | |
| Protein | | | 25.3 | | |
| Lys-CoA | | | 22.5 | | |
| Water | | | 35.1 | | |
| Root mean square deviations | | | | | |
| Bond length (Å) | | | 0.011 | | |
| Bond angle (°) | | | 1.466 | | |

[a] Values in parentheses are from the highest resolution shell.
[b] R$_{merge}$ = Σ||I − <I>|/Σ<I>
[c] R$_{cryst}$ = Σ||F$_o$| − |F$_c$||/Σ|F$_o$|
[d] R$_{free}$ = Σ$_T$||F$_o$| − |F$_c$||/Σ$_T$|F$_o$| (where T is a test data set of 5% of the total reflections randomly chosen and set aside before refinement).

Example 3

Overall Structure of the p300 HAT-Inhibitor Complex

Figure 8A:
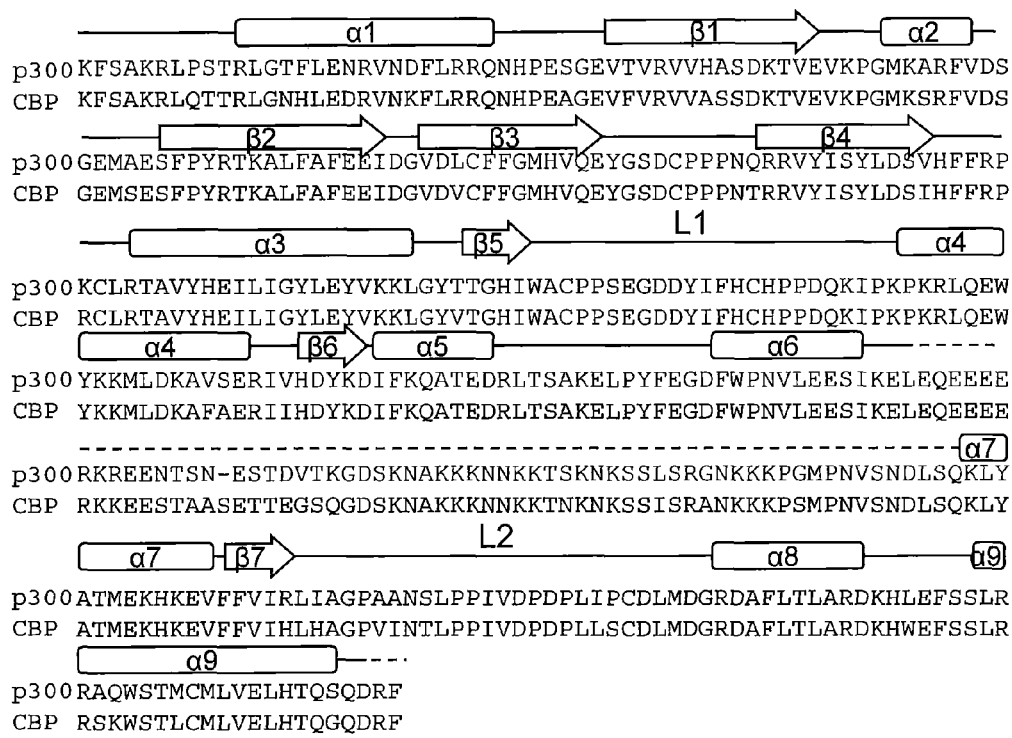
FIG. 8 shows the amino acid sequences of human p300 and human CBP. An overall structure and amino acid sequence comparison of the human p300 (SEQ ID NO:22) and human CBP (SEQ ID NO:23) HAT domain are shown.

The overall fold of the p300 HAT domain includes a central β-sheet composed of 7 β-strands surrounded by 9 α-helices and several loops, with the last 3 α-helices and the last β-strand coming from the C-subdomain (FIG. 8). The smaller C-subdomain spans the entire structure by capping opposite ends of the larger N-subdomain with secondary structural elements that are connected by a long loop (L2) that tracks along the "bottom" side of the N-subdomain. This intimate association of the N- and C-subdomains is consistent with their protease resistance and tight heteromeric association during purification and crystallization. Within the central β-sheet the β7-strand from the C-subdomain is intercalated between the β5 and β6 strands of the N-subdomain, contributing to the integral association between the two subdomains. On the "top" surface and at one end of the β-sheet, the α2, α5 and α6 helices from the N-subdomain and the α7 helix and a loop region from the C-subdomain form a local hydrophobic core that appears to provide a structurally stable scaffold for the cleaved autoacetylation loop that connects the α6 and α7 helices of the N- and C-subdomains, respectively, of the native protein. In the presence of the Lys-CoA inhibitor, this autoacetylation loop is presumably flexible and susceptible to protease cleavage. Helices α8 and α9 from the C-subdomain also sit on the "top" of the central β-sheet and cap the other end of the β-sheet. Helices α1, α3 and α4 of the N-subdomain line the "bottom" surface of the central β-sheet and make extensive interactions with the sheet. There are two unusually long loops in the structure that are referred to herein as L1 and L2. The L2 loop from the C-subdomain connects the β7 strand and α8 helix of the C-subdomain and spans the underside of the central β-sheet while the L1 loop is intimately associated with Lys-CoA inhibitor binding. Specifically, the Lys-CoA inhibitor binds to one edge of the β-sheet with the α3 helix and β4-strand on one side and the α4 helix and β5-strand on the opposite side. The L1 loop covers what would otherwise be the solvent exposed surface of the Lys-CoA inhibitor.

As described, deletion of residues 1653-1666 leads to loss of catalytic activity. The semi-synthetic ligation junction occurs in the middle of the C-terminal α9 helix and loss of this helix would presumably have ramifications for the integrity of the overall structure. It is however, noteworthy, that circular dichroism studies suggest that the catalytically defective, C-terminally truncated p300 HAT domain does not contain a significantly perturbed HAT domain fold (Karanam, et al. (2006) *J. Biol. Chem.* 281:40292-40301).

Example 4

Comparison of p300 with Other HATS

A comparison of the p300 HAT domain with other HAT structures (Marmorstein (2001) *J. Mol. Biol.* 311:433-444) shows several differences and some similarities, despite the absence of detectable sequence conservation with other HATs. Specifically, an overlay of the p300 HAT domain with the HAT domains from yeast Gcn5, a member of the GCN5/PCAF family of HATs, and from yeast Esa1, a member of the MYST family of HATs, shows structural conservation within the central core region associated with acetyl-CoA cofactor binding. This structural homology corresponds to the A, B and D sequence motifs of the GNAT (Gcn5-related histone N-acetyltransferases) homology reported by Neuwald and Landsman (Neuwald and Landsman (1997) supra). Specifically, β-strands β1-β4, and α helices α3 and α4, show significant structural alignment within all three proteins, while β-strands β5 and β7 show additional structural alignment with Gcn5. In addition, like the Gcn5 and Esa1 HAT domains, p300 contains secondary structural elements that flank the central core acetyl-CoA binding region and appear to form the substrate binding cleft, as has been shown to be the case for the Gcn5 HAT, however, these regions structurally diverge among the three HAT domains.

Other aspects of the p300 HAT domain are very different from other HATs. In particular, the unusually long L1 loop that connects β5 and α4 and that appears to encapsulate the Lys-CoA inhibitor is a unique feature of the p300 HAT domain. Indeed, the L1 loop contributes about 30% of the total buried solvent accessible surface of 1225 Å$^2$ of the CoA portion of Lys-CoA. The tip of the L1 loop also appears to be in position to influence protein substrate binding in a way that is distinct from other HATs. Indeed, the L1 loop buries 266 Å$^2$ of the lysine portion of the Lys-CoA inhibitor. In addition, comparison of the electrostatic surface potential of the substrate binding surfaces of the HAT domains of Gcn5, Esa1 and p300 shows significant divergence. While Gcn5 and Esa1 show deeper and more apolar substrate binding pockets, the p300 HAT domain reveals a shallow and highly acidic site consistent with the different substrate binding properties of p300 relative to other HATs.

Example 5

Structure-Guided Mutagenesis and Functional Characterization

Figure 2:
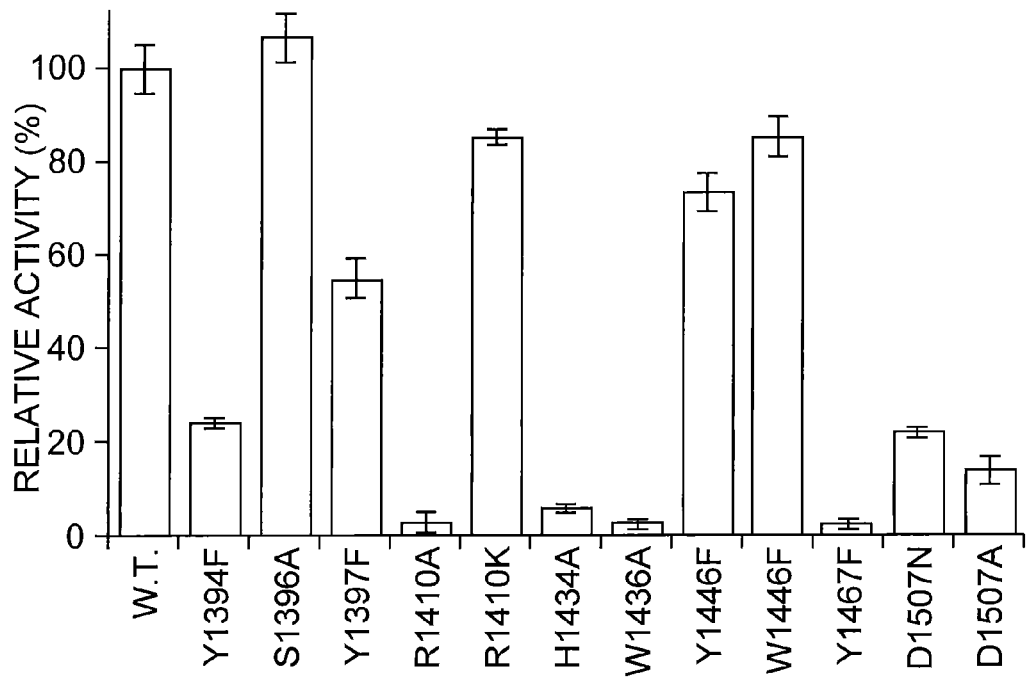
FIG. 2 shows the relative activity of several mutants around the p300 HAT domain active site as inferred from the structure. The activity was measured using 50 nM enzyme, 20 µM AcCoA and 200 µM H4-15 for most of the mutants. W1436A, H1434A activity was measured using 50 nM enzyme, 200 µM AcCoA and 200 µM H4-15. Sub-saturating concentrations of AcCoA and H4-15 were used to more easily detect the difference between wild-type p300 and mutants resulting from $K_m$ changes. Wild-type (W.T.) p300 activity was measured under each condition to normalize the relative activity of the mutants.

The p300 HAT/Lys-CoA complex structure indicates a variety of residues that may be involved in substrate binding or catalysis. Catalytic residues include four tyrosines: Tyr1394, Tyr1397, Tyr1446, and Tyr1467 within about 3-8 Å of the Lys-CoA bridging acetyl carbonyl group. His 1434, Ser1396 and Trp1436 are also proximal to the active site. Interestingly, among them, the Tyr1394 side-chain phenol makes a hydrogen bond with Asp1507, and Tyr1467 makes a hydrogen bond with the Lys-CoA sulfur atom. Residues that appear particularly critical for substrate binding include Arg1410 and Trp1466 that mediate CoA interactions in the structure. A shallow pocket proximal to the lysine moiety of the Lys-CoA inhibitor also indicates that the polar residue Thr1357 and the acidic residues Glu1505, Asp1625 and Asp1628 may play a role in binding to the basic protein substrates of p300. In addition, several cancer-associated amino-acid substitution mutants including Ser1650, Asp1399, and Arg1342 were analyzed. In general, amino acid substitutions of putative catalytic residues involved conservative changes while other residues were substituted with alanines or charge reversal mutants. FIG. 2 shows a comparison of the catalytic activity of several amino acid substitution mutants of putative catalytic and CoA-binding residues. A more comprehensive analysis of amino acid substitution mutants including those mentioned above are described in the subsequent sections.

The L1 Substrate Binding Loop and Inhibitor Recognition.

The L1 loop is involved in the binding of both the acetyl-CoA and lysine moieties of the Lys-CoA inhibitor (FIG. 3). This region of the p300 HAT domain is therefore also referred to herein as the L1 substrate binding loop.

This substrate binding loop L1 adopts an ordered conformation without secondary structure, largely due to the presence of six prolines out of the 25 residues within this loop. While the extended regions of the L1 loop sits over the CoA portion of the Lys-CoA inhibitor, hydrophobic residues within the tip, or turn region, sit within a local hydrophobic pocket that is formed by apolar residues from both N- and C-subdomains. In particular, Ile1447 and Phe1448 from the L1 loop interact with residues from the α8, α9 and central β-sheet residues: Phe1361, Val1401, Phe1630, Phe1641 and to a lesser extent with non-polar regions of His1377, Tyr1397 and Arg1627. In addition, the side chains of Asp1445, His1451 and main chains of Ile1447, Phe1448 from the L1 loop form a specific hydrogen bonding network with the side chain of Asp1399 and the main chain of Ser1400 from β4. Together the L1 substrate binding loop is intimately associated with both the rest of the protein and the Lys-CoA inhibitor consistent with its resistance to proteolysis.

The Lys-CoA inhibitor binds against one edge of the central β-sheet and is flanked on the opposite site by the L1 loop. The edges of the α3 helix/β4-strand and α4 helix/β5-strand flank the two other sides that together with the central β-sheet and L1 loop surround the inhibitor within a tunnel.

The CoA portion of the Lys-CoA makes extensive interactions with the p300 HAT domain (FIG. 3). Specifically, the middle portion of the pantetheine arm of the Lys-CoA inhibitor is almost completely buried by predominantly van der Waals interactions with residues from the L1 loop, α4 and β4, and the pantetheine phosphate and 3' phosphate oxygens make several direct and water-mediated hydrogen bond interactions from residues in the β4 strand and with the guanidinium side chain of Arg1410 from α3. As discussed, Lys-CoA is unusual in requiring its 3'-phosphate for high affinity interaction with p300 (Cebrat, et al. (2003) supra). In this regard, Arg1410 appears to make three hydrogen bonds with phosphates of the Lys-CoA molecule, with one involving a water-mediated and a direct hydrogen bond to the 3'-phosphate and the other being a direct hydrogen bond to the pantetheine phosphate. The importance of Arg1410 was examined by replacing it with Lys and Ala. As shown in FIG. 2 and Table 4, R1410A leads to a 15-fold increase in the $K_m$ of acetyl-CoA, but has essentially the same $K_m$ for peptide substrate compared with the wild-type p300 HAT. Unexpectedly, R1410K p300 HAT behaves much more similarly to wild-type p300 HAT, providing a strong evidence for a critical electrostatic contribution of Arg1410. In addition, the pantetheine phosphate group of Lys-CoA makes hydrogen bonds with the hydroxyl group side chain of Thr1411 and the indole ring of the Trp1466 side chain of α3 and α4, respectively, and Trp1466 also contributes hydrophobic contacts to the pantetheine arm of the CoA moiety. The modest effect on catalysis of the W1466F mutant reveals that the Trp1466-mediated hydrogen bond is unlikely to be very important for catalysis (FIG. 2); however the hydrophobic effect mediated by the Trp1466 sidechain may be nicely captured by a Phe replacement. The adenosine ring of the CoA moiety is also stabilized by a noncanonical cation-π interaction with Arg1462 from α4 and by a conventional hydrogen bond with the main chain oxygen of Ile1457 from the C-terminal end of the L1 loop.

TABLE 4

| Enzyme | $K_m(\mu M)$ for H4-15 | $K_m(\mu M)$ for AcCoA | $k_{cat}(s^{-1})$ | V/K $(M^{-1}s^{-1})$[†] | Structural basis for the mutant residue |
|---|---|---|---|---|---|
| W.T. | 164 ± 10 | 40 ± 6 | 4.1 ± 0.1 | 25,000 ± 1643 | |
| Y1467F | 520 ± 30 | 17 ± 2 | 0.030 ± 0.001 | 58 ± 4 | H-bond with Sulfur and may protonate AcCoA leaving group |
| Y1394F | 136 ± 30 | 47 ± 9 | 0.47 ± 0.04 | 3456 ± 830 | Proton relay |
| W1436A | 394 ± 40 | 20 ± 3 | 0.19 ± 0.01 | 482 ± 60 | Hydrophobic interaction for Lys-CoA |
| H1434A | 151 ± 10 | 88 ± 4 | 0.59 ± 0.02 | 3910 ± 290 | Proton replay |
| R1410A | 190 ± 40 | 657 ± 90 | 1.2 ± 0.1 | 6263 ± 1300 | H-bond with 3' and pantetheine phosphate |
| R1410K | 156 ± 40 | 74 ± 6 | 1.4 ± 0.1 | 8718 ± 2200 | |
| D1625R | 640 ± 70 | NM[‡] | 3.6 ± 0.2 | 5668 ± 690 | Contribute to the negative surface of the peptide binding site |
| D1628R | >1000 | NM[‡] | UD* | ~2100** ± 90 | |
| E1505R | >1000 | NM[‡] | UD* | ~2000** ± 40 | |
| T1357R | 294 ± 50 | NM[‡] | 3.9 ± 0.3 | 13163 ± 2491 | Located at the peptide binding site |
| T1357L | 111 ± 20 | NM[‡] | 2.1 ± 0.1 | 18739 ± 3550 | |
| D1625R/D1628R | >1000 | 40 ± 7 | UD* | ~1162** ± 60 | Double mutant |
| E1625R/D1625R/D1628R | >1000 | 461 ± 40 | UD* | ~232** ± 10 | Triple mutant |

*UD: Undetectable.
[‡]NM: Not measured.
[†]V/K was calculated using peptide $K_m$.
**V/K was calculated using a linear fit.

The lysine component of the Lys-CoA inhibitor also makes extensive interactions with the p300 HAT domain. Specifically, the ε nitrogen atom makes a hydrogen bond with the main chain oxygen of Trp1436. The amine group that caps the carboxyl end of the lysine backbone, presumably mimicking the backbone position of the Lys-1 amino acid, forms a hydrogen bond with the hydroxyl group of Tyr1397. Three hydrophobic residues, Tyr1397 from β4, and Trp1436 and Tyr1446 from the L1 loop together with Cys1438 also from the L1 loop form a hydrophobic subtunnel that interacts with the aliphatic portion of the lysine side chain.

Substrate Binding.

In addition to the pocket that accommodates the lysine moiety of Lys-CoA, presumably mimicking the lysine side chain from native protein substrates, a second pronounced and highly electronegative pocket is present about 10 Å away from the substrate lysine. Because p300 substrates show a strong preference for the presence of a Lys or Arg side-chain two to three residues downstream or upstream of the primary acetylation site (Thompson, et al. (2001) supra) (FIG. 4), the possibility that this region might be important for the binding of protein substrates was considered. Consistent with this possibility is the presence of a narrow, shallow and electronegative groove connecting the two pockets. The wall of one side of the groove is composed of Ser1396 and Tyr1397. The negative potential of the second pocket is largely formed by the side chain atoms of residues Thr1357, Glu1505, Asp1625, and Asp1628. To examine if these regions are important for substrate binding, single, double, triple and quadruple amino acid mutagenesis experiments were carried out on the mentioned residues. These mutations were designed to (1) either occlude or change the charge state of the groove or the first pocket, (2) fill the cavity or reverse the negative charge of the second pocket.

Figures 4, 5:
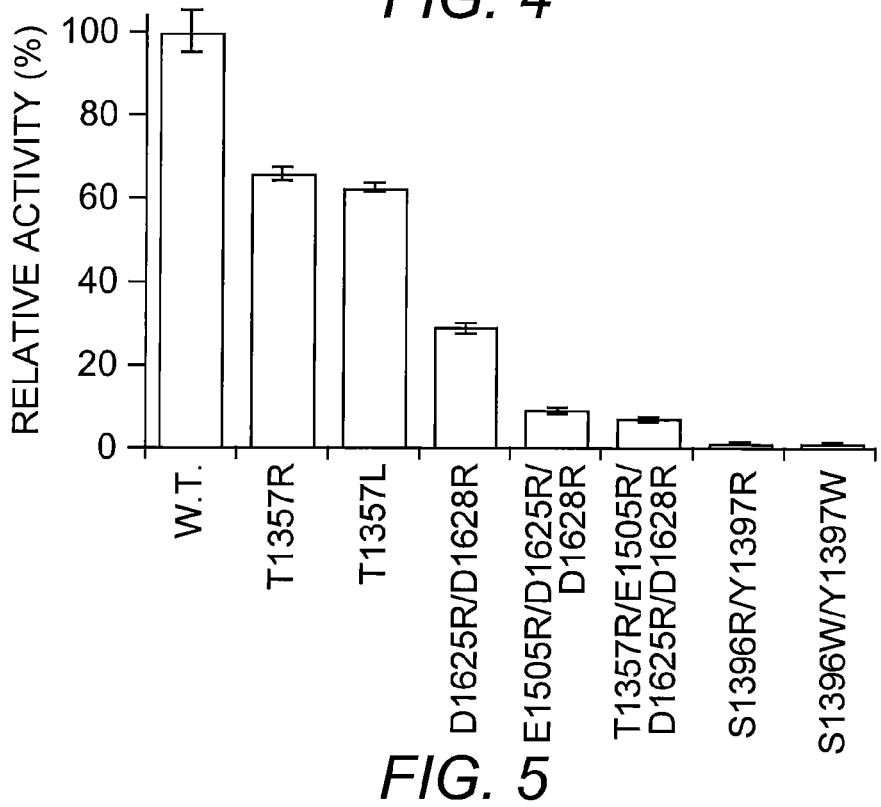
FIG. 4 shows the sequence alignments of histone (H2A, SEQ ID NO:3; $H_2B$, SEQ ID NO:4; H3, SEQ ID NO:5; and H4, SEQ ID NO:6) and non-histone (p53, SEQ ID NO:7; p73, SEQ ID NO:8; HMG14, SEQ ID NO:9; E2F1, SEQ ID NO:10; dTCF, SEQ ID NO:11; HMGI(Y), SEQ ID NO:12; ATF-2, SEQ ID NO:13; c-Myb, SEQ ID NO:14; NFκB, SEQ ID NO:15; STAT3, SEQ ID NO:16; mGATA-1, SEQ ID NO:17; MyoD, SEQ ID NO:18; AR, SEQ ID NO:19; Tat, SEQ ID NO:20; p300, SEQ ID NO:21) p300 substrates with all positively charged residues are underlined. The preferred acetylation sites are indicated by the box and the proximal lysine or arginine residues are marked with a star.
FIG. 5 depicts the results of a mutagenesis study showing the relative activity of several putative substrate binding mutants. The activity was measure using 50 nM enzyme, 200 µM AcCoA and 200 µM H4-15; and is plotted as activity relative to wild-type (W.T.) p300.

For the first strategy, since it was shown that S1396A does not decrease activity (FIG. 2), S1396R/Y1397R and S1396R/Y1397R double mutants of p300 HAT were generated to perturb the groove. Both mutants showed severely decreased p300 HAT activity (>50-fold), indicating the importance of the groove for peptide substrate binding (FIG. 5). For the second strategy, the T1357L replacements lead to rather modest V/K effects (Table 4), indicating that the second pocket may not be deeply engaged by peptide substrate residues. For charge reversal mutagenesis analysis, the single mutant D1625R showed an increased peptide substrate $K_m$ and a V/K decrease of about 5-fold, while D1628R and E1505R mutant proteins displayed more pronounced effects; V/K was decreased by 12-fold and the $K_m$ for the H4-15 peptide substrate was too high to measure (FIG. 5 and Table 4). The double, triple, and quadruple mutations showed partially additive effects (FIG. 5 and Table 4). The D1625R/D1628R double mutant protein showed a 20-fold drop in V/K whereas the $K_m$ of acetyl-CoA was unchanged compared to that of wild-type p300 HAT. The E1505R/D1625R/D1628R triple mutant displayed a more dramatic V/K reduction; however, the acetyl-CoA $K_m$ for this triple mutant was also elevated, indicating slight structural perturbation (FIG. 5 and Table 4). Thus, the D1625R/D1628R p300 HAT mutant was selected for further analysis of substrate residue preferences.

To test the influence of electrostatic interactions on substrate sequence selection, the steady state kinetic parameters for several synthetic H4 tail peptide analogs was determined (listed in Table 5). In H4-15, there are two other basic residues (Lys5 and Lys12) near the target Lys8. It has previously been shown that either one of the nearby Lys (or Arg replacements) is sufficient to permit efficient acetylation by full-length p300 (Thompson, et al. (2001) supra). Here, the effects of replacing Lys5 and Lys12 with Ala, the neutral residue hydrogen bonding citrulline, or Asp were compared for wild-type and mutant p300 HAT as indicated in Table 5. Analysis of the single lysine substrate, analogous to the Lys-CoA component, which contains both amino and carboxyl groups derivatized as amides (Table 5), was also conducted. $K_m$ of these substrates were generally too high to be measured (>1000 μM) under the experimental conditions, highlighting the important role of the nearby positively charged residues for substrate interaction. As shown Table 5, the 22-fold V/K difference between wild-type p300 HAT protein and the D1625R/D1628R mutant for H4-15 substrate dropped to 6-fold when using Ac-Lys-NH2 as substrate. The smaller V/K drop in activity with Ac-Lys-NH2 substrate indicates that a key role of Asp1625 and Asp1628 is to assist in recruiting the basic residues of H4-15 by electrostatic interaction. Consistent with this idea, H4-12$^{K5A/K12A}$ or H4-12$^{K5Cit/K12A}$ which lack proximal basic residues but contain neutral hydrogen bonding residues show kinetic behavior similar to that of Ac-Lys-NH2 (Table 5). However, with H4-15$^{K5D/K12D}$ as substrate, wild-type and D1625R/D1628R p300 HAT displayed almost equal (within 2-fold) acetyltransferase activity. Taken together, these data indicate that the second highly electronegative pocket binds to the proximal basic residue (Lys or Arg) and facilitates the acetyltransferase reaction. However, the loss of 6-fold in V/K for neutral H4 substrates H4-12$^{K5A/K12A}$ or H4-12$^{K5Cit/K12A}$ or Ac-Lys-NH2 indicates that the double mutant may also interfere with the overall surface charge of the nearby first pocket as well.

erodimeric stability through two chromatographic separations, its similarity in CoA binding to other acetyltransferases, and by site-directed mutagenesis of key active site residues contributing to turnover. The X-ray structure shows a number of potential nucleophilic residues (Ser/His/Tyr) in proximity to the predicted position of the acetyl-CoA carbonyl carbon but mutagenesis of any of these residues fails to fully abolish catalytic activity, as would be predicted for an obligate catalytic intermediate. Moreover, it has been demonstrated with acetyl-coenzyme A affinity labeling-based reagents that these do not target any critical residue for catalysis. Given the high affinity of the partial bisubstrate analog Lys-CoA for p300 HAT, it is contemplated that the protein conformation captured in the structure corresponds to a catalytic state indicating direct passage of the acetyl group from acetyl-CoA to the substrate lysine.

It is unclear why bisubstrate analogs with longer peptide moieties are weaker binders. For example, H4-CoA-20, a bisubstrate analog composed of 20 residues of the histone H4 tail, inhibits p300 more than 20-fold more weakly than Lys-CoA (Lau, et al. (2000) supra) In contrast, based on studies herein and previously (Thompson, et al. (2001) supra), the histone H4 tail peptide H4-20 is indeed processed at least 15-fold faster than Ac-Lys-NH2 (Table 5). If a classical ternary complex mechanism were operative, then more authentic bisubstrate analogs would be expected to bind to p300 more tightly than the primitive Lys-CoA analog, as occurs with PCAF/GCN5. It is believed that a "hit-and-run" or Theo-

| Peptide | Peptide Sequence | SEQ ID NO: | V/K($M^{-1}s^{-1}$) for W.T. | V/K($M^{-1}s^{-1}$) for D1625R/D1628R |
|---|---|---|---|---|
| H4-15 | GRGKGGKGLGKGGAK | 25 | 25000 ± 1643 | 1162 ± 60 |
| H4-15(K5D/K12D) | GRGDGGKGLGDGGAK | 26 | 636 ± 40 | 422 ± 20 |
| H4-12(K5A/K12A) | RGAGGKGLGAGA | 27 | 3824 ± 180 | 515 ± 15 |
| H4-12(K5X/K12A) | RGXGGKGLGAGA* | 28 | 5247 ± 260 | 738 ± 20 |
| Ac-Lys-NH$_2$ | CH$_3$CO-NH-Lys-CONH$_2$ | – | 1843 ± 50 | 326 ± 10 |

*X = citrulline

Autoinhibition.

Although the lysine-rich autoacetylation loop of the p300 HAT domain is not present in the structure disclosed herein, it is contemplated that it may fold back in cis onto the highly electronegative surface of the p300 HAT domain that is proximal to the lysine binding site. Such a nonspecific electrostatic interaction is probably strong enough to prevent the binding of other substrates until intermolecular autoacetylation of the loop occurs. Autoacetylation of multiple sites within the loop, which is known to occur, may function to neutralize the lysine-rich loop such that protein substrates may compete with it for binding to p300. Though most of the acetylated lysine residues were genetically or proteolytically removed, there were some acetylated lysines (Lys1336, Lys1499, Lys1473, Lys1637) that remained (Thompson, et al. (2004) supra). These lysine residues are all located at the surface, which supports an intermolecular autoacetylation model (Karanam, et al. (2006) supra).

Catalytic Mechanism.

Figure 6A:
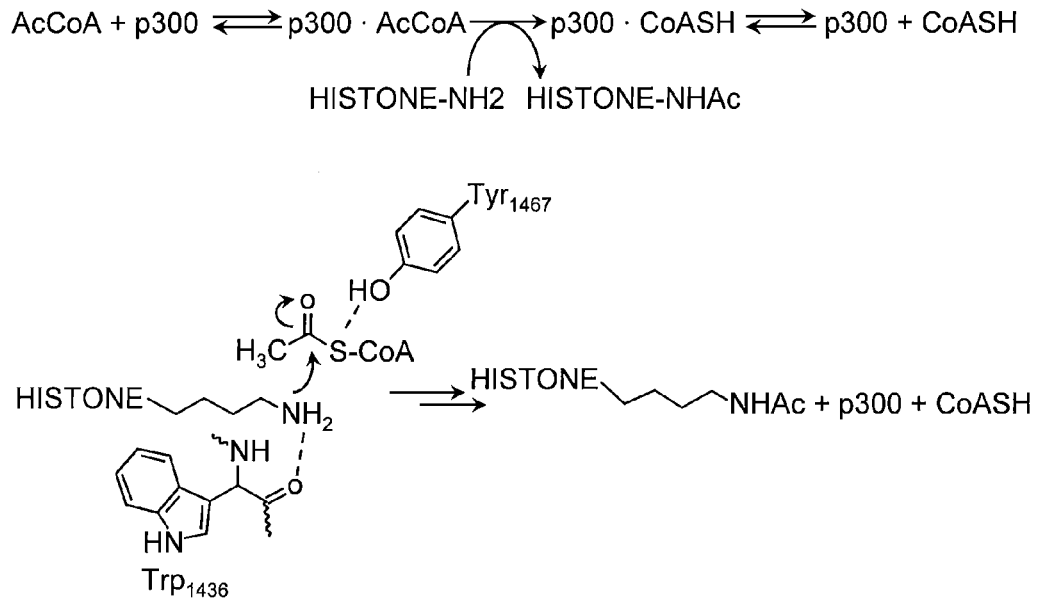
FIG. 6A is a schematic of the catalytic mechanism of p300/CBP.

As discussed, studies on the p300 histone acetyltransferase reaction show conflicting evidence regarding the potential of an acetylated covalent intermediate. The catalytic relevance of the heterodimeric structure here is indicated by the hetrell-Chance (T.-C.) acetyl transfer mechanism (Segel (1975) *Enzyme Kinetics*) could account for such behavior. In the T.-C. mechanism, there is no stable ternary complex as formed in standard sequential mechanisms (FIG. 6A). Rather, after the acetyl-CoA binds, the peptide substrate associates weakly with the p300 surface allowing the lysyl residue to snake through the p300 tunnel and react with the acetyl carbon. It is contemplated that a conformational change is associated with acetyl transfer and that this post-reaction state is captured in the structure disclosed herein. This post-reaction conformation further weakens peptide-enzyme interactions, somewhat analogous to, but more extreme than a loop displacement model suggested for PCAF/GCN5 (Poux, et al. (2002) supra; Zheng, et al. (2005b) *Biochemistry* 44:10501-10509). Thus, the "partial" bisubstrate analog Lys-CoA rather than the apparently more complete structure H4-CoA-20 is a more faithful mimic of the T.-C. reaction coordinate of p300, and the X-ray structure captures this reactive state. It is noted, however, that the parallel line pattern previously observed in a steady-state two substrate kinetic analysis of p300 (Thompson, et al. (2001) supra) is not inconsistent with a T.-C. mechanism since the acyl transfer from a thioester to an amine is effectively irreversible thermodynamically.

The precise role of various residues in facilitating the chemistry of acetyl transfer is indicated by mutagenesis and the observed structure. Steady-state kinetic analysis of Y1394F p300 HAT showed that the loss in acetyltransferase activity for this mutant was due to a decrease in $k_{cat}$ with insignificant $K_m$ effects. His1434A showed a 7-fold lower $k_{cat}$ compared with that of wild-type p300 HAT. W1436A was 50-fold slower and Y1467F was more than 400-fold slower than wild-type p300 HAT. Most of the reduction was due to a drop in $k_{cat}$, indicating an important effect on the chemical step in acetyl transfer. The most critical residue is Tyr1467 (Table 4). Mutation of Tyr1467 results in a 430-fold reduction in V/K. This residue forms a direct hydrogen bond to the sulfur atom of Lys-CoA and is predicted to play a key orienting role as well as general acid function in protonating the leaving group. It is noteworthy that Y1467F showed a mildly depressed acetyl-CoA $K_m$ relative to wild-type. This indicates that ground state hydrogen bonding energy between the Tyr phenol group and the acetyl-CoA sulfur was modest and a source of strain, characteristic of a form of enzymatic rate enhancement known as ground-state destabilization (Scheibner, et al. (2002) *J. Biol. Chem.* 277:18118-18126). A related role for a Tyr has not been observed in other HATs but has been noted in serotonin N-acetyltransferase (Scheibner, et al. (2002) supra).

Figure 6B:
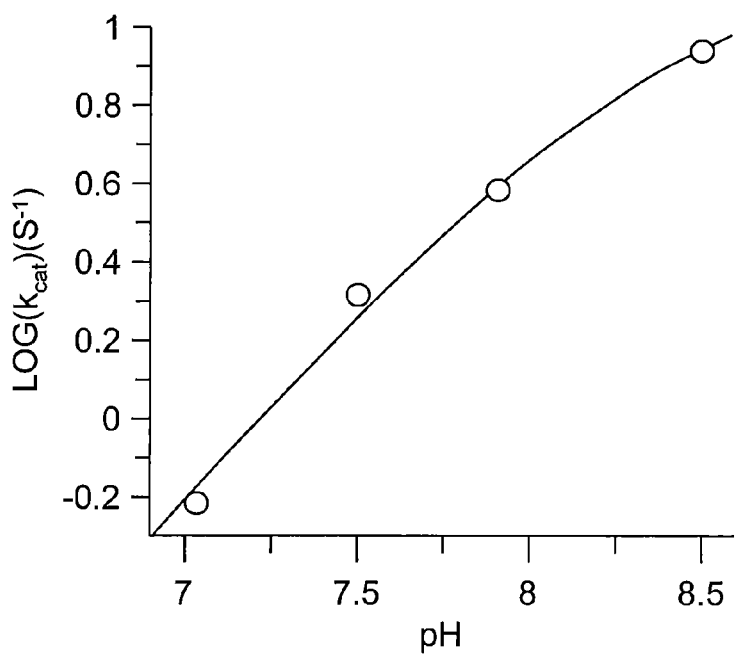
FIG. 6B is a pH-rate profile of wild-type p300. The pka is at 8.36±0.14. The pH-rate profiles of Y1467F, Y1394F and H1434A were also measured and were found to not be significantly different from that of wild-type p300.

A second key residue is Trp1436. Mutation of Trp1436 into Ala reduced $k_{cat}/K_m$ by 50-fold (Table 4). The Trp1436 indole side-chain appears to play a key role in guiding the Lys side chain into attacking acetyl-CoA by van der Waals contact. By contributing to the hydrophobic environment (formed by Tyr1397, Ty1446, Cys1438 and Trp1436) in the active site, it also likely helps reduce the Lys $pK_a$ below its native level of 10. This would serve to enhance catalysis by biasing the substrate Lys to the neutral amine which is necessary for attack. Although the backbone carbonyl of Trp1436 makes an H-bond with the s-amino hydrogen of Lys-CoA, there is no obvious catalytic base in contrast to other HATs which are believed to require acidic residues playing this role. However, as discussed with serotonin N-acetyltransferase, the spontaneous reaction between a neutral amine and thioester is predicted to be very fast once the enzyme can template their association in correct orientation (Scheibner, et al. (2002) supra; Zheng, et al. (2004) *Methods Enzymol.* 376:188-199). Roles for polar residues for guiding the protons out of the active site are indicated for His1434 and Tyr1394 and/or Asp1507 which contribute modestly to catalysis (Table 4). An analysis of pH-rate profiles in the wild-type reaction (FIG. 6B) and selected mutants (data not shown) fails to account for the important $pK_a$ of 8.5 which we speculate may be the substrate Lys epsilon-amine group. Based on the discussion above, a catalytic mechanism is illustrated in FIG. 6A.

Disease Mutations.

Figure 7:
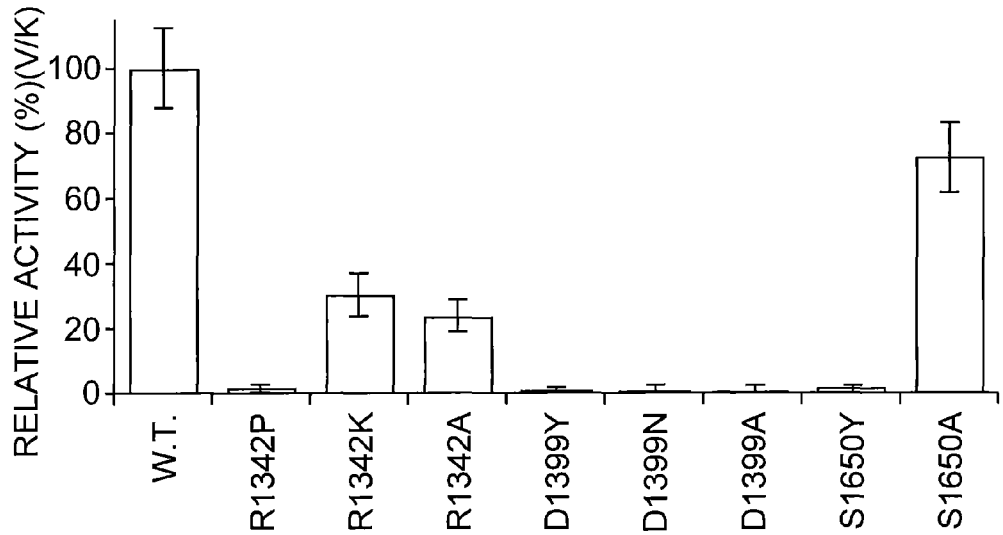
FIG. 7 depicts the results of a mutagenesis study showing the relative activity of cancer associated mutants. p300 wt and disease mutants for these studies do not contain the internal deletion of residues 1523-1554 used for the structural studies; however, they were allowed to activate by pre-incubation with acetyl-CoA. V/K is the $V_{max}/K_{m\ (H4-15)}$. D1399Y, R1342P steady state assays were carried out using a radioactive assay because of their low activity with 20 µM AcCoA. All the other mutants were evaluated using a nonradioactive HAT assay with 2 mM AcCoA.

The structure of p300 HAT permits a more detailed understanding of the enzymologic mutations that have been observed in a number of human disease states. There are now several reports of various point mutations in p300/CBP HAT domain being observed in human cancers and Rubinstein-Taybi syndrome but these have not been characterized with enzyme kinetic studies. Such p300/CBP mutations include R1378P in CBP(R1342P in p300) in Rubinstein-Taybi syndrome (Murata, et al. (2001) *Hum. Mol. Genet.* 10:1071-1076), D1399Y in p300 in primary colon cancer (Muraoka, et al. (1996) supra), S1650Y in p300 in pancreatic cancer (Gayther, et al. (2000) supra), and R1446C(R1410 in p300), W1472C (W1436 in p300), G1411E (G1375 in p300) in CBP in human lung cancer (Kishimoto, et al. (2005) supra). The importance of Arg1410 and Trp1436 has been discussed above, and it is likely that replacement of these critical residues by Cys will severely decrease p300/CBP HAT activity as was observed with Ala substitutions. Arg1342 is in the middle of the α2 helix, and replacement by Pro will interrupt the helix, and it is expected that this helical destabilization would disrupt the β1-β2 interaction of the core domain. Indeed, enzymatic analysis shows that a R1342P mutation results in at least a 50-fold reduction in acetyltransferase activity compared with wild-type p300 HAT (FIG. 7). In contrast, R1342K and R1342A p300 HAT mutants both show only modest 3-4-fold rate reductions, and these Arg replacements would be less likely to disrupt helical secondary structure (FIG. 7). Asp1399 is a key residue of the hydrogen bonding network between the substrate binding loop L1 and the β4 core domain where it forms a direct interaction with His1451. Mutagenesis analysis shows that the D1399Y, D1399N, and D1399A p300 HAT mutants all have very low activity (<1% wt p300 HAT activity) (FIG. 7), indicating that the L1 loop interaction with the core domain requires the negatively charged side chain of Asp1399 to form a strong hydrogen bond with His1451. Ser1650 is located at the upper middle portion of α9. It is expected that the bulkier side-chain found in S1650Y will not be accommodated by the limited space available around the tight turn region between α8 and α9, thereby interfering with the conformation of the final two α-helices, which themselves appear crucial because of their interactions with the L1 loop (the C-terminal truncated protein has very low activity probably for the same reason). As expected, S1650Y p300 HAT was greatly impaired catalytically (50-fold rate reduction), whereas the smaller replacement found in S1650A led to very similar catalytic activity compared to wild-type p300 HAT (FIG. 7). Although G1375E p300 HAT was not prepared, it is clear from the structure that a Glu substitution here would disrupt the appropriate positioning of the L1 loop for substrate binding (FIG. 7).

Example 6 p300 L1 Loop

The L1 loop (between β5 and α6, amino acid residues 1436-1459 SEQ ID NO:1) is a specialized feature of p300 HAT which serves as a lid for Lys-CoA. Based upon structural analysis, a related loop was identified within the yeast HAT RTT109 which is overall a rather close structural homolog of p300/CBP (despite very limited sequence homology). Based on the structure (FIG. 3), the L1 loop appears to be relevant for either substrate positioning, acetyl transfer, and/or product release. Thus, in addition to Trp4136Ala and Tyr1446Phe point mutations, a series of p300 HAT point mutants within the L1 loop are prepared and the kinetics ($k_{cat}$, $K_m$ measurements, viscosity effects) and binding properties using acetyltransferase assays and fluorescence binding assays with CoA analogs (CoASH, acetonyl-CoA, Lys-CoA) are carried out. L1 residues that appear to be directly interactive with Lys-CoA (Ala1437, Cys1438, Pro1439, P1440, Lys1456, Pro1458) as well as residues that may be important for loop flexibility (Pro1439, Pro1440, Pro1458) are selected for Ala scanning (or Gly for Ala1437). To investigate regulation, it is determined how loop autoacetylation, which stimulates the wild-type enzyme, affects the kinetics of particular mutants. Outcomes of interest for these experiments would be the identification of key residues that affect the rate of acetyl transfer ($k_{cat}$ drop or change in viscosity effect), the affinity for CoA or peptide, selective effects on Lys-CoA binding or sensitivity to autoacetylation. Pro to Ala (or Gly) mutants are expected to alter the loop flexibility and provide insights into the backbone effects of these residues on loop conformation. Complementary experiments involve obtaining X-ray structures of p300 HAT in complex with CoASH and acetonyl-CoA to determine how the L1 loop and P1 pocket are influenced by the Lys-side chain. Taken together, these studies allow a more complete understanding of the relationship between structure and mechanism of p300/CBP and how autoacetylation exerts its effect on catalysis. These experiments are also relevant in the comparative biochemistry of yeast RTT10999 and p300/CBP, which as mentioned are unique in containing the L1 loop. A practical result from these L1 mutant studies is the identification of mutants that are less potently inhibited by Lys-CoA (and other inhibitors) but still retain robust acetyltransferase activity. The application of such mutants in cellular studies in "knock-in" type experiments allows for the discrimination between the biological functions of p300 and CBP HATs by permitting selective enzyme inhibition.

Example 7 p300 HAT in Protein-Protein Interactions

The p300 HAT structure shows a negatively charged pocket (P2) near the Lys moiety of Lys-CoA and has led to the plausible notion that basic substrates interact in this pocket. It is contemplated that the b-ZIP domain of ATF2 which shows affinity for the loop-deleted or autoacetylated p300 HAT and is an in vitro p300 substrate may interact with the p300 P2 pocket. It has been shown that two Asp residues (Asp1625, Asp1628) may be central to the preference for basic peptide substrates based on mutagenesis studies with the Asp-Asp/Arg-Arg variant. Accordingly, related experiments can be carried out with the ATF2-b-ZIP domain to determine whether mutation of these residues affects p300 HAT binding or acetylation of this transcription factor. Pull-down experiments as well as acetyltransferase assays are carried out on the Asp-Asp/Arg-Arg p300 HAT to see if GST-ATF2-bZIP shows differential interaction with the P2 mutant, as expected. Wherein the Asp-Asp/Arg-Arg mutant does not show reduced interaction with ATF-2-b-ZIP, this indicates an alternate p300 region of interaction. In either case, co-crystallization of p300 HAT with ATF2-b-ZIP is performed to determine the high resolution structural basis of interaction.

Figure 9:
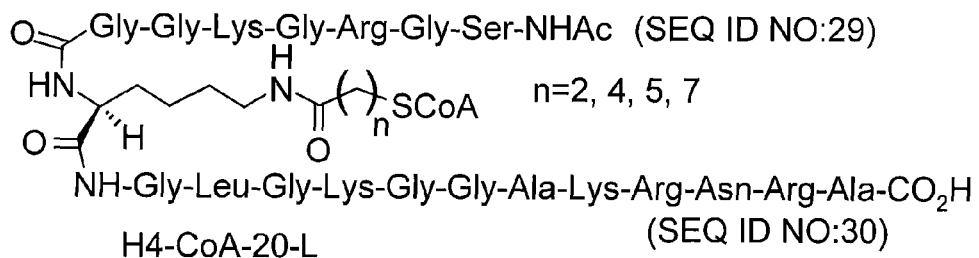
FIG. 9 shows H4-CoA-20 linker variants for structural analysis.
Figure 9:
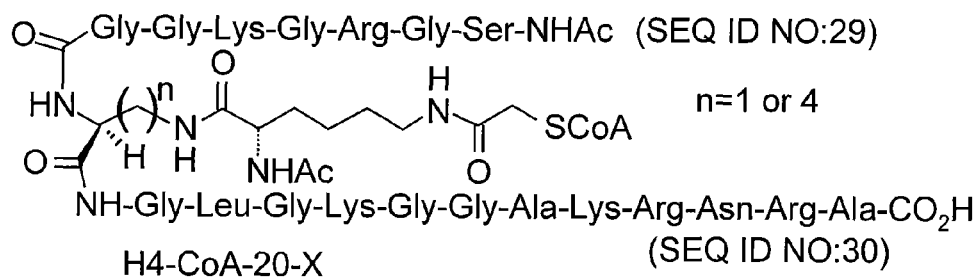
Figure 9:
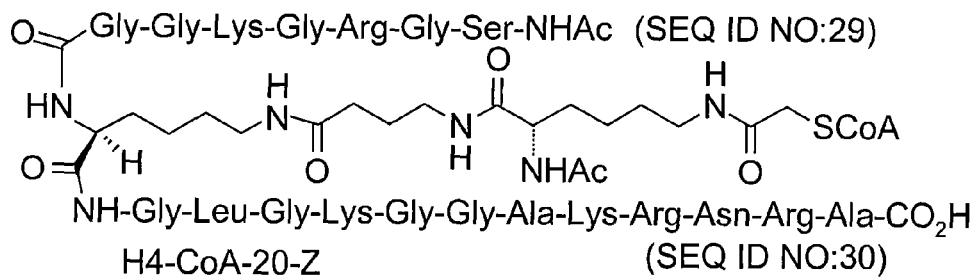

Regarding histone peptide substrate recognition by p300, studies with bisubstrate analogs, structure, and steady-state kinetics indicate that co-crystallization with H4 peptide or an H4-CoA-20 analog are unlikely to reveal relevant interactions because they are weak ligands. To circumvent this, H4-CoA-20 variants with extended linkers between peptide and CoA (L, X, Z; see FIG. 9) are employed. A compound with a longer and flexible linker between the CoA and the H4 tail peptide is expected to place the H4 peptide moiety near the histone substrate's initial encounter surface on p300, permitting capture by X-ray crystallography. After synthesizing the compounds shown in FIG. 9, their potency is evaluated as p300 HAT inhibitors. The most potent compounds could indicate that dual occupancy of the p300 HAT 'Lys-CoA tunnel' as well as the adjacent 2-Asp pocket P2 is possible. This is determined by making H4 variants that replace the basic residues Lys5 and Lys12 as well as testing the p300 Asp-Asp/Arg-Arg mutant enzyme. Crystallographic analysis with the novel H4-CoA conjugates can also be performed.

Using cell co-transfection and in vitro enzymatic experiments, it has been found that a transcription factor called MAML1, critical in Notch signaling can activate full-length p300 HAT and also induce its hyper-autoacetylation. Like many transcription factors, it is known that MAML1 can bind to the p300/CBP C/H3 domain. It is contemplated that engaging the C/H3 domain with MAML1 relieves an intramolecular autoinhibitory interaction between the p300 HAT domain and the C/H3 domain (FIG. 1A). To demonstrate this, a trans interaction between p300 HAT and recombinant C/H3 domain is shown by examining the ability of the C/H3 domain to modulate p300 HAT domain activity and testing for affinity using pull-downs.

Example 8

Analysis of the p300 Autoacetylation Loop

To interrogate the regulatory autoacetylation loop in p300 HAT, a circularly permuted protein domain is employed. Such a circular permutation involves linking the natural N- and C-termini (residues 1287 and 1666) of the HAT domain and creating new termini at 1565 (N-terminus) and 1520 (C-terminus). This construct is then fused to an intein through its new C-terminus and the thioester generated is ligated to synthetic peptides containing the key autoacetylated lysines. This approach is particular useful because of the close proximity between the natural N- and C-termini; the p300 HAT crystal structure indicates that these termini are a mere 15 Å apart. Moreover, it has been demonstrated that the unlinked N- and C-subdomains of p300 HAT form a very stable complex, which also supports the use of circular permutation. In generating this circularly permuted p300 HAT, several linker lengths (6-10 residues, Gly rich linkers) can be tested to optimize expression. Because p300 HAT activity is toxic to *E. coli*, the production of the p300 Tyr1467Phe catalytically impaired mutant can be analyzed first. While this mutant will have reduced utility in acetyltransferase studies, it can be employed to assess the influence of the ligated regulatory loop (amino acid residues 1520-1565) on protein-protein interactions in binding studies. Ligation with various mono, di, and triacetylated regulatory segment peptides can be used to explore site-specific modifications on interaction. After completion of experiments on inactive circularly permuted p300 HAT, investigations with the non-catalytically impaired HAT are carried out. To limit toxicity from host protein p300 acetylation, the catalytically active HAT is coexpressed with Sir2 deacetylase. While autoacetylation of several residues in the circularly permuted p300 HAT (outside the regulatory loop which is installed in vitro) is likely, as demonstrated herein, these sites are not very influential on p300 HAT activity. With the semi-synthetic circularly permuted p300 HAT proteins in hand, kinetic parameters of the various site-specifically acetylated forms are measured. These studies generate unique and important new information on how p300/CBP is regulated. If functional effects conferred by the unilaterally attached regulatory segment are not observed, the free (C-terminal end) can be linked by native chemical ligation to the new N-terminus of the circularly permuted protein. This can be achieved by generating a C-terminal thioester synthetic segment and an N-Cys on the N-terminus using Factor Xa cleavage or by a trans-splicing strategy.

As an alternative approach to generating a circularly permuted protein domain, a heterodimeric p300 HAT is generated by producing separate non-attached segments, which are co-expressed in *E. coli*. The N-subdomain is fused to an intein to allow ligation to regulatory segment peptides. The heterodimers thus produced would then be used in binding and catalytic studies as described for the circularly permuted protein.

Example 9

Virtual Library Screening of p300/CBP

Figure 10A:
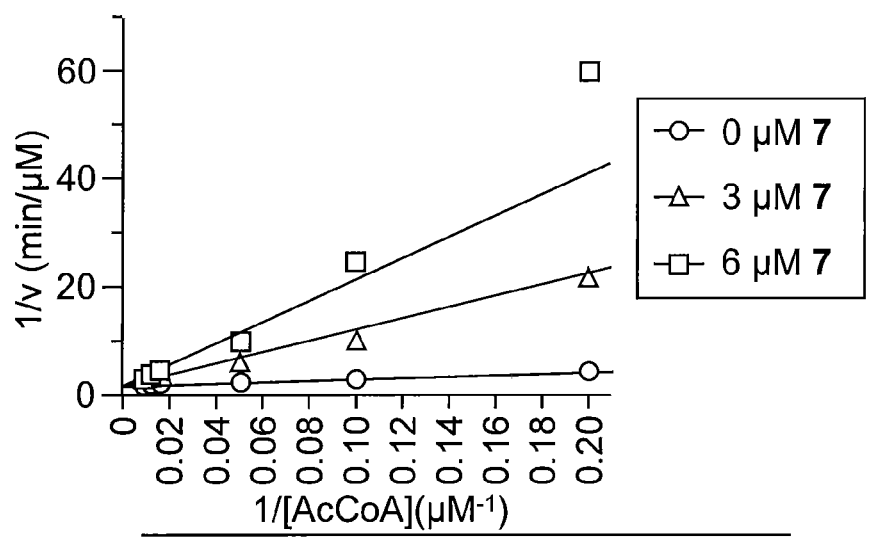
FIG. 10 shows the pattern of inhibition of compound 7 versus acetyl-CoA (FIG. 10A) or H4-15 (FIG. 10B).
Figure 10B:
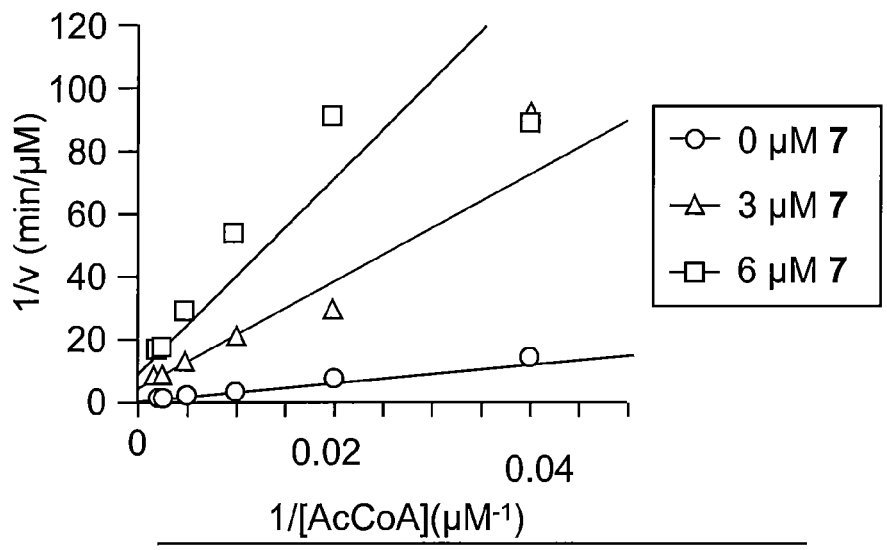

Regulatory molecules of p300/CBP HAT were identified by using the coordinates of the p300 HAT-Lys-CoA crystal structure and systematically docking into the active site (in the Lys-CoA binding region) the structures of ~2 million commercially available compounds (from the Chembridge library) in silico via ICM software algorithm. The top 200 compounds were selected, which also had favorable drug-like properties (MW<500, logP=1-6), and screened against p300 HAT using a spectrophotometric coupled assay that measures CoASH production in real-time. After secondary and tertiary screens (including a direct, radioactive assay that measures $^{14}C$-incorporation from acetyl-CoA into H4 tail peptide), three compounds (7, 17.2 and 17.3) were identified, which had $IC_{50}$s less than 20 µM, e.g., the $IC_{50}$ of 7 was 3.09±0.62 µM. Moreover, 7 was shown to exhibit competitive inhibition against acetyl-CoA (FIG. 10A) and mixed-type inhibition with H4-15 substrate (FIG. 10B).

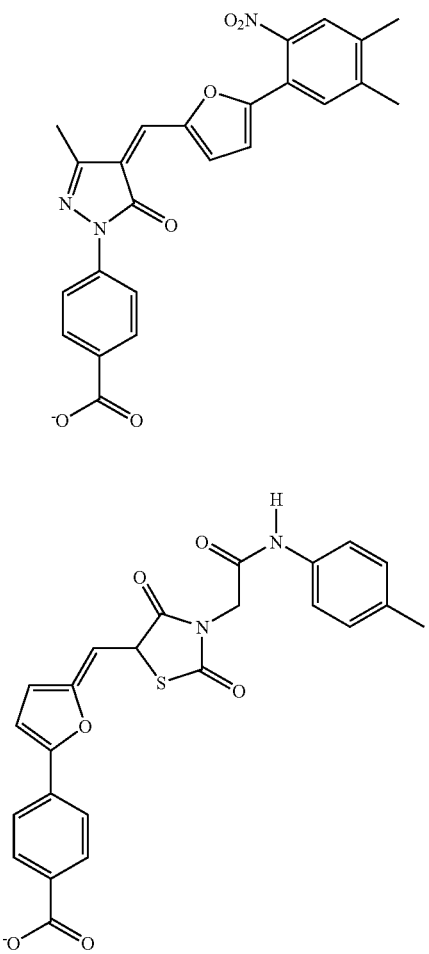

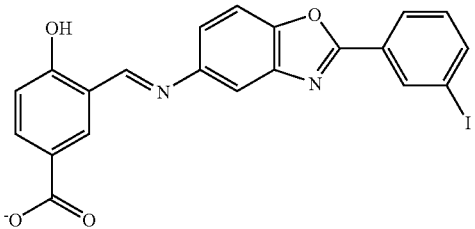

The chemical structures and purity of these three compounds were analyzed by NMR and mass spectrometry. It is noteworthy that these compounds contain a benzoate moiety linked to a series of aryl groups, which based on the computational docking (FIG. 11) overlaps with CoA binding.

Example 10

Mechanistic Analysis of p300/CBP HAT Inhibitors

The three small molecule p300 HAT inhibitors (7, 17.2 and 17.3) identified using virtual library screening provided new leads for further development. Based upon the docking model of binding of compound 7 (FIG. 11) and pattern of competitive inhibition of compound 7 versus acetyl-CoA (FIG. 10A), it is expected that analogs of compound 7 will compete for binding with acetyl-CoA. Similarly, based upon the pattern of mixed-type inhibition of compound 7 versus peptide substrate (FIG. 10B), it is expected that analogs of compound 7 exhibit non-competitive binding. Compounds that are found not to be linear competitive inhibitors vs. acetyl-CoA (studies indicate that 7 is competitive with $K_i$=400 nM) are likely binding differently from the proposed docking model. From the docking model of 7 to p300 HAT (FIG. 11), important hydrogen bonding roles are indicated for the side-chains of Arg1410, Thr1411, Trp1466 (all interacting with the inhibitor carboxylate) as well as the side-chain of Tyr1467 (hydrogen bonding to the nitro group). While Arg1410 and Tyr1467 are critical for CoA binding and/or catalysis, mutation of Trp1466 is well-tolerated. To explore the specificity of the small molecule HAT inhibitors, these compounds are tested against other acetyltransferases (PCAF, AANAT, RTT109, Esa1), which assists in the prioritization of candidates for pharmacologic applications.

Indeed, it was demonstrated that compound 7 was specific for p300 HAT (85.9% inhibition) compared to AANAT (4.8% inhibition) and PCAF (0% inhibition).

Example 11

Synthetic Derivation of p300/CBP HAT Inhibitors Synthesis of congeners of 7 involved the use of Knoevenagel condensation of furanyl-aldehyde derivatives with a set of pyrazolone building blocks.

General Procedure for Synthesis of
1-Aryl-3-Methyl-Pyrazol-5-One (3)

1-Aryl-3-methyl-pyrazol-5-one 3 was synthesized following a modified literature procedure (Scheme 1). (Kim & Lee (1991) *Bull. Korean Chem. Soc.* 12:376). A suspension of ethyl acetoacetate (2.8 mmol) and corresponding arylhydrazine (2, 3.3 mmol) in glacial acetic acid (30 ml) was stirred at reflux for 24 hours. The reaction mixture was concentrated and the solid precipitated out was filtered and washed with dichloromethane to remove traces of acetic acid. Yield 65-73%. 3b was synthesized by esterification of 3a in ethanol and purified by column chromatography using dichloromethane as eluent.

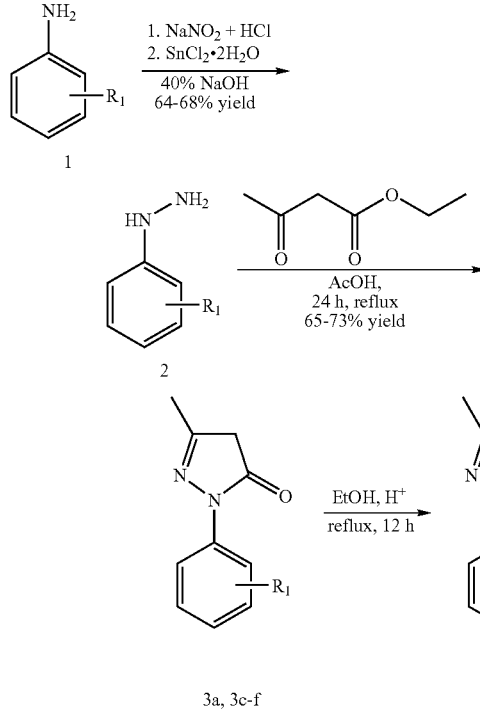

wherein $R_1$ is 4-COOH (3a), 4-COOEt (3b), 4-CONH$_2$ (3c), 3-COOH (3d), 4-SO$_3$H (3e), 4-Cl (3f).

1-Bromo-4,5-dimethyl-2-nitrobenzene 4a was synthesized in 81% yield using Sandmeyer reaction on 4,5-dimethyl-2-nitroaniline following a known procedure (Scheme 2) (Langner, et al. (2005) *Chem. Eur. J.* 11:6254). Ethyl 2-iodobenzoate 4d was prepared from esterification of corresponding halo-acid by refluxing in ethanol for 24 h. Pure product was obtained in 85% yield by column chromatography using dichloromethane as eluent.

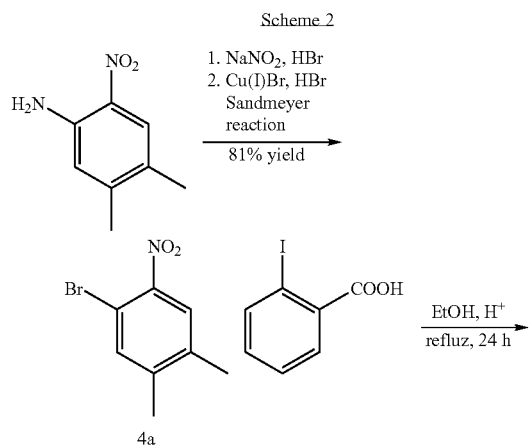

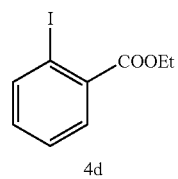

General Procedures for Synthesis of 5-Aryl-2-Furaldehydes (5)

5-Aryl-2-furaldehyde 5 was synthesized from Suzuki coupling of 5-formyl-2-furanboronic acid and corresponding aryl halides 4 in 72-75% yields following a literature procedure (Scheme 3) (Hosoya, et al. (2003) *Bioorg. Med. Chem.* 11:663). The crude solid products were purified by column chromatography using dichloromethane as eluent.

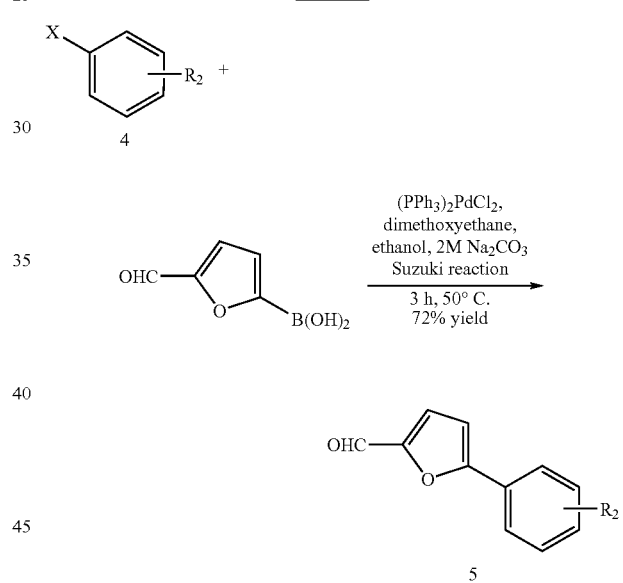

wherein $R_2$ is 2-NO$_2$, 3,4-diMe (4a, 5a); H (4b, 5b); 4-NO$_2$ (4c, 5c); 2-COOEt (4d, 5d).

General Procedure for Synthesis of 1-Aryl-3-Methyl-4-[[5-Aryl-2-Furanyl]Methylene]-Pyrazol-5-One (6)

The final compounds were synthesized following a modified literature procedure (Scheme 4) (2005) *Russ. J. Org. Chem.* 41:742). An equimolar solution of 1-aryl-3-methyl-pyrazol-5-one, 5-aryl-2-furaldehyde and diethylamine was stirred in ethanol at 50° C. for 1-3 hours. On cooling the precipitated red solid was filtered and further purified by column chromatography using 2-10% MeOH/DCM as eluent. The structures of all the compounds were confirmed from $^1$H NMR, ESI-MS and HRMS analysis.

Scheme 4

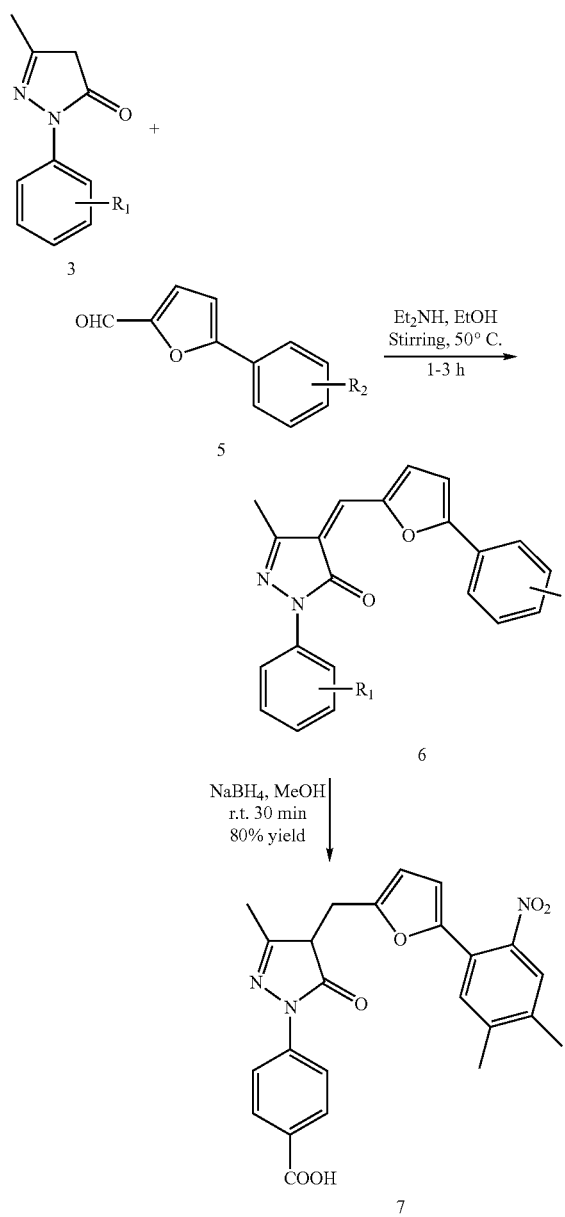

wherein for 3 R₁ is 4-COOH (3a), 4-COOEt (3b), 4-CONH₂ (3c), 3-COOH (3d), 4-SO₃H (3e), 4-Cl (3f); for 5 R₂ is 2-NO₂, 3,4-diMe (5a), H (5b), 4-NO₂ (5c), 2-COOEt (5d); and for 6a R₁ is 4-COOH and R₂ is H, 6b R₁ is 4-COOH and R₂ is 4-NO₂, 6c R₁ is 4-COOH and R₂ is 2-COOEt, 6d R₁ is 4-COOEt and R₂ is 2-NO₂, 3,4-diMe, 6e R₁ is 3-COOH and R₂ is 2-NO₂, 3,4-diMe, 6f R₁ is 4-SO₃H and R₂ is 2-NO₂, 3,4-diMe, 6g R₁ is 4-COOH and R₂ is 2-NO₂, 3,4-diMe, 6h R₁ is 4-CONH₂ and R₂ is 2-NO₂, 3,4-diMe, and 6i R₁ is 4-Cl and R₂ is 2-NO₂, 3,4-diMe.

Compound 6a was obtained as a red solid in 50% yield, mp 306-309° C. ¹H NMR (400 MHz, DMSO-d₆) δ: 2.35 (3H, s, CH₃), 7.46-7.55 (4H, m, ArH), 7.75 (1H, s, CH), 7.96-8.02 (4H, m, ArH), 8.08 (2H, m, ArH), 8.66 (1H, br s, ArH), 12.84 (1H, br s, COOH); HRMS: Calculated [M] for C₂₂H₁₆N₂O₄, 372.1110; observed [M+H]⁺373.1189, observed [M+H]⁺ from ESI-MS: 373.3.

Compound 6b was obtained as a red solid in 60% yield, mp 338-341° C. ¹H NMR (400 MHz, DMSO-d₆) δ: 2.35 (3H, s, CH₃), 7.73 (2H, d, J=4.0 Hz, ArH), 7.77 (1H, s, ArH), 7.99 (2H, d, J=8.8 Hz, ArH), 8.07 (2H, d, J=8.8 Hz, ArH), 8.17 (2H, d, J=9.2 Hz, ArH), 8.36 (2H, d, J=8.8 Hz, ArH), 12.84 (1H, br s, COOH); HRMS: Calculated [M]⁺ for C₂₂H₁₅N₃O₆, 417.0961; observed [M+H]⁺418.1040.

Compound 6c was obtained as a red solid in 41% yield, mp 249-251° C. ¹H NMR (400 MHz, DMSO-d₆) δ: 1.16 (3H, t, J=7.6 Hz, COOCH₂CH₃), 2.33 (3H, s, CH₃), 4.27 (2H, q, J=7.0 Hz, COOCH₂CH₃), 7.22 (1H, d, J=4.0 Hz, ArH), 7.60 (1H, d, J=6.0 Hz, ArH), 7.63 (1H, m, ArH), 7.68-7.81 (2H, m, ArH), 7.87 (1H, d, J=7.2 Hz, ArH), 8.00-8.02 (2H, m, ArH), 8.08 (2H, d, J=8.4 Hz, ArH), 8.70 (1H, d, J=3.2 Hz, ArH), (1H, br s, COOH); HRMS: Calculated [M]⁺ for C₂₅H₂₀N₂O₆, 444.1321; observed [M+H] 445.1396, observed [M+H]⁺ from ESI-MS: 445.2. See WO 2006/129583 and WO 2006/129587.

Compound 6d was obtained as a red solid in 70% yield, mp 192-194° C. ¹H NMR (400 MHz, CDCl₃) δ: 1.40 (3H, t, J=7.2 Hz, COOCH₂CH₃), 2.34 (3H, s, CH₃), 2.38 and 2.39 (6H, 2s, 2×CH₃), 4.37 (2H, q, J=7.2 Hz, COOCH₂CH₃), 6.92 (1H, d, J=4.0 Hz, ArH), 7.28 (1H, s, CH), 7.53 (1H, s, ArH), 7.65 (1H, s, ArH), 8.08-8.14 (4H, m, ArH), 8.82 (1H, d, J=4.0 Hz, ArH); HRMS: Calculated [M]+ for C₂₆H₂₃N₃O₆, 473.1587; observed [M+H]⁺474.1660, observed [M+H]⁺ from ESI-MS: 474.3.

Compound 6e was obtained as a red solid in 64% yield, mp 260-262° C. ¹H NMR (400 MHz, DMSO-d₆) δ: 2.33, 2.35 and 2.36 (9H, 3s, 3×CH₃), 7.18 and 7.23 (1H, dd, J=4.0 and 18.8 Hz, ArH), 7.53-7.58 (2H, m, ArH), 7.70-7.78 (2H, m, ArH), 7.85 (1H, s, CH), 8.15 (1H, d, J=7.0 Hz, ArH), 8.55 (1H, d, J=1.2 Hz, ArH), 8.71 (1H, d, J=3.2 Hz, ArH), 13.12 (1H, br s, COOH); HRMS: Calculated [M] for C₂₄H₁₉N₃O₆, 445.1274; observed [M+H]⁺446.1349, observed [M+H]⁺ from ESI-MS: 446.2.

Compound 6f was obtained as a red solid in 58% yield, mp 210-213° C. ¹H NMR (400 MHz, DMSO-d₆) δ: 2.31, 2.33 and 2.35 (9H, 3s, 3×CH₃), 6.90-6.96 (1H, m, ArH), 7.20 (1H, m, ArH), 7.45-7.55 (1H, m, ArH), 7.63-7.72 (2H, m, ArH), 7.76 (1H, s, CH), 7.84 (1H, s, ArH), 7.90 (1H, d, J=8.4 Hz, ArH), 8.23 (1H, br s, ArH), 10.58 (1H, s, SO₃H); HRMS: Calculated [M] for C₂₃H₁₉N₃O₇S, 481.0944; observed [M+H] 482.1021, observed [M+H]⁺ from ESI-MS: 482.3.

Compound 6g was obtained as a red solid in 72% yield. Calculated [M]⁺ for C₂₄H₁₉N₃O₆, 445.1274; observed [M+H]⁺ from ESI-MS: 446.1. The synthesized 6g was compared with compound 7 obtained commercially on TLC and found of same R_f (4% MeOH/DCM).

Compound 6h was obtained as a red solid in 40% yield, mp 273-275° C. ¹H NMR (400 MHz, DMSO-d₆) δ: 2.32, 2.33 and 2.35 (9H, 3s, 3×CH₃), 7.22 (1H, d, J=3.2 Hz, ArH), 7.33 (1H, s, ArH), 7.56 (1H, s, ArH), 7.75 (1H, s, 1H), 7.84 (1H, s, ArH), 7.92-8.01 (3H, m, 3ArH, CONH₂), 8.68 (1H, d, J=2.4 Hz, ArH); HRMS: Calculated [M] for C₂₄H₂₀N₄O₅, 444.1434; observed [M+H]⁺445.1507, observed [M+H]⁺ from ESI-MS: 445.4.

Compound 6i was obtained as a red solid in 75% yield, mp 220-223° C. ¹H NMR (400 MHz, CDCl₃-d₆) δ: 2.32 (3H, s, CH₃), 2.37 and 2.38 (6H, 2s, 2×CH₃), 6.90 (1H, d, J=4.0 Hz, ArH), 7.26 (1H, s, CH), 7.36 (2H, d, J=8.4 Hz, ArH), 7.51 (1H, s, ArH), 7.63 (1H, s, ArH), 7.94 (2H, d, J=8.8 Hz, ArH), 8.80 (1H, d, J=4.0 Hz, ArH); HRMS: Calculated [M]⁺ for C₂₃H₁₈N₃O₄Cl, 435.0986; observed [M+H]⁺ 436.1061, observed [M+H]⁺ from ESI-MS: 436.1.

General Procedure for Synthesis of 7

To a solution of 6g (2.24 mmol) in methanol (20 ml), sodium borohydride (2.24 mmol) was added portion-wise, effervescence was evolved and the color of the solution changed from dark red to light yellow. The resulting solution was stirred at room temperature for 30 minutes, solvent was removed and pH of the solution was made 7.0 on adding dilute HCl drop-wise. The resulting mixture was extracted with EtOAc (2×50 ml) and concentrated to give an orange solid in 80.0% yield, mp 160-163° C. $^1$H NMR (400 MHz, DMSO-$d_6$) δ: 2.02 (3H, s, $CH_3$), 2.27 and 2.28 (6H, 2s, 2×$CH_3$), 3.56 (2H, s, $CH_2$), 6.05 (1H, br s, ArH), 6.61 (1H, br s, ArH), 7.50 (1H, s, ArH), 7.61 (1H, s, ArH), 7.85 (2H, d, J=8.4 Hz, ArH), 8.04 (2H, d, J=8.4 Hz, ArH), 12.80 (1H, br s, COOH); HRMS: Calculated [M] for $C_{24}H_{21}N_3O_6$, 447.1430; observed [M+H] 448.1507, observed [M+H]$^+$ from ESI-MS: 448.3.

General Procedure for Synthesis of 9

3-Methyl-pyrazol-5-one was synthesized in 60% yield on stirring an equimolar mixture of hydrazine monohydrate and ethyl acetoacetate in ethanol. The exothermic reaction was then cooled in ice-bath to precipitate out a solid white product. The structure of the product was confirmed from ESI-MS and comparing the observed melting point (214-216° C.) with the literature melting point (218° C.; Singh, et al. (2005) *Eur. J. Pharm. Sci.* 25:255-262). Compound 8 was obtained in on alkylation of 3-methylpyrazol-5-one with equimolar 1-bromovaleric acid by refluxing in 1,4-dioxane for 48 hours following conventional procedures (Belmar, et al. (2005) *J. Braz. Chem. Soc.* 16:179). See Scheme 5. The structure of compound 8 was confirmed from ESI-MS and used for next step without further purification.

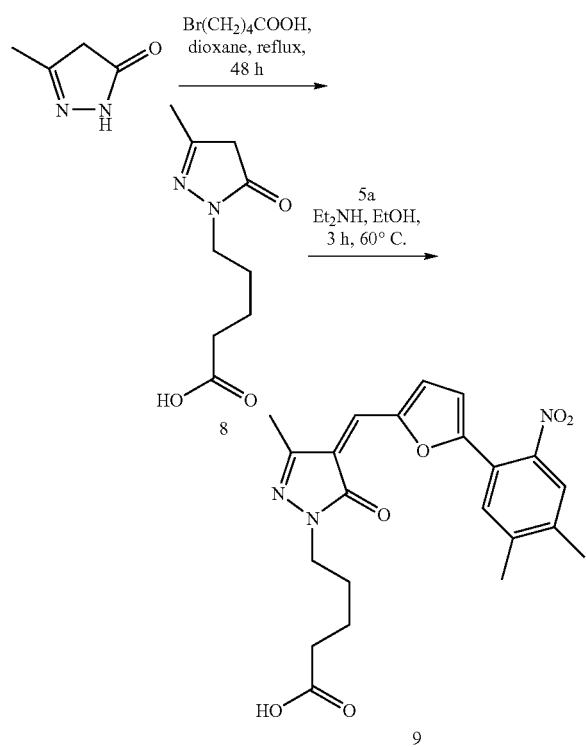

Scheme 5

Compound 9 was obtained in 15% yield from pyrazole 8 and 5-(2-nitro-4,5-dimethylphenyl)-2-furaldehyde 5a following the procedure described for the synthesis of compound 6 in Scheme 4. The product was purified by column chromatography using 2-3% MeOH/DCM as eluent. Compound 9 was obtained as a red solid in 15% yield, mp 240-243° C. $^1$H NMR (400 MHz, CDCl$_3$) δ: 1.58-1.74 (2H, m, $CH_2$), 2.23 (5H, s and m, $CH_3$ and $CH_2$), 2.37 and 2.39 (10H, 2s and 2m, 2×$CH_3$ and 2×$CH_2$), 6.87 (1H, d, J=4.0 Hz, ArH), 7.21 (1H, s, CH), 7.52 (1H, s, ArH), 7.63 (1H, s, ArH), 8.71 (1H, br s, COOH), 8.75 (1H, d, J=4.0 Hz, ArH); HRMS: Calculated [M]$^+$ for $C_{22}H_{23}N_3O_6$, 425.1587; observed [M+H]+NA.

Example 12

Activity of p300/CBP HAT Inhibitors

Novel HAT inhibitors of the instant invention can be analyzed in a variety of systems with implications for endocrine, cancer, neuropsychiatric, and immunologic therapeutics. The compounds can be assessed in defined well-known model systems used to assess cellular permeability, toxicity, and pharmacodynamic effects. These assays include western blot analysis of histone acetylation as well as HAT-responsive transcriptional reporters that are specific for p300/CBP-mediated acetylation reactions. Regarding endocrine disorders, it has been found that p300/CBP HAT inhibition by Lys-CoA-Tat blocks CREB signaling and glucagon-induced glucose elevation. These data indicate that novel p300/CBP inhibitors could play a role in the treatment of diabetes mellitus. In addition, it has been shown that Lys-CoA-Tat can inhibit melanoma growth in three different cell lines. New HAT inhibitor scaffolds would thus be useful in treating cancers such as melanoma.

Indeed, the data disclosed herein indicates that inhibitors with a benzoate moiety linked to various aryl groups can inhibit p300/CBP HAT activity (see Tables 1 and 2) and find use in diseases mediated by p300/CBP HAT. Both cell-based assays and animal model studies are performed to further demonstrate efficacy in the treatment of diseases such as cancer.

Cell-Based Assay.

Cells from a P388 cell line (CellGate, Inc., Sunnyvale, Calif.) or human malignant melanoma cell line SK-MEL-2 are grown in RPMI 1640 cell medium containing fetal calf serum (10%), L-glutamine, penicillin, streptomycin and are split twice weekly. All compounds are first diluted with DMSO. Later serial dilutions are done with a phosphate-buffered saline solution. All dilutions are done in glass vials and the final DMSO concentration is generally below 0.5% by volume. Final two-fold dilutions are done in a 96-well plate using cell media so that each well contains 50 μL. All compounds are assayed over multiple concentrations. Cell concentration is measured using a hemacytometer and the final cell concentration is adjusted to about 1×10$^4$ cells/mL with cell medium. The resulting solution of cells (50 μL) is then added to each well and the plates are incubated for 5 days in a 37° C., 5% CO$_2$, humidified incubator. MTT solution (3-[4,5-dimethylthiazol-2-yl]-2,5-diphenyltetrazolium bromide, 10 μL) is then added to each well and the plates are re-incubated under identical conditions for 2 hours. To each well is then added acidified isopropanol (150 μL of i-PrOH solution containing 0.05 N HCl) and mixed thoroughly. The plates are then scanned at 595 nm and the absorbances are read (Wallac Victor 1420 Multilabel Counter). The resulting data is then analyzed to determine an ED$_{50}$ value. Compounds that kill cancer cells, but fail to kill normal cells, find application in the prevention or treatment of cancer.

Mouse Ovarian Carcinoma Zenograft Model.

Compounds of the invention are evaluated in an ovarian carcinoma xenograft model of cancer, based on that described by Davis, et al. ((1993) *Cancer Research* 53:2087-2091). This model, in brief, involves inoculating female nu/nu mice with $1 \times 10^9$ OVCAR3-icr cells into the peritoneal cavity. One or more test compounds are administered, e.g., prior to or after tumor cell injection, by the oral route as a suspension in 1% methyl cellulose or intraperitoneally as a suspension in phosphate-buffered saline in 0.01% TWEEN-20. At the conclusion of the experiment (4-5 weeks) the number of peritoneal cells are counted and any solid tumor deposits weighed. In some experiments tumor development is monitored by measurement of tumor specific antigens.

Rat Mammary Carcinoma Model.

Compounds of the invention are evaluated in a HOSP.1 rat mammary carcinoma model of cancer (Eccles, et al. (1995) *Cancer Res.* 56:2815-2822). This model involves the intravenous inoculation of $2 \times 10^4$ tumor cells into the jugular vein of female CBH/cbi rats. One or more test compounds are administered, e.g., prior to or after tumor cell injection, by the oral route as a suspension in 1% methyl cellulose or intraperitoneally as a suspension in phosphate-buffered saline and 0.01% TWEEN-20. At the conclusion of the experiment (4-5 weeks) the animals are killed, the lungs are removed and individual tumors counted after 20 hours fixation in Methacarn.

Mouse B16 Melanoma Model.

The anti-metastatic potential of compounds of the invention is evaluated in a B16 melanoma model in C57BL/6. Mice are injected intravenously with $2 \times 10^5$ B16/F10 murine tumor cells harvested from in vitro cultures. Inhibitors are administered by the oral route as a suspension in 1% methyl cellulose or intraperitoneally as a suspension in phosphate-buffered saline pH 7.2 and 0.01% TWEEN-20. Mice are killed 14 days after cell inoculation and the lungs removed and weighed prior to fixing in Bouin's solution. The number of colonies present on the surface of each set of lungs is then counted.

---

What is claimed is:

1. A p300/CBP inhibitor selected from the group of:

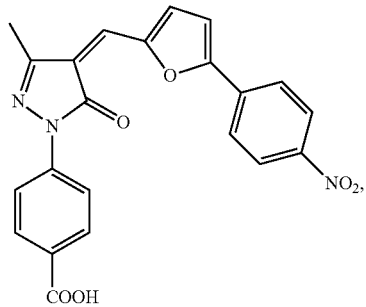

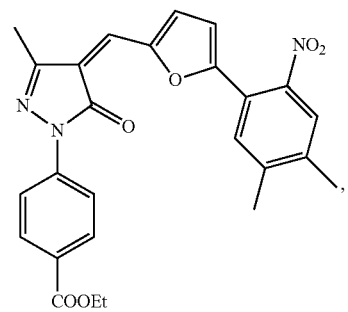

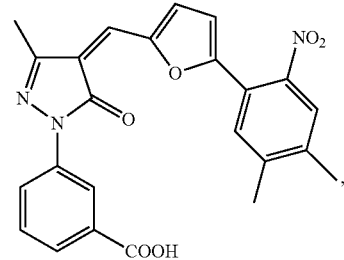

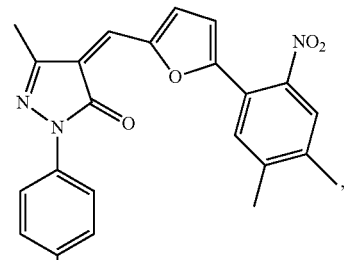

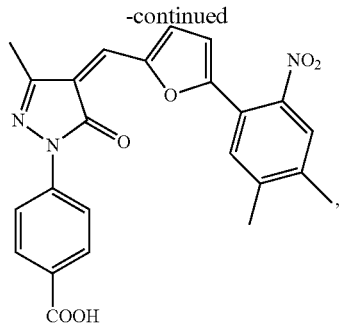

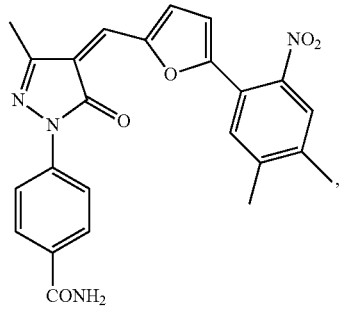

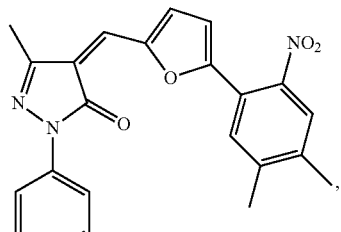

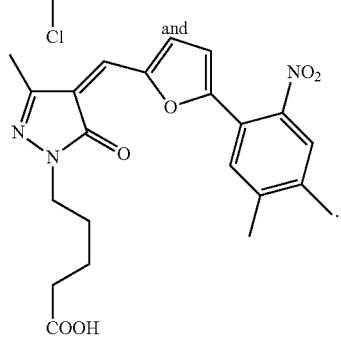

2. A pharmaceutical composition comprising a p300/CBP inhibitor of claim 1 in admixture with a pharmaceutically acceptable carrier.

* * * * *

SEQUENCE LISTING

```
<160> NUMBER OF SEQ ID NOS: 30

<210> SEQ ID NO 1
<211> LENGTH: 2414
<212> TYPE: PRT
<213> ORGANISM: Homo sapiens

<400> SEQUENCE: 1

Met Ala Glu Asn Val Val Glu Pro Gly Pro Pro Ser Ala Lys Arg Pro
1               5                   10                  15

Lys Leu Ser Ser Pro Ala Leu Ser Ala Ser Ala Ser Asp Gly Thr Asp
                20                  25                  30

Phe Gly Ser Leu Phe Asp Leu Glu His Asp Leu Pro Asp Glu Leu Ile
            35                  40                  45

Asn Ser Thr Glu Leu Gly Leu Thr Asn Gly Gly Asp Ile Asn Gln Leu
        50                  55                  60

Gln Thr Ser Leu Gly Met Val Gln Asp Ala Ala Ser Lys His Lys Gln
65                  70                  75                  80

Leu Ser Glu Leu Leu Arg Ser Gly Ser Ser Pro Asn Leu Asn Met Gly
                85                  90                  95

Val Gly Gly Pro Gly Gln Val Met Ala Ser Gln Ala Gln Gln Ser Ser
                100                 105                 110

Pro Gly Leu Gly Leu Ile Asn Ser Met Val Lys Ser Pro Met Thr Gln
            115                 120                 125

Ala Gly Leu Thr Ser Pro Asn Met Gly Met Gly Thr Ser Gly Pro Asn
        130                 135                 140

Gln Gly Pro Thr Gln Ser Thr Gly Met Met Asn Ser Pro Val Asn Gln
145                 150                 155                 160

Pro Ala Met Gly Met Asn Thr Gly Met Asn Ala Gly Met Asn Pro Gly
                165                 170                 175

Met Leu Ala Ala Gly Asn Gly Gln Gly Ile Met Pro Asn Gln Val Met
                180                 185                 190

Asn Gly Ser Ile Gly Ala Gly Arg Gly Arg Gln Asn Met Gln Tyr Pro
            195                 200                 205

Asn Pro Gly Met Gly Ser Ala Gly Asn Leu Leu Thr Glu Pro Leu Gln
        210                 215                 220

Gln Gly Ser Pro Gln Met Gly Gly Gln Thr Gly Leu Arg Gly Pro Gln
```

```
            225                 230                 235                 240
    Pro Leu Lys Met Gly Met Met Asn Asn Pro Asn Pro Tyr Gly Ser Pro
                    245                 250                 255

Tyr Thr Gln Asn Pro Gly Gln Gln Ile Gly Ala Ser Gly Leu Gly Leu
                260                 265                 270

Gln Ile Gln Thr Lys Thr Val Leu Ser Asn Asn Leu Ser Pro Phe Ala
                275                 280                 285

Met Asp Lys Lys Ala Val Pro Gly Gly Met Pro Asn Met Gly Gln
    290                 295                 300

Gln Pro Ala Pro Gln Val Gln Gln Pro Gly Leu Val Thr Pro Val Ala
    305                 310                 315                 320

Gln Gly Met Gly Ser Gly Ala His Thr Ala Asp Pro Glu Lys Arg Lys
                    325                 330                 335

Leu Ile Gln Gln Gln Leu Val Leu Leu Leu His Ala His Lys Cys Gln
                340                 345                 350

Arg Arg Glu Gln Ala Asn Gly Glu Val Arg Gln Cys Asn Leu Pro His
                355                 360                 365

Cys Arg Thr Met Lys Asn Val Leu Asn His Met Thr His Cys Gln Ser
            370                 375                 380

Gly Lys Ser Cys Gln Val Ala His Cys Ala Ser Ser Arg Gln Ile Ile
    385                 390                 395                 400

Ser His Trp Lys Asn Cys Thr Arg His Asp Cys Pro Val Cys Leu Pro
                    405                 410                 415

Leu Lys Asn Ala Gly Asp Lys Arg Asn Gln Gln Pro Ile Leu Thr Gly
                420                 425                 430

Ala Pro Val Gly Leu Gly Asn Pro Ser Ser Leu Gly Val Gly Gln Gln
                435                 440                 445

Ser Ala Pro Asn Leu Ser Thr Val Ser Gln Ile Asp Pro Ser Ser Ile
    450                 455                 460

Glu Arg Ala Tyr Ala Ala Leu Gly Leu Pro Tyr Gln Val Asn Gln Met
    465                 470                 475                 480

Pro Thr Gln Pro Gln Val Gln Ala Lys Asn Gln Gln Asn Gln Gln Pro
                    485                 490                 495

Gly Gln Ser Pro Gln Gly Met Arg Pro Met Ser Asn Met Ser Ala Ser
                500                 505                 510

Pro Met Gly Val Asn Gly Gly Val Gly Val Gln Thr Pro Ser Leu Leu
                515                 520                 525

Ser Asp Ser Met Leu His Ser Ala Ile Asn Ser Gln Asn Pro Met Met
    530                 535                 540

Ser Glu Asn Ala Ser Val Pro Ser Leu Gly Pro Met Pro Thr Ala Ala
    545                 550                 555                 560

Gln Pro Ser Thr Thr Gly Ile Arg Lys Gln Trp His Glu Asp Ile Thr
                    565                 570                 575

Gln Asp Leu Arg Asn His Leu Val His Lys Leu Val Gln Ala Ile Phe
                580                 585                 590

Pro Thr Pro Asp Pro Ala Ala Leu Lys Asp Arg Arg Met Glu Asn Leu
                595                 600                 605

Val Ala Tyr Ala Arg Lys Val Glu Gly Asp Met Tyr Glu Ser Ala Asn
            610                 615                 620

Asn Arg Ala Glu Tyr Tyr His Leu Leu Ala Glu Lys Ile Tyr Lys Ile
    625                 630                 635                 640

Gln Lys Glu Leu Glu Glu Lys Arg Arg Thr Arg Leu Gln Lys Gln Asn
                    645                 650                 655
```

```
Met Leu Pro Asn Ala Ala Gly Met Val Pro Val Ser Met Asn Pro Gly
            660                 665                 670

Pro Asn Met Gly Gln Pro Gln Pro Gly Met Thr Ser Asn Gly Pro Leu
            675                 680                 685

Pro Asp Pro Ser Met Ile Arg Gly Ser Val Pro Asn Gln Met Met Pro
            690                 695                 700

Arg Ile Thr Pro Gln Ser Gly Leu Asn Gln Phe Gly Gln Met Ser Met
705                 710                 715                 720

Ala Gln Pro Pro Ile Val Pro Arg Gln Thr Pro Leu Gln His His
                    725                 730                 735

Gly Gln Leu Ala Gln Pro Gly Ala Leu Asn Pro Pro Met Gly Tyr Gly
            740                 745                 750

Pro Arg Met Gln Gln Pro Ser Asn Gln Gly Gln Phe Leu Pro Gln Thr
            755                 760                 765

Gln Phe Pro Ser Gln Gly Met Asn Val Thr Asn Ile Pro Leu Ala Pro
            770                 775                 780

Ser Ser Gly Gln Ala Pro Val Ser Gln Ala Gln Met Ser Ser Ser
785                 790                 795                 800

Cys Pro Val Asn Ser Pro Ile Met Pro Pro Gly Ser Gln Gly Ser His
            805                 810                 815

Ile His Cys Pro Gln Leu Pro Gln Pro Ala Leu His Gln Asn Ser Pro
            820                 825                 830

Ser Pro Val Pro Ser Arg Thr Pro Thr Pro His His Thr Pro Pro Ser
            835                 840                 845

Ile Gly Ala Gln Gln Pro Pro Ala Thr Thr Ile Pro Ala Pro Val Pro
            850                 855                 860

Thr Pro Pro Ala Met Pro Pro Gly Pro Gln Ser Gln Ala Leu His Pro
865                 870                 875                 880

Pro Pro Arg Gln Thr Pro Thr Pro Pro Thr Thr Gln Leu Pro Gln Gln
                    885                 890                 895

Val Gln Pro Ser Leu Pro Ala Ala Pro Ser Ala Asp Gln Pro Gln Gln
            900                 905                 910

Gln Pro Arg Ser Gln Gln Ser Thr Ala Ala Ser Val Pro Thr Pro Thr
            915                 920                 925

Ala Pro Leu Leu Pro Pro Gln Pro Ala Thr Pro Leu Ser Gln Pro Ala
930                 935                 940

Val Ser Ile Glu Gly Gln Val Ser Asn Pro Pro Ser Thr Ser Ser Thr
945                 950                 955                 960

Glu Val Asn Ser Gln Ala Ile Ala Glu Lys Gln Pro Ser Gln Glu Val
                    965                 970                 975

Lys Met Glu Ala Lys Met Glu Val Asp Gln Pro Glu Pro Ala Asp Thr
            980                 985                 990

Gln Pro Glu Asp Ile Ser Glu Ser  Lys Val Glu Asp Cys  Lys Met Glu
            995                 1000                1005

Ser Thr  Glu Thr Glu Glu Arg  Ser Thr Glu Leu Lys  Thr Glu Ile
            1010                1015                1020

Lys Glu  Glu Glu Asp Gln Pro  Ser Thr Ser Ala Thr  Gln Ser Ser
            1025                1030                1035

Pro Ala  Pro Gly Gln Ser Lys  Lys Lys Ile Phe Lys  Pro Glu Glu
            1040                1045                1050

Leu Arg  Gln Ala Leu Met Pro  Thr Leu Glu Ala Leu  Tyr Arg Gln
            1055                1060                1065

Asp Pro  Glu Ser Leu Pro Phe  Arg Gln Pro Val Asp  Pro Gln Leu
            1070                1075                1080
```

```
Leu Gly Ile Pro Asp Tyr Phe Asp Ile Val Lys Ser Pro Met Asp
    1085            1090                1095
Leu Ser Thr Ile Lys Arg Lys Leu Asp Thr Gly Gln Tyr Gln Glu
    1100            1105                1110
Pro Trp Gln Tyr Val Asp Asp Ile Trp Leu Met Phe Asn Asn Ala
    1115            1120                1125
Trp Leu Tyr Asn Arg Lys Thr Ser Arg Val Tyr Lys Tyr Cys Ser
    1130            1135                1140
Lys Leu Ser Glu Val Phe Glu Gln Glu Ile Asp Pro Val Met Gln
    1145            1150                1155
Ser Leu Gly Tyr Cys Cys Gly Arg Lys Leu Glu Phe Ser Pro Gln
    1160            1165                1170
Thr Leu Cys Cys Tyr Gly Lys Gln Leu Cys Thr Ile Pro Arg Asp
    1175            1180                1185
Ala Thr Tyr Tyr Ser Tyr Gln Asn Arg Tyr His Phe Cys Glu Lys
    1190            1195                1200
Cys Phe Asn Glu Ile Gln Gly Glu Ser Val Ser Leu Gly Asp Asp
    1205            1210                1215
Pro Ser Gln Pro Gln Thr Thr Ile Asn Lys Glu Gln Phe Ser Lys
    1220            1225                1230
Arg Lys Asn Asp Thr Leu Asp Pro Glu Leu Phe Val Glu Cys Thr
    1235            1240                1245
Glu Cys Gly Arg Lys Met His Gln Ile Cys Val Leu His His Glu
    1250            1255                1260
Ile Ile Trp Pro Ala Gly Phe Val Cys Asp Gly Cys Leu Lys Lys
    1265            1270                1275
Ser Ala Arg Thr Arg Lys Glu Asn Lys Phe Ser Ala Lys Arg Leu
    1280            1285                1290
Pro Ser Thr Arg Leu Gly Thr Phe Leu Glu Asn Arg Val Asn Asp
    1295            1300                1305
Phe Leu Arg Arg Gln Asn His Pro Glu Ser Gly Glu Val Thr Val
    1310            1315                1320
Arg Val Val His Ala Ser Asp Lys Thr Val Glu Val Lys Pro Gly
    1325            1330                1335
Met Lys Ala Arg Phe Val Asp Ser Gly Glu Met Ala Glu Ser Phe
    1340            1345                1350
Pro Tyr Arg Thr Lys Ala Leu Phe Ala Phe Glu Glu Ile Asp Gly
    1355            1360                1365
Val Asp Leu Cys Phe Phe Gly Met His Val Gln Glu Tyr Gly Ser
    1370            1375                1380
Asp Cys Pro Pro Pro Asn Gln Arg Arg Val Tyr Ile Ser Tyr Leu
    1385            1390                1395
Asp Ser Val His Phe Phe Arg Pro Lys Cys Leu Arg Thr Ala Val
    1400            1405                1410
Tyr His Glu Ile Leu Ile Gly Tyr Leu Glu Tyr Val Lys Lys Leu
    1415            1420                1425
Gly Tyr Thr Thr Gly His Ile Trp Ala Cys Pro Pro Ser Glu Gly
    1430            1435                1440
Asp Asp Tyr Ile Phe His Cys His Pro Pro Asp Gln Lys Ile Pro
    1445            1450                1455
Lys Pro Lys Arg Leu Gln Glu Trp Tyr Lys Lys Met Leu Asp Lys
    1460            1465                1470
Ala Val Ser Glu Arg Ile Val His Asp Tyr Lys Asp Ile Phe Lys
```

-continued

```
               1475                1480                1485

Gln Ala Thr Glu Asp Arg Leu Thr Ser Ala Lys Glu Leu Pro Tyr
    1490                1495                1500

Phe Glu Gly Asp Phe Trp Pro Asn Val Leu Glu Glu Ser Ile Lys
    1505                1510                1515

Glu Leu Glu Gln Glu Glu Glu Arg Lys Arg Glu Glu Asn Thr
    1520                1525                1530

Ser Asn Glu Ser Thr Asp Val Thr Lys Gly Asp Ser Lys Asn Ala
    1535                1540                1545

Lys Lys Lys Asn Asn Lys Lys Thr Ser Lys Asn Lys Ser Ser Leu
    1550                1555                1560

Ser Arg Gly Asn Lys Lys Lys Pro Gly Met Pro Asn Val Ser Asn
    1565                1570                1575

Asp Leu Ser Gln Lys Leu Tyr Ala Thr Met Glu Lys His Lys Glu
    1580                1585                1590

Val Phe Phe Val Ile Arg Leu Ile Ala Gly Pro Ala Ala Asn Ser
    1595                1600                1605

Leu Pro Pro Ile Val Asp Pro Asp Pro Leu Ile Pro Cys Asp Leu
    1610                1615                1620

Met Asp Gly Arg Asp Ala Phe Leu Thr Leu Ala Arg Asp Lys His
    1625                1630                1635

Leu Glu Phe Ser Ser Leu Arg Arg Ala Gln Trp Ser Thr Met Cys
    1640                1645                1650

Met Leu Val Glu Leu His Thr Gln Ser Gln Asp Arg Phe Val Tyr
    1655                1660                1665

Thr Cys Asn Glu Cys Lys His His Val Glu Thr Arg Trp His Cys
    1670                1675                1680

Thr Val Cys Glu Asp Tyr Asp Leu Cys Ile Thr Cys Tyr Asn Thr
    1685                1690                1695

Lys Asn His Asp His Lys Met Glu Lys Leu Gly Leu Gly Leu Asp
    1700                1705                1710

Asp Glu Ser Asn Asn Gln Gln Ala Ala Ala Thr Gln Ser Pro Gly
    1715                1720                1725

Asp Ser Arg Arg Leu Ser Ile Gln Arg Cys Ile Gln Ser Leu Val
    1730                1735                1740

His Ala Cys Gln Cys Arg Asn Ala Asn Cys Ser Leu Pro Ser Cys
    1745                1750                1755

Gln Lys Met Lys Arg Val Val Gln His Thr Lys Gly Cys Lys Arg
    1760                1765                1770

Lys Thr Asn Gly Gly Cys Pro Ile Cys Lys Gln Leu Ile Ala Leu
    1775                1780                1785

Cys Cys Tyr His Ala Lys His Cys Gln Glu Asn Lys Cys Pro Val
    1790                1795                1800

Pro Phe Cys Leu Asn Ile Lys Gln Lys Leu Arg Gln Gln Leu
    1805                1810                1815

Gln His Arg Leu Gln Gln Ala Gln Met Leu Arg Arg Arg Met Ala
    1820                1825                1830

Ser Met Gln Arg Thr Gly Val Val Gly Gln Gln Gly Leu Pro
    1835                1840                1845

Ser Pro Thr Pro Ala Thr Pro Thr Thr Pro Thr Gly Gln Gln Pro
    1850                1855                1860

Thr Thr Pro Gln Thr Pro Gln Pro Thr Ser Gln Pro Gln Pro Thr
    1865                1870                1875
```

-continued

| | | | | | | | | | | | |
|---|---|---|---|---|---|---|---|---|---|---|---|
|Pro|Pro|Asn|Ser|Met|Pro|Pro|Tyr|Leu|Pro|Arg|Thr|Gln|Ala|Ala|
| |1880| | | |1885| | | |1890| | |

Pro Pro Asn Ser Met Pro Pro Tyr Leu Pro Arg Thr Gln Ala Ala
    1880                1885                1890

Gly Pro Val Ser Gln Gly Lys Ala Ala Gly Gln Val Thr Pro Pro
    1895                1900                1905

Thr Pro Pro Gln Thr Ala Gln Pro Pro Leu Pro Gly Pro Pro Pro
    1910                1915                1920

Ala Ala Val Glu Met Ala Met Gln Ile Gln Arg Ala Ala Glu Thr
    1925                1930                1935

Gln Arg Gln Met Ala His Val Gln Ile Phe Gln Arg Pro Ile Gln
    1940                1945                1950

His Gln Met Pro Pro Met Thr Pro Met Ala Pro Met Gly Met Asn
    1955                1960                1965

Pro Pro Pro Met Thr Arg Gly Pro Ser Gly His Leu Glu Pro Gly
    1970                1975                1980

Met Gly Pro Thr Gly Met Gln Gln Pro Pro Trp Ser Gln Gly
    1985                1990                1995

Gly Leu Pro Gln Pro Gln Gln Leu Gln Ser Gly Met Pro Arg Pro
    2000                2005                2010

Ala Met Met Ser Val Ala Gln His Gly Gln Pro Leu Asn Met Ala
    2015                2020                2025

Pro Gln Pro Gly Leu Gly Gln Val Gly Ile Ser Pro Leu Lys Pro
    2030                2035                2040

Gly Thr Val Ser Gln Gln Ala Leu Gln Asn Leu Leu Arg Thr Leu
    2045                2050                2055

Arg Ser Pro Ser Ser Pro Leu Gln Gln Gln Gln Val Leu Ser Ile
    2060                2065                2070

Leu His Ala Asn Pro Gln Leu Leu Ala Ala Phe Ile Lys Gln Arg
    2075                2080                2085

Ala Ala Lys Tyr Ala Asn Ser Asn Pro Gln Pro Ile Pro Gly Gln
    2090                2095                2100

Pro Gly Met Pro Gln Gly Gln Pro Gly Leu Gln Pro Pro Thr Met
    2105                2110                2115

Pro Gly Gln Gln Gly Val His Ser Asn Pro Ala Met Gln Asn Met
    2120                2125                2130

Asn Pro Met Gln Ala Gly Val Gln Arg Ala Gly Leu Pro Gln Gln
    2135                2140                2145

Gln Pro Gln Gln Gln Leu Gln Pro Pro Met Gly Met Ser Pro
    2150                2155                2160

Gln Ala Gln Gln Met Asn Met Asn His Asn Thr Met Pro Ser Gln
    2165                2170                2175

Phe Arg Asp Ile Leu Arg Arg Gln Gln Met Met Gln Gln Gln Gln
    2180                2185                2190

Gln Gln Gly Ala Gly Pro Gly Ile Gly Pro Gly Met Ala Asn His
    2195                2200                2205

Asn Gln Phe Gln Gln Pro Gln Gly Val Gly Tyr Pro Pro Gln Gln
    2210                2215                2220

Gln Gln Arg Met Gln His His Met Gln Gln Met Gln Gln Gly Asn
    2225                2230                2235

Met Gly Gln Ile Gly Gln Leu Pro Gln Ala Leu Gly Ala Glu Ala
    2240                2245                2250

Gly Ala Ser Leu Gln Ala Tyr Gln Gln Arg Leu Leu Gln Gln Gln
    2255                2260                2265

Met Gly Ser Pro Val Gln Pro Asn Pro Met Ser Pro Gln Gln His
    2270                2275                2280

```
Met Leu Pro Asn Gln Ala Gln Ser Pro His Leu Gln Gly Gln Gln
    2285                2290                2295

Ile Pro Asn Ser Leu Ser Asn Gln Val Arg Ser Pro Gln Pro Val
    2300                2305                2310

Pro Ser Pro Arg Pro Gln Ser Gln Pro Pro His Ser Ser Pro Ser
    2315                2320                2325

Pro Arg Met Gln Pro Gln Pro Ser Pro His His Val Ser Pro Gln
    2330                2335                2340

Thr Ser Ser Pro His Pro Gly Leu Val Ala Ala Gln Ala Asn Pro
    2345                2350                2355

Met Glu Gln Gly His Phe Ala Ser Pro Asp Gln Asn Ser Met Leu
    2360                2365                2370

Ser Gln Leu Ala Ser Asn Pro Gly Met Ala Asn Leu His Gly Ala
    2375                2380                2385

Ser Ala Thr Asp Leu Gly Leu Ser Thr Asp Asn Ser Asp Leu Asn
    2390                2395                2400

Ser Asn Leu Ser Gln Ser Thr Leu Asp Ile His
    2405                2410

<210> SEQ ID NO 2
<211> LENGTH: 2442
<212> TYPE: PRT
<213> ORGANISM: Homo sapiens

<400> SEQUENCE: 2

Met Ala Glu Asn Leu Leu Asp Gly Pro Pro Asn Pro Lys Arg Ala Lys
1               5                   10                  15

Leu Ser Ser Pro Gly Phe Ser Ala Asn Asp Ser Thr Asp Phe Gly Ser
            20                  25                  30

Leu Phe Asp Leu Glu Asn Asp Leu Pro Asp Glu Leu Ile Pro Asn Gly
        35                  40                  45

Gly Glu Leu Gly Leu Leu Asn Ser Gly Asn Leu Val Pro Asp Ala Ala
    50                  55                  60

Ser Lys His Lys Gln Leu Ser Glu Leu Leu Arg Gly Gly Ser Gly Ser
65                  70                  75                  80

Ser Ile Asn Pro Gly Ile Gly Asn Val Ser Ala Ser Ser Pro Val Gln
                85                  90                  95

Gln Gly Leu Gly Gly Gln Ala Gln Gly Gln Pro Asn Ser Ala Asn Met
            100                 105                 110

Ala Ser Leu Ser Ala Met Gly Lys Ser Pro Leu Ser Gln Gly Asp Ser
        115                 120                 125

Ser Ala Pro Ser Leu Pro Lys Gln Ala Ala Ser Thr Ser Gly Pro Thr
    130                 135                 140

Pro Ala Ala Ser Gln Ala Leu Asn Pro Gln Ala Gln Lys Gln Val Gly
145                 150                 155                 160

Leu Ala Thr Ser Ser Pro Ala Thr Ser Gln Thr Gly Pro Gly Ile Cys
                165                 170                 175

Met Asn Ala Asn Phe Asn Gln Thr His Pro Gly Leu Leu Asn Ser Asn
            180                 185                 190

Ser Gly His Ser Leu Ile Asn Gln Ala Ser Gln Gly Gln Ala Gln Val
        195                 200                 205

Met Asn Gly Ser Leu Gly Ala Ala Gly Arg Gly Arg Gly Ala Gly Met
    210                 215                 220

Pro Tyr Pro Thr Pro Ala Met Gln Gly Ala Ser Ser Ser Val Leu Ala
225                 230                 235                 240
```

-continued

```
Glu Thr Leu Thr Gln Val Ser Pro Gln Met Thr Gly His Ala Gly Leu
            245                 250                 255
Asn Thr Ala Gln Ala Gly Gly Met Ala Lys Met Gly Ile Thr Gly Asn
        260                 265                 270
Thr Ser Pro Phe Gly Gln Pro Phe Ser Gln Ala Gly Gln Pro Met
    275                 280                 285
Gly Ala Thr Gly Val Asn Pro Gln Leu Ala Ser Lys Gln Ser Met Val
290                 295                 300
Asn Ser Leu Pro Thr Phe Pro Thr Asp Ile Lys Asn Thr Ser Val Thr
305                 310                 315                 320
Asn Val Pro Asn Met Ser Gln Met Gln Thr Ser Val Gly Ile Val Pro
                325                 330                 335
Thr Gln Ala Ile Ala Thr Gly Pro Thr Ala Asp Pro Glu Lys Arg Lys
            340                 345                 350
Leu Ile Gln Gln Gln Leu Val Leu Leu Leu His Ala His Lys Cys Gln
        355                 360                 365
Arg Arg Glu Gln Ala Asn Gly Glu Val Arg Ala Cys Ser Leu Pro His
    370                 375                 380
Cys Arg Thr Met Lys Asn Val Leu Asn His Met Thr His Cys Gln Ala
385                 390                 395                 400
Gly Lys Ala Cys Gln Val Ala His Cys Ala Ser Ser Arg Gln Ile Ile
                405                 410                 415
Ser His Trp Lys Asn Cys Thr Arg His Asp Cys Pro Val Cys Leu Pro
            420                 425                 430
Leu Lys Asn Ala Ser Asp Lys Arg Asn Gln Gln Thr Ile Leu Gly Ser
        435                 440                 445
Pro Ala Ser Gly Ile Gln Asn Thr Ile Gly Ser Val Gly Thr Gly Gln
    450                 455                 460
Gln Asn Ala Thr Ser Leu Ser Asn Pro Asn Pro Ile Asp Pro Ser Ser
465                 470                 475                 480
Met Gln Arg Ala Tyr Ala Ala Leu Gly Leu Pro Tyr Met Asn Gln Pro
                485                 490                 495
Gln Thr Gln Leu Gln Pro Gln Val Pro Gly Gln Gln Pro Ala Gln Pro
            500                 505                 510
Gln Thr His Gln Gln Met Arg Thr Leu Asn Pro Leu Gly Asn Asn Pro
        515                 520                 525
Met Asn Ile Pro Ala Gly Gly Ile Thr Thr Asp Gln Gln Pro Pro Asn
    530                 535                 540
Leu Ile Ser Glu Ser Ala Leu Pro Thr Ser Leu Gly Ala Thr Asn Pro
545                 550                 555                 560
Leu Met Asn Asp Gly Ser Asn Ser Gly Asn Ile Gly Thr Leu Ser Thr
                565                 570                 575
Ile Pro Thr Ala Ala Pro Pro Ser Ser Thr Gly Val Arg Lys Gly Trp
            580                 585                 590
His Glu His Val Thr Gln Asp Leu Arg Ser His Leu Val His Lys Leu
        595                 600                 605
Val Gln Ala Ile Phe Pro Thr Pro Asp Pro Ala Ala Leu Lys Asp Arg
    610                 615                 620
Arg Met Glu Asn Leu Val Ala Tyr Ala Lys Lys Val Glu Gly Asp Met
625                 630                 635                 640
Tyr Glu Ser Ala Asn Ser Arg Asp Glu Tyr Tyr His Leu Leu Ala Glu
                645                 650                 655
Lys Ile Tyr Lys Ile Gln Lys Glu Leu Glu Glu Lys Arg Arg Ser Arg
```

-continued

```
                    660                 665                 670
Leu His Lys Gln Gly Ile Leu Gly Asn Gln Pro Ala Leu Pro Ala Pro
                675                 680                 685
Gly Ala Gln Pro Pro Val Ile Pro Gln Ala Gln Pro Val Arg Pro Pro
            690                 695                 700
Asn Gly Pro Leu Ser Leu Pro Val Asn Arg Met Gln Val Ser Gln Gly
705                 710                 715                 720
Met Asn Ser Phe Asn Pro Met Ser Leu Gly Asn Val Gln Leu Pro Gln
                725                 730                 735
Ala Pro Met Gly Pro Arg Ala Ala Ser Pro Met Asn His Ser Val Gln
            740                 745                 750
Met Asn Ser Met Gly Ser Val Pro Gly Met Ala Ile Ser Pro Ser Arg
            755                 760                 765
Met Pro Gln Pro Pro Asn Met Met Gly Ala His Thr Asn Asn Met Met
        770                 775                 780
Ala Gln Ala Pro Ala Gln Ser Gln Phe Leu Pro Gln Asn Gln Phe Pro
785                 790                 795                 800
Ser Ser Ser Gly Ala Met Ser Val Gly Met Gly Gln Pro Pro Ala Gln
                805                 810                 815
Thr Gly Val Ser Gln Gly Gln Val Pro Gly Ala Ala Leu Pro Asn Pro
            820                 825                 830
Leu Asn Met Leu Gly Pro Gln Ala Ser Gln Leu Pro Cys Pro Pro Val
            835                 840                 845
Thr Gln Ser Pro Leu His Pro Thr Pro Pro Ala Ser Thr Ala Ala
        850                 855                 860
Gly Met Pro Ser Leu Gln His Thr Thr Pro Pro Gly Met Thr Pro Pro
865                 870                 875                 880
Gln Pro Ala Ala Pro Thr Gln Pro Ser Thr Pro Val Ser Ser Ser Gly
                885                 890                 895
Gln Thr Pro Thr Pro Thr Pro Gly Ser Val Pro Ser Ala Thr Gln Thr
            900                 905                 910
Gln Ser Thr Pro Thr Val Gln Ala Ala Ala Gln Ala Gln Val Thr Pro
            915                 920                 925
Gln Pro Gln Thr Pro Val Gln Pro Pro Ser Val Ala Thr Pro Gln Ser
            930                 935                 940
Ser Gln Gln Gln Pro Thr Pro Val His Ala Gln Pro Pro Gly Thr Pro
945                 950                 955                 960
Leu Ser Gln Ala Ala Ala Ser Ile Asp Asn Arg Val Pro Thr Pro Ser
                965                 970                 975
Ser Val Ala Ser Ala Glu Thr Asn Ser Gln Gln Pro Gly Pro Asp Val
            980                 985                 990
Pro Val Leu Glu Met Lys Thr Glu  Thr Gln Ala Glu Asp  Thr Glu Pro
            995                 1000                1005
Asp Pro  Gly Glu Ser Lys  Gly Glu Pro Arg Ser  Glu Met Met Glu
        1010                1015                1020
Glu Asp  Leu Gln Gly Ala Ser  Gln Val Lys Glu Glu  Thr Asp Ile
            1025                1030                1035
Ala Glu  Gln Lys Ser Glu Pro  Met Glu Val Asp Glu  Lys Lys Pro
            1040                1045                1050
Glu Val  Lys Val Glu Val Lys  Glu Glu Glu Glu Ser  Ser Ser Asn
            1055                1060                1065
Gly Thr  Ala Ser Gln Ser Thr  Ser Pro Ser Gln Pro  Arg Lys Lys
            1070                1075                1080
```

-continued

```
Ile Phe Lys Pro Glu Glu Leu Arg Gln Ala Leu Met Pro Thr Leu
1085                1090                1095

Glu Ala Leu Tyr Arg Gln Asp Pro Glu Ser Leu Pro Phe Arg Gln
1100                1105                1110

Pro Val Asp Pro Gln Leu Leu Gly Ile Pro Asp Tyr Phe Asp Ile
1115                1120                1125

Val Lys Asn Pro Met Asp Leu Ser Thr Ile Lys Arg Lys Leu Asp
1130                1135                1140

Thr Gly Gln Tyr Gln Glu Pro Trp Gln Tyr Val Asp Asp Val Trp
1145                1150                1155

Leu Met Phe Asn Asn Ala Trp Leu Tyr Asn Arg Lys Thr Ser Arg
1160                1165                1170

Val Tyr Lys Phe Cys Ser Lys Leu Ala Glu Val Phe Glu Gln Glu
1175                1180                1185

Ile Asp Pro Val Met Gln Ser Leu Gly Tyr Cys Cys Gly Arg Lys
1190                1195                1200

Tyr Glu Phe Ser Pro Gln Thr Leu Cys Cys Tyr Gly Lys Gln Leu
1205                1210                1215

Cys Thr Ile Pro Arg Asp Ala Ala Tyr Tyr Ser Tyr Gln Asn Arg
1220                1225                1230

Tyr His Phe Cys Glu Lys Cys Phe Thr Glu Ile Gln Gly Glu Asn
1235                1240                1245

Val Thr Leu Gly Asp Asp Pro Ser Gln Pro Gln Thr Thr Ile Ser
1250                1255                1260

Lys Asp Gln Phe Glu Lys Lys Asn Asp Thr Leu Asp Pro Glu
1265                1270                1275

Pro Phe Val Asp Cys Lys Glu Cys Gly Arg Lys Met His Gln Ile
1280                1285                1290

Cys Val Leu His Tyr Asp Ile Ile Trp Pro Ser Gly Phe Val Cys
1295                1300                1305

Asp Asn Cys Leu Lys Lys Thr Gly Arg Pro Arg Lys Glu Asn Lys
1310                1315                1320

Phe Ser Ala Lys Arg Leu Gln Thr Thr Arg Leu Gly Asn His Leu
1325                1330                1335

Glu Asp Arg Val Asn Lys Phe Leu Arg Arg Gln Asn His Pro Glu
1340                1345                1350

Ala Gly Glu Val Phe Val Arg Val Val Ala Ser Ser Asp Lys Thr
1355                1360                1365

Val Glu Val Lys Pro Gly Met Lys Ser Arg Phe Val Asp Ser Gly
1370                1375                1380

Glu Met Ser Glu Ser Phe Pro Tyr Arg Thr Lys Ala Leu Phe Ala
1385                1390                1395

Phe Glu Glu Ile Asp Gly Val Asp Val Cys Phe Phe Gly Met His
1400                1405                1410

Val Gln Glu Tyr Gly Ser Asp Cys Pro Pro Asn Thr Arg Arg
1415                1420                1425

Val Tyr Ile Ser Tyr Leu Asp Ser Ile His Phe Phe Arg Pro Arg
1430                1435                1440

Cys Leu Arg Thr Ala Val Tyr His Glu Ile Leu Ile Gly Tyr Leu
1445                1450                1455

Glu Tyr Val Lys Lys Leu Gly Tyr Val Thr Gly His Ile Trp Ala
1460                1465                1470

Cys Pro Pro Ser Glu Gly Asp Asp Tyr Ile Phe His Cys His Pro
1475                1480                1485
```

```
Pro Asp Gln Lys Ile Pro Lys Pro Lys Arg Leu Gln Glu Trp Tyr
    1490            1495                1500
Lys Lys Met Leu Asp Lys Ala Phe Ala Glu Arg Ile Ile His Asp
1505                1510                1515
Tyr Lys Asp Ile Phe Lys Gln Ala Thr Glu Asp Arg Leu Thr Ser
1520                1525                1530
Ala Lys Glu Leu Pro Tyr Phe Glu Gly Asp Phe Trp Pro Asn Val
1535                1540                1545
Leu Glu Glu Ser Ile Lys Glu Leu Glu Gln Glu Glu Glu Glu Arg
1550                1555                1560
Lys Lys Glu Glu Ser Thr Ala Ala Ser Glu Thr Thr Glu Gly Ser
1565                1570                1575
Gln Gly Asp Ser Lys Asn Ala Lys Lys Lys Asn Lys Lys Lys Thr
1580                1585                1590
Asn Lys Asn Lys Ser Ser Ile Ser Arg Ala Asn Lys Lys Lys Pro
1595                1600                1605
Ser Met Pro Asn Val Ser Asn Asp Leu Ser Gln Lys Leu Tyr Ala
1610                1615                1620
Thr Met Glu Lys His Lys Glu Val Phe Phe Val Ile His Leu His
1625                1630                1635
Ala Gly Pro Val Ile Asn Thr Leu Pro Pro Ile Val Asp Pro Asp
1640                1645                1650
Pro Leu Leu Ser Cys Asp Leu Met Asp Gly Arg Asp Ala Phe Leu
1655                1660                1665
Thr Leu Ala Arg Asp Lys His Trp Glu Phe Ser Ser Leu Arg Arg
1670                1675                1680
Ser Lys Trp Ser Thr Leu Cys Met Leu Val Glu Leu His Thr Gln
1685                1690                1695
Gly Gln Asp Arg Phe Val Tyr Thr Cys Asn Glu Cys Lys His His
1700                1705                1710
Val Glu Thr Arg Trp His Cys Thr Val Cys Glu Asp Tyr Asp Leu
1715                1720                1725
Cys Ile Asn Cys Tyr Asn Thr Lys Ser His Ala His Lys Met Val
1730                1735                1740
Lys Trp Gly Leu Gly Leu Asp Asp Glu Gly Ser Ser Gln Gly Glu
1745                1750                1755
Pro Gln Ser Lys Ser Pro Gln Glu Ser Arg Arg Leu Ser Ile Gln
1760                1765                1770
Arg Cys Ile Gln Ser Leu Val His Ala Cys Gln Cys Arg Asn Ala
1775                1780                1785
Asn Cys Ser Leu Pro Ser Cys Gln Lys Met Lys Arg Val Val Gln
1790                1795                1800
His Thr Lys Gly Cys Lys Arg Lys Thr Asn Gly Gly Cys Pro Val
1805                1810                1815
Cys Lys Gln Leu Ile Ala Leu Cys Cys Tyr His Ala Lys His Cys
1820                1825                1830
Gln Glu Asn Lys Cys Pro Val Pro Phe Cys Leu Asn Ile Lys His
1835                1840                1845
Lys Leu Arg Gln Gln Gln Ile Gln His Arg Leu Gln Gln Ala Gln
1850                1855                1860
Leu Met Arg Arg Arg Met Ala Thr Met Asn Thr Arg Asn Val Pro
1865                1870                1875
Gln Gln Ser Leu Pro Ser Pro Thr Ser Ala Pro Pro Gly Thr Pro
```

-continued

```
                1880                1885                1890

Thr Gln Gln Pro Ser Thr Gln Thr Pro Gln Pro Pro Ala Gln
            1895                1900                1905

Pro Gln Pro Ser Pro Val Ser Met Ser Pro Ala Gly Phe Pro Ser
        1910                1915                1920

Val Ala Arg Thr Gln Pro Pro Thr Thr Val Ser Thr Gly Lys Pro
        1925                1930                1935

Thr Ser Gln Val Pro Ala Pro Pro Pro Pro Ala Gln Pro Pro Pro
        1940                1945                1950

Ala Ala Val Glu Ala Ala Arg Gln Ile Glu Arg Glu Ala Gln Gln
        1955                1960                1965

Gln Gln His Leu Tyr Arg Val Asn Ile Asn Asn Ser Met Pro Pro
        1970                1975                1980

Gly Arg Thr Gly Met Gly Thr Pro Gly Ser Gln Met Ala Pro Val
        1985                1990                1995

Ser Leu Asn Val Pro Arg Pro Asn Gln Val Ser Gly Pro Val Met
        2000                2005                2010

Pro Ser Met Pro Pro Gly Gln Trp Gln Gln Ala Pro Leu Pro Gln
        2015                2020                2025

Gln Gln Pro Met Pro Gly Leu Pro Arg Pro Val Ile Ser Met Gln
        2030                2035                2040

Ala Gln Ala Ala Val Ala Gly Pro Arg Met Pro Ser Val Gln Pro
        2045                2050                2055

Pro Arg Ser Ile Ser Pro Ser Ala Leu Gln Asp Leu Leu Arg Thr
        2060                2065                2070

Leu Lys Ser Pro Ser Ser Pro Gln Gln Gln Gln Gln Val Leu Asn
        2075                2080                2085

Ile Leu Lys Ser Asn Pro Gln Leu Met Ala Ala Phe Ile Lys Gln
        2090                2095                2100

Arg Thr Ala Lys Tyr Val Ala Asn Gln Pro Gly Met Gln Pro Gln
        2105                2110                2115

Pro Gly Leu Gln Ser Gln Pro Gly Met Gln Pro Gln Pro Gly Met
        2120                2125                2130

His Gln Gln Pro Ser Leu Gln Asn Leu Asn Ala Met Gln Ala Gly
        2135                2140                2145

Val Pro Arg Pro Gly Val Pro Pro Gln Gln Gln Ala Met Gly Gly
        2150                2155                2160

Leu Asn Pro Gln Gly Gln Ala Leu Asn Ile Met Asn Pro Gly His
        2165                2170                2175

Asn Pro Asn Met Ala Ser Met Asn Pro Gln Tyr Arg Glu Met Leu
        2180                2185                2190

Arg Arg Gln Leu Leu Gln Gln Gln Gln Gln Gln Gln Gln Gln Gln
        2195                2200                2205

Gln Gln Gln Gln Gln Gln Gln Gly Ser Ala Gly Met Ala Gly
        2210                2215                2220

Gly Met Ala Gly His Gly Gln Phe Gln Gln Pro Gln Gly Pro Gly
        2225                2230                2235

Gly Tyr Pro Pro Ala Met Gln Gln Gln Arg Met Gln Gln His
        2240                2245                2250

Leu Pro Leu Gln Gly Ser Ser Met Gly Gln Met Ala Ala Gln Met
        2255                2260                2265

Gly Gln Leu Gly Gln Met Gly Gln Pro Gly Leu Gly Ala Asp Ser
        2270                2275                2280
```

```
Thr Pro Asn Ile Gln Gln Ala Leu Gln Gln Arg Ile Leu Gln Gln
    2285                2290                2295

Gln Gln Met Lys Gln Gln Ile Gly Ser Pro Gly Gln Pro Asn Pro
    2300                2305                2310

Met Ser Pro Gln Gln His Met Leu Ser Gly Gln Pro Gln Ala Ser
    2315                2320                2325

His Leu Pro Gly Gln Gln Ile Ala Thr Ser Leu Ser Asn Gln Val
    2330                2335                2340

Arg Ser Pro Ala Pro Val Gln Ser Pro Arg Pro Gln Ser Gln Pro
    2345                2350                2355

Pro His Ser Ser Pro Ser Pro Arg Ile Gln Pro Gln Pro Ser Pro
    2360                2365                2370

His His Val Ser Pro Gln Thr Gly Ser Pro His Pro Gly Leu Ala
    2375                2380                2385

Val Thr Met Ala Ser Ser Ile Asp Gln Gly His Leu Gly Asn Pro
    2390                2395                2400

Glu Gln Ser Ala Met Leu Pro Gln Leu Asn Thr Pro Ser Arg Ser
    2405                2410                2415

Ala Leu Ser Ser Glu Leu Ser Leu Val Gly Asp Thr Thr Gly Asp
    2420                2425                2430

Thr Leu Glu Lys Phe Val Glu Gly Leu
    2435                2440

<210> SEQ ID NO 3
<211> LENGTH: 19
<212> TYPE: PRT
<213> ORGANISM: Artificial sequence
<220> FEATURE:
<223> OTHER INFORMATION: Synthetic peptide

<400> SEQUENCE: 3

Ser Gly Arg Gly Lys Gln Gly Gly Lys Ala Arg Ala Lys Ala Lys Ser
1               5                   10                  15

Arg Ser Ser

<210> SEQ ID NO 4
<211> LENGTH: 19
<212> TYPE: PRT
<213> ORGANISM: Artificial sequence
<220> FEATURE:
<223> OTHER INFORMATION: Synthetic peptide

<400> SEQUENCE: 4

Pro Ala Pro Lys Lys Gly Ser Lys Lys Ala Val Thr Lys Ala Gln Lys
1               5                   10                  15

Lys Asp Gly

<210> SEQ ID NO 5
<211> LENGTH: 19
<212> TYPE: PRT
<213> ORGANISM: Artificial sequence
<220> FEATURE:
<223> OTHER INFORMATION: Synthetic peptide

<400> SEQUENCE: 5

Ser Thr Gly Gly Lys Ala Pro Arg Lys Gln Leu Ala Thr Lys Ala Ala
1               5                   10                  15

Arg Lys Ser

<210> SEQ ID NO 6
```

```
<211> LENGTH: 19
<212> TYPE: PRT
<213> ORGANISM: Artificial sequence
<220> FEATURE:
<223> OTHER INFORMATION: Synthetic peptide

<400> SEQUENCE: 6

Gly Lys Gly Gly Lys Gly Leu Gly Lys Gly Gly Ala Lys Arg His Arg
1               5                   10                  15

Lys Val Leu

<210> SEQ ID NO 7
<211> LENGTH: 19
<212> TYPE: PRT
<213> ORGANISM: Artificial sequence
<220> FEATURE:
<223> OTHER INFORMATION: Synthetic peptide

<400> SEQUENCE: 7

Ala His Ser Ser His Leu Lys Ser Lys Lys Gly Gln Ser Thr Ser Arg
1               5                   10                  15

His Lys Lys

<210> SEQ ID NO 8
<211> LENGTH: 19
<212> TYPE: PRT
<213> ORGANISM: Artificial sequence
<220> FEATURE:
<223> OTHER INFORMATION: Synthetic peptide

<400> SEQUENCE: 8

Asn Gly Ala Ala Ser Lys Arg Ala Phe Lys Gln Ser Pro Pro Ala Val
1               5                   10                  15

Pro Ala Leu

<210> SEQ ID NO 9
<211> LENGTH: 19
<212> TYPE: PRT
<213> ORGANISM: Artificial sequence
<220> FEATURE:
<223> OTHER INFORMATION: Synthetic peptide

<400> SEQUENCE: 9

Val Gln Thr Lys Gly Lys Arg Gly Ala Lys Gly Lys Gln Ala Glu Tyr
1               5                   10                  15

Ala Tyr Gln

<210> SEQ ID NO 10
<211> LENGTH: 19
<212> TYPE: PRT
<213> ORGANISM: Artificial sequence
<220> FEATURE:
<223> OTHER INFORMATION: Synthetic peptide

<400> SEQUENCE: 10

Arg Gly Arg His Pro Gly Lys Gly Val Lys Ser Pro Gly Glu Lys Ser
1               5                   10                  15

Arg Tyr Glu

<210> SEQ ID NO 11
<211> LENGTH: 19
<212> TYPE: PRT
<213> ORGANISM: Artificial sequence
<220> FEATURE:
<223> OTHER INFORMATION: Synthetic peptide
```

```
<400> SEQUENCE: 11

Cys Ser Thr Asp Glu Val Lys Ile Phe Lys Asp Glu Gly Asp Arg Glu
1               5                   10                  15

Asp Glu Lys

<210> SEQ ID NO 12
<211> LENGTH: 19
<212> TYPE: PRT
<213> ORGANISM: Artificial sequence
<220> FEATURE:
<223> OTHER INFORMATION: Synthetic peptide

<400> SEQUENCE: 12

Arg Pro Arg Gly Arg Pro Lys Gly Ser Lys Asn Lys Gly Ala Ala Lys
1               5                   10                  15

Thr Arg Lys

<210> SEQ ID NO 13
<211> LENGTH: 19
<212> TYPE: PRT
<213> ORGANISM: Artificial sequence
<220> FEATURE:
<223> OTHER INFORMATION: Synthetic peptide

<400> SEQUENCE: 13

Asn Glu Asp Pro Asp Glu Lys Arg Arg Lys Phe Leu Glu Arg Asn Arg
1               5                   10                  15

Ala Ala Ala

<210> SEQ ID NO 14
<211> LENGTH: 19
<212> TYPE: PRT
<213> ORGANISM: Artificial sequence
<220> FEATURE:
<223> OTHER INFORMATION: Synthetic peptide

<400> SEQUENCE: 14

Ala Gln Glu Ile Lys Tyr Gly Pro Leu Lys Met Leu Pro Gln Thr Pro
1               5                   10                  15

Ser His Leu

<210> SEQ ID NO 15
<211> LENGTH: 19
<212> TYPE: PRT
<213> ORGANISM: Artificial sequence
<220> FEATURE:
<223> OTHER INFORMATION: Synthetic peptide

<400> SEQUENCE: 15

Lys Arg Lys Arg Thr Tyr Glu Thr Phe Lys Ser Ile Met Lys Lys Ser
1               5                   10                  15

Pro Phe Ser

<210> SEQ ID NO 16
<211> LENGTH: 19
<212> TYPE: PRT
<213> ORGANISM: Artificial sequence
<220> FEATURE:
<223> OTHER INFORMATION: Synthetic peptide

<400> SEQUENCE: 16

Asp Ile Pro Lys Glu Glu Ala Phe Gly Lys Tyr Cys Arg Pro Glu Ser
1               5                   10                  15
```

```
<210> SEQ ID NO 17
<211> LENGTH: 19
<212> TYPE: PRT
<213> ORGANISM: Artificial sequence
<220> FEATURE:
<223> OTHER INFORMATION: Synthetic peptide

<400> SEQUENCE: 17

Gln Thr Arg Asn Arg Lys Ala Ser Gly Lys Gly Lys Lys Arg Gly
1               5                   10                  15

Ser Asn Leu

<210> SEQ ID NO 18
<211> LENGTH: 19
<212> TYPE: PRT
<213> ORGANISM: Artificial sequence
<220> FEATURE:
<223> OTHER INFORMATION: Synthetic peptide

<400> SEQUENCE: 18

Ala Gly Arg Cys Leu Leu Trp Ala Cys Lys Ala Cys Lys Arg Lys Thr
1               5                   10                  15

Thr Asn Ala

<210> SEQ ID NO 19
<211> LENGTH: 19
<212> TYPE: PRT
<213> ORGANISM: Artificial sequence
<220> FEATURE:
<223> OTHER INFORMATION: Synthetic peptide

<400> SEQUENCE: 19

Glu Ala Gly Met Thr Leu Gly Ala Arg Lys Leu Lys Lys Leu Gly Asn
1               5                   10                  15

Leu Lys Leu

<210> SEQ ID NO 20
<211> LENGTH: 19
<212> TYPE: PRT
<213> ORGANISM: Artificial sequence
<220> FEATURE:
<223> OTHER INFORMATION: Synthetic peptide

<400> SEQUENCE: 20

Lys Ala Leu Gly Ile Ser Tyr Gly Arg Lys Lys Arg Arg Gln Arg Arg
1               5                   10                  15

Arg Ala His

<210> SEQ ID NO 21
<211> LENGTH: 19
<212> TYPE: PRT
<213> ORGANISM: Artificial sequence
<220> FEATURE:
<223> OTHER INFORMATION: Synthetic peptide

<400> SEQUENCE: 21

Lys Gly Asp Ser Lys Asn Ala Lys Lys Lys Asn Asn Lys Lys Thr Ser
1               5                   10                  15

Lys Asn Lys

<210> SEQ ID NO 22
```

<211> LENGTH: 380
<212> TYPE: PRT
<213> ORGANISM: Homo sapiens

<400> SEQUENCE: 22

```
Lys Phe Ser Ala Lys Arg Leu Pro Ser Thr Arg Leu Gly Thr Phe Leu
1               5                   10                  15

Glu Asn Arg Val Asn Asp Phe Leu Arg Arg Gln Asn His Pro Glu Ser
            20                  25                  30

Gly Glu Val Thr Val Arg Val His Ala Ser Asp Lys Thr Val Glu
        35                  40                  45

Val Lys Pro Gly Met Lys Ala Arg Phe Val Asp Ser Gly Glu Met Ala
50                  55                  60

Glu Ser Phe Pro Tyr Arg Thr Lys Ala Leu Phe Ala Phe Glu Glu Ile
65                  70                  75                  80

Asp Gly Val Asp Leu Cys Phe Phe Gly Met His Val Gln Glu Tyr Gly
                85                  90                  95

Ser Asp Cys Pro Pro Pro Asn Gln Arg Arg Val Tyr Ile Ser Tyr Leu
            100                 105                 110

Asp Ser Val His Phe Phe Arg Pro Lys Cys Leu Arg Thr Ala Val Tyr
        115                 120                 125

His Glu Ile Leu Ile Gly Tyr Leu Glu Tyr Val Lys Lys Leu Gly Tyr
130                 135                 140

Thr Thr Gly His Ile Trp Ala Cys Pro Pro Ser Glu Gly Asp Asp Tyr
145                 150                 155                 160

Ile Phe His Cys His Pro Pro Asp Gln Lys Ile Pro Lys Pro Lys Arg
                165                 170                 175

Leu Gln Glu Trp Tyr Lys Lys Met Leu Asp Lys Ala Val Ser Glu Arg
            180                 185                 190

Ile Val His Asp Tyr Lys Asp Ile Phe Lys Gln Ala Thr Glu Asp Arg
        195                 200                 205

Leu Thr Ser Ala Lys Glu Leu Pro Tyr Phe Glu Gly Asp Phe Trp Pro
210                 215                 220

Asn Val Leu Glu Glu Ser Ile Lys Glu Leu Glu Gln Glu Glu Glu Glu
225                 230                 235                 240

Arg Lys Arg Glu Glu Asn Thr Ser Asn Glu Ser Thr Asp Val Thr Lys
                245                 250                 255

Gly Asp Ser Lys Asn Ala Lys Lys Lys Asn Asn Lys Lys Thr Ser Lys
            260                 265                 270

Asn Lys Ser Ser Leu Ser Arg Gly Asn Lys Lys Pro Gly Met Pro
        275                 280                 285

Asn Val Ser Asn Asp Leu Ser Gln Lys Leu Tyr Ala Thr Met Glu Lys
290                 295                 300

His Lys Glu Val Phe Phe Val Ile Arg Leu Ile Ala Gly Pro Ala Ala
305                 310                 315                 320

Asn Ser Leu Pro Pro Ile Val Asp Pro Asp Pro Leu Ile Pro Cys Asp
                325                 330                 335

Leu Met Asp Gly Arg Asp Ala Phe Leu Thr Leu Ala Arg Asp Lys His
            340                 345                 350

Leu Glu Phe Ser Ser Leu Arg Arg Ala Gln Trp Ser Thr Met Cys Met
        355                 360                 365

Leu Val Glu Leu His Thr Gln Ser Gln Asp Arg Phe
370                 375                 380
```

<210> SEQ ID NO 23

<211> LENGTH: 381
<212> TYPE: PRT
<213> ORGANISM: Homo sapiens

<400> SEQUENCE: 23

Lys Phe Ser Ala Lys Arg Leu Gln Thr Thr Arg Leu Gly Asn His Leu
1               5                   10                  15

Glu Asp Arg Val Asn Lys Phe Leu Arg Arg Gln Asn His Pro Glu Ala
            20                  25                  30

Gly Glu Val Phe Val Arg Val Ala Ser Ser Asp Lys Thr Val Glu
        35                  40                  45

Val Lys Pro Gly Met Lys Ser Arg Phe Val Asp Ser Gly Glu Met Ser
50                  55                  60

Glu Ser Phe Pro Tyr Arg Thr Lys Ala Leu Phe Ala Phe Glu Ile
65                  70                  75                  80

Asp Gly Val Asp Val Cys Phe Phe Gly Met His Val Gln Glu Tyr Gly
                85                  90                  95

Ser Asp Cys Pro Pro Asn Thr Arg Arg Val Tyr Ile Ser Tyr Leu
            100                 105                 110

Asp Ser Ile His Phe Phe Arg Pro Arg Cys Leu Arg Thr Ala Val Tyr
            115                 120                 125

His Glu Ile Leu Ile Gly Tyr Leu Glu Tyr Val Lys Lys Leu Gly Tyr
130                 135                 140

Val Thr Gly His Ile Trp Ala Cys Pro Pro Ser Glu Gly Asp Asp Tyr
145                 150                 155                 160

Ile Phe His Cys His Pro Pro Asp Gln Lys Ile Pro Lys Pro Lys Arg
                165                 170                 175

Leu Gln Glu Trp Tyr Lys Lys Met Leu Asp Lys Ala Phe Ala Glu Arg
            180                 185                 190

Ile Ile His Asp Tyr Lys Asp Ile Phe Lys Gln Ala Thr Glu Asp Arg
        195                 200                 205

Leu Thr Ser Ala Lys Glu Leu Pro Tyr Phe Glu Gly Asp Phe Trp Pro
210                 215                 220

Asn Val Leu Glu Glu Ser Ile Lys Glu Leu Glu Gln Glu Glu Glu
225                 230                 235                 240

Arg Lys Lys Glu Glu Ser Thr Ala Ala Ser Glu Thr Thr Glu Gly Ser
                245                 250                 255

Gln Gly Asp Ser Lys Asn Ala Lys Lys Lys Asn Asn Lys Lys Thr Asn
            260                 265                 270

Lys Asn Lys Ser Ser Ile Ser Arg Ala Asn Lys Lys Lys Pro Ser Met
        275                 280                 285

Pro Asn Val Ser Asn Asp Leu Ser Gln Lys Leu Tyr Ala Thr Met Glu
290                 295                 300

Lys His Lys Glu Val Phe Phe Val Ile His Leu His Ala Gly Pro Val
305                 310                 315                 320

Ile Asn Thr Leu Pro Pro Ile Val Asp Pro Asp Pro Leu Leu Ser Cys
                325                 330                 335

Asp Leu Met Asp Gly Arg Asp Ala Phe Leu Thr Leu Ala Arg Asp Lys
            340                 345                 350

His Trp Glu Phe Ser Ser Leu Arg Arg Ser Lys Trp Ser Thr Leu Cys
        355                 360                 365

Met Leu Val Glu Leu His Thr Gln Gly Gln Asp Arg Phe
370                 375                 380

<210> SEQ ID NO 24

```
<211> LENGTH: 14
<212> TYPE: PRT
<213> ORGANISM: Artificial sequence
<220> FEATURE:
<223> OTHER INFORMATION: Synthetic peptide

<400> SEQUENCE: 24

Cys Met Leu Val Glu Leu His Thr Gln Ser Gln Asp Arg Phe
1               5                   10

<210> SEQ ID NO 25
<211> LENGTH: 15
<212> TYPE: PRT
<213> ORGANISM: Artificial sequence
<220> FEATURE:
<223> OTHER INFORMATION: Synthetic peptide

<400> SEQUENCE: 25

Gly Arg Gly Lys Gly Gly Lys Gly Leu Gly Lys Gly Gly Ala Lys
1               5                   10                  15

<210> SEQ ID NO 26
<211> LENGTH: 15
<212> TYPE: PRT
<213> ORGANISM: Artificial sequence
<220> FEATURE:
<223> OTHER INFORMATION: Synthetic peptide

<400> SEQUENCE: 26

Gly Arg Gly Asp Gly Gly Lys Gly Leu Gly Asp Gly Gly Ala Lys
1               5                   10                  15

<210> SEQ ID NO 27
<211> LENGTH: 12
<212> TYPE: PRT
<213> ORGANISM: Artificial sequence
<220> FEATURE:
<223> OTHER INFORMATION: Synthetic peptide

<400> SEQUENCE: 27

Arg Gly Ala Gly Gly Lys Gly Leu Gly Ala Gly Ala
1               5                   10

<210> SEQ ID NO 28
<211> LENGTH: 12
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (3)..(3)
<223> OTHER INFORMATION: Xaa can be any naturally occurring amino acid

<400> SEQUENCE: 28

Arg Gly Xaa Gly Gly Lys Gly Leu Gly Ala Gly Ala
1               5                   10

<210> SEQ ID NO 29
<211> LENGTH: 7
<212> TYPE: PRT
<213> ORGANISM: Artificial sequence
<220> FEATURE:
<223> OTHER INFORMATION: Synthetic peptide

<400> SEQUENCE: 29

Gly Gly Lys Gly Arg Gly Ser
1               5
```

```
<210> SEQ ID NO 30
<211> LENGTH: 12
<212> TYPE: PRT
<213> ORGANISM: Artificial sequence
<220> FEATURE:
<223> OTHER INFORMATION: Synthetic peptide

<400> SEQUENCE: 30

Gly Leu Gly Lys Gly Gly Ala Lys Arg Asn Arg Ala
1               5                   10
```